(12) United States Patent
Sæther

(10) Patent No.: US 7,997,417 B2
(45) Date of Patent: Aug. 16, 2011

(54) MEANS IN A REVERSE VENDING MACHINE (RVM) FOR RECEIVING, HANDLING, SORTING AND STORING RETURNABLE ITEMS OR OBJECTS

(75) Inventor: Geir Sæther, Asker (NO)

(73) Assignee: Tomra Systems ASA, Asker (NO)

( * ) Notice: Subject to any disclaimer, the term of this patent is extended or adjusted under 35 U.S.C. 154(b) by 796 days.

(21) Appl. No.: 11/814,183

(22) PCT Filed: Jan. 24, 2006

(86) PCT No.: PCT/NO2006/000029
§ 371 (c)(1),
(2), (4) Date: Mar. 14, 2008

(87) PCT Pub. No.: WO2006/080851
PCT Pub. Date: Aug. 3, 2006

(65) Prior Publication Data
US 2009/0120847 A1    May 14, 2009

(30) Foreign Application Priority Data

| Jan. 25, 2005 | (NO) | 20050401 |
|---|---|---|
| Jan. 25, 2005 | (NO) | 20050402 |
| Jan. 25, 2005 | (NO) | 20050403 |
| Jan. 25, 2005 | (NO) | 20050404 |
| Jan. 25, 2005 | (NO) | 20050405 |
| Jan. 25, 2005 | (NO) | 20050406 |
| Jan. 25, 2005 | (NO) | 20050407 |

(51) Int. Cl.
*G07F 7/06* (2006.01)
*B07C 5/34* (2006.01)

(52) U.S. Cl. ........ 209/522; 209/529

(58) Field of Classification Search ........ 209/522, 209/529; 194/212; 198/382, 384
See application file for complete search history.

(56) References Cited

U.S. PATENT DOCUMENTS

| 4,054,196 A | | 10/1977 | Schaufele et al. | |
|---|---|---|---|---|
| 4,241,821 A | * | 12/1980 | Wu et al. ........ | 194/209 |
| 4,248,334 A | * | 2/1981 | Hanley et al. ....... | 194/209 |
| 4,412,608 A | | 11/1983 | Kaspar et al. | |
| 4,469,212 A | | 9/1984 | DeWoolfson et al. | |
| 5,361,913 A | * | 11/1994 | Melchionna ......... | 209/583 |

(Continued)

FOREIGN PATENT DOCUMENTS

DE    10061462 A1    6/2002

(Continued)

OTHER PUBLICATIONS

International Search Report for PCT/NO2006/000029, dated Apr. 10, 2007.

*Primary Examiner* — Douglas A Hess
(74) *Attorney, Agent, or Firm* — Rodman & Rodman

(57) ABSTRACT

The reverse vending machine (RVM) receives, handles, sorts, and stores returnable items or objects. The RVM includes an item supporting, rotating, sorting and conveyor unit, an upright storage chamber for such items, a safety apparatus to avoid operational hazards, a camera aided detection device for detecting at least one of a bar code on and other characteristics, e.g. contour, of an item, a simplified token system, and a drive system with a releasable power coupling for operating the sorting device and a further storage device.

47 Claims, 49 Drawing Sheets

U.S. PATENT DOCUMENTS

| | | | |
|---|---|---|---|
| 5,624,018 A | 4/1997 | Schuff et al. | |
| 5,630,493 A * | 5/1997 | DeWoolfson et al. | 194/209 |
| 5,788,045 A | 8/1998 | Stiefel et al. | |
| 5,790,247 A * | 8/1998 | Henley et al. | 356/237.1 |
| 6,012,588 A | 1/2000 | Steidel et al. | |
| 6,137,900 A | 10/2000 | Steidel et al. | |
| 6,547,055 B2 * | 4/2003 | Coyne et al. | 194/207 |
| 6,719,146 B2 * | 4/2004 | Holmen et al. | 209/522 |
| 7,596,311 B2 * | 9/2009 | Sæther et al. | 396/431 |
| 7,754,990 B2 * | 7/2010 | Saether | 209/524 |
| 2003/0141167 A1 | 7/2003 | Holmen et al. | |

FOREIGN PATENT DOCUMENTS

| | | |
|---|---|---|
| DE | 10258069 A1 | 5/2004 |
| DE | 10348009 A1 | 5/2005 |
| GB | 791049 A | 2/1958 |
| GB | 875577 A | 8/1961 |
| WO | WO9512182 A | 5/1995 |
| WO | WO9802255 A | 1/1998 |
| WO | WO9930292 A | 6/1999 |

* cited by examiner

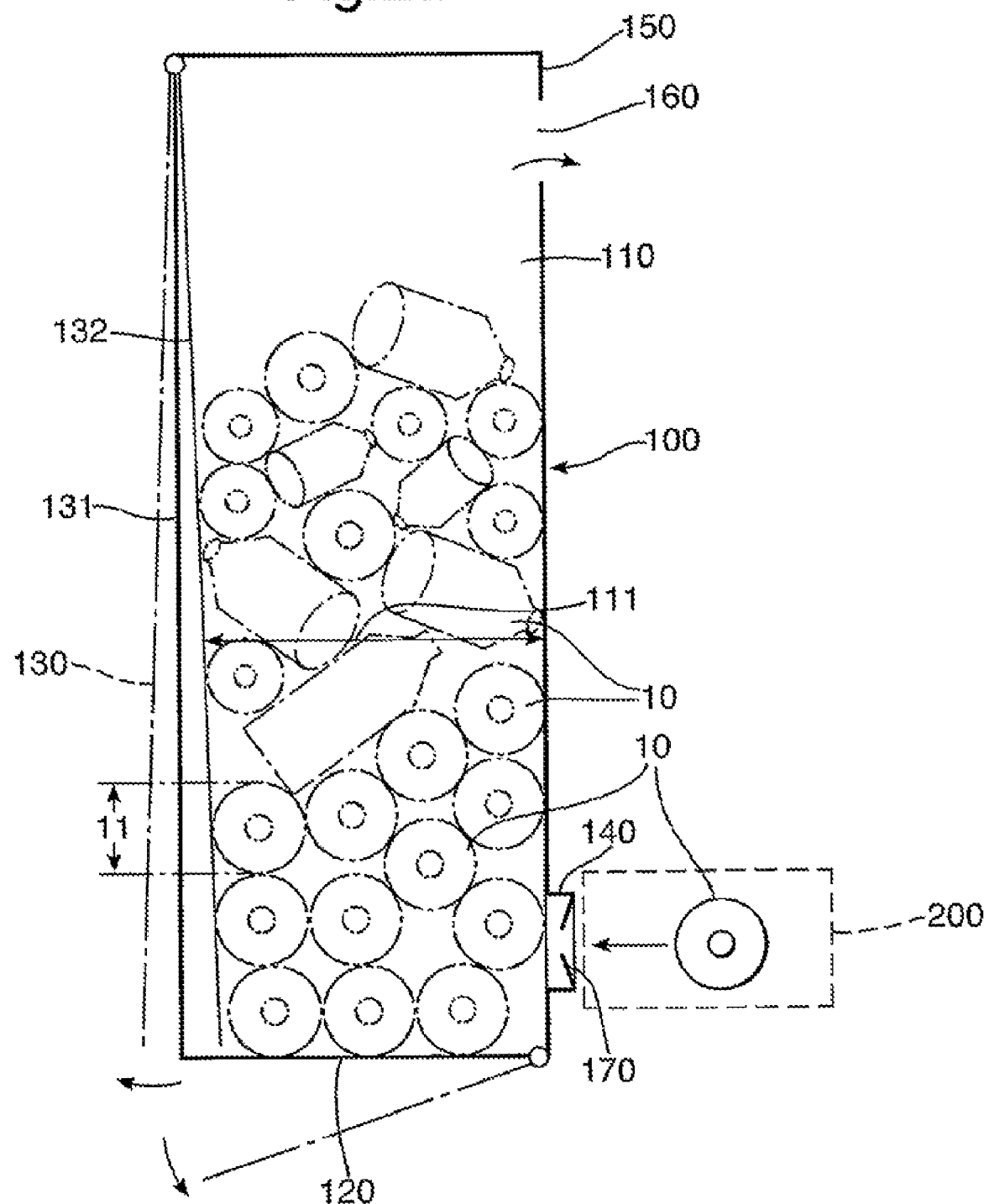

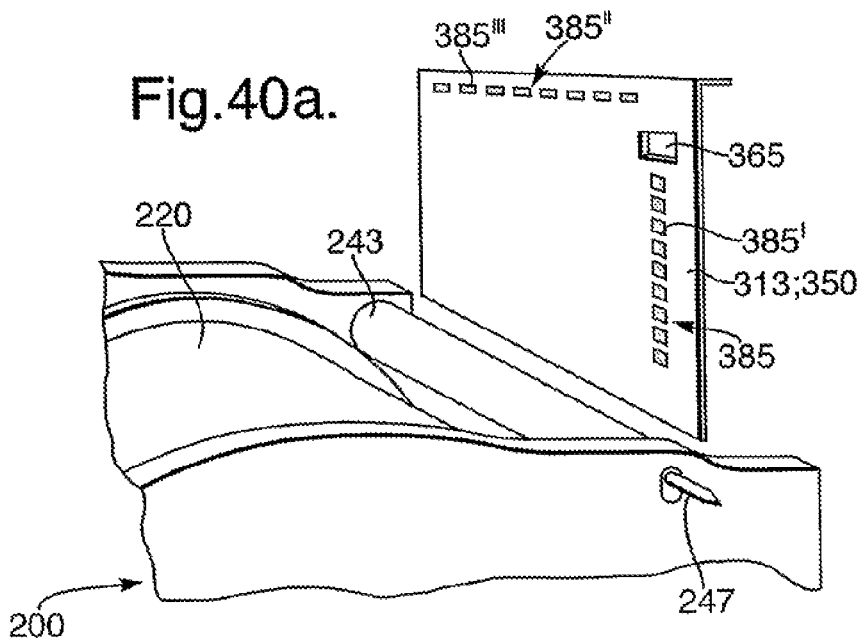
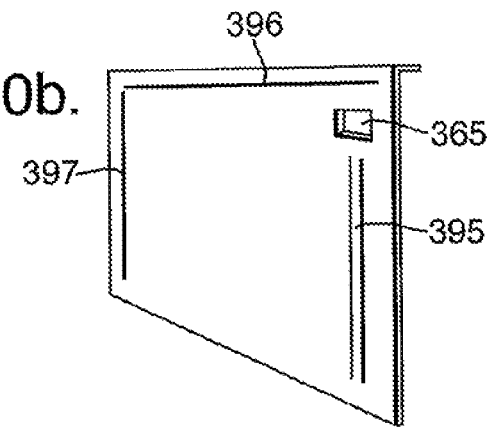
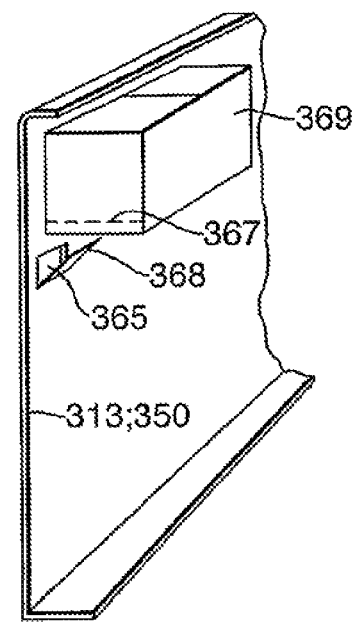
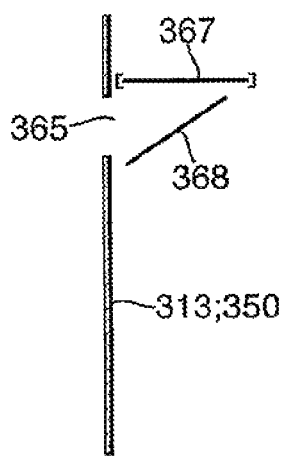
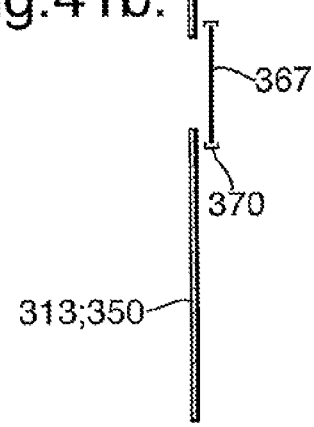

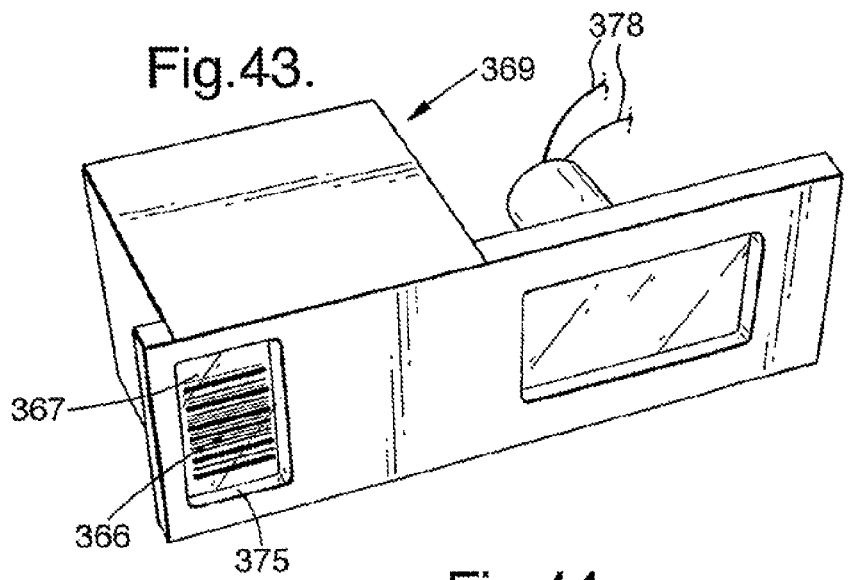
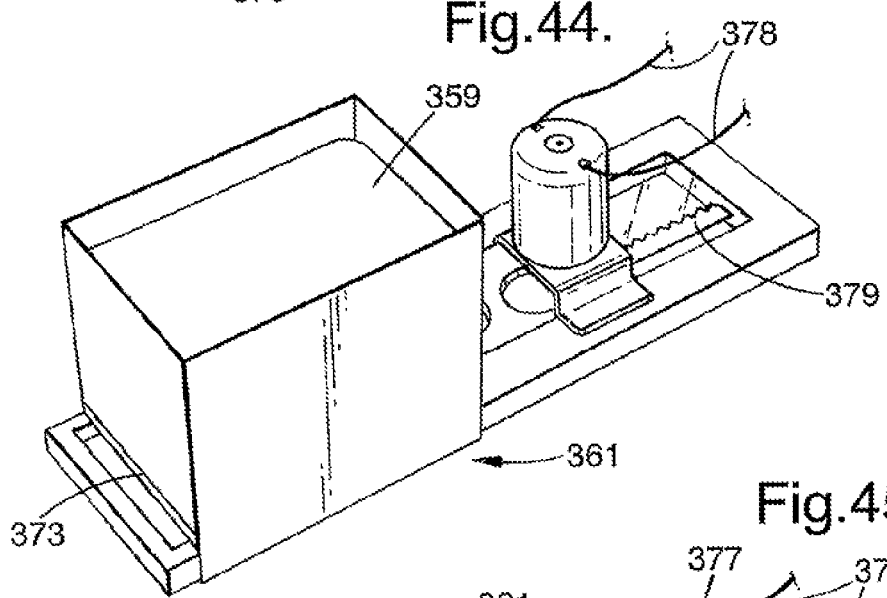
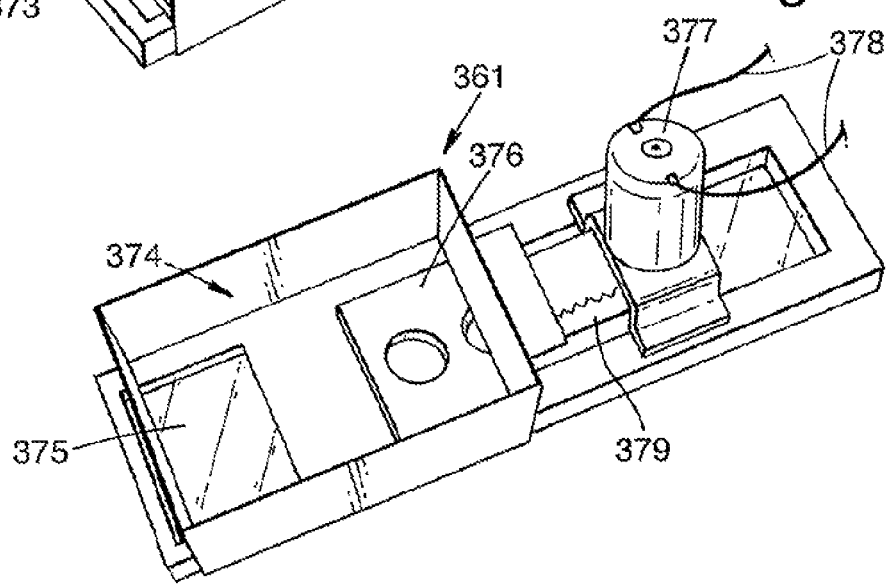

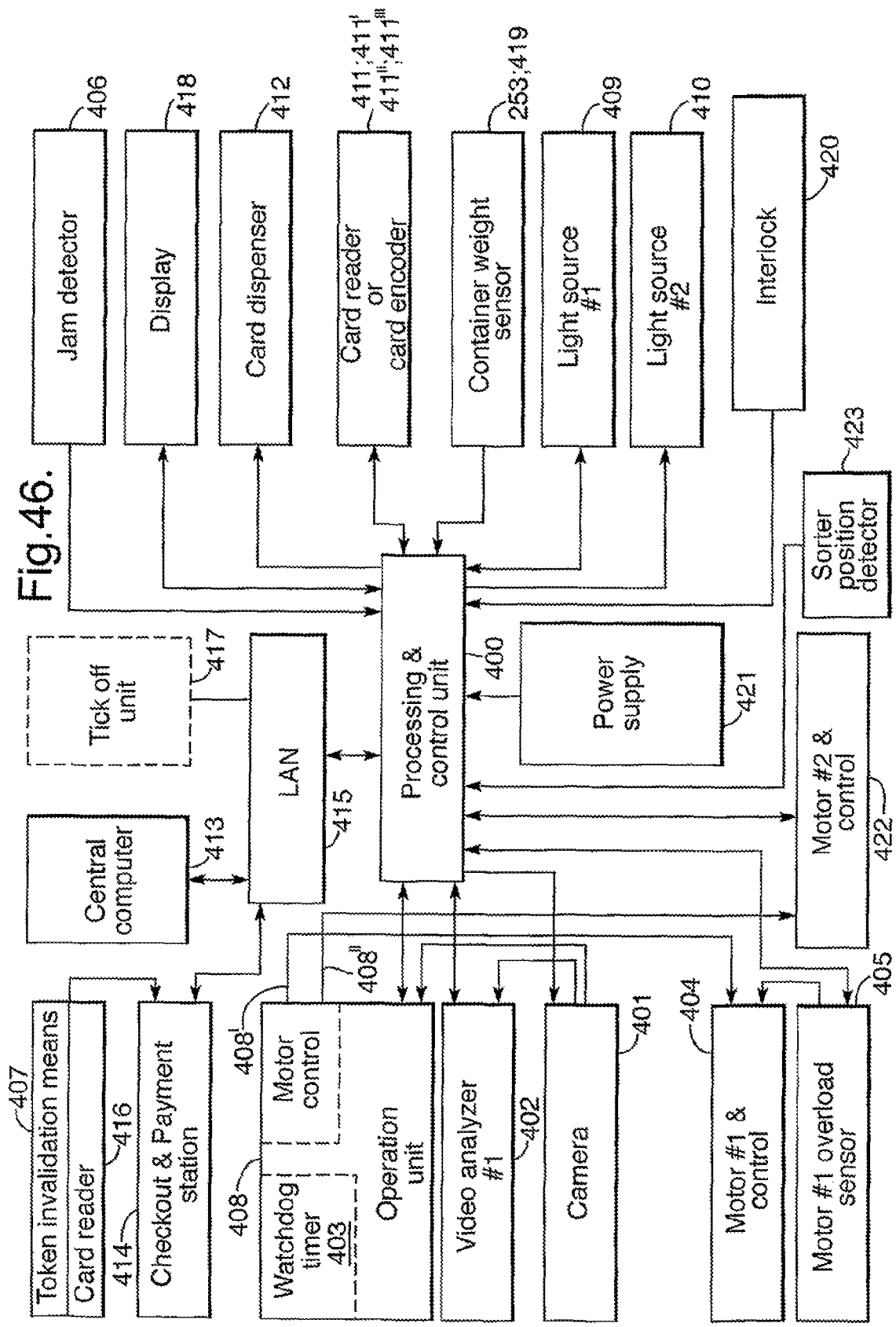

MEANS IN A REVERSE VENDING MACHINE (RVM) FOR RECEIVING, HANDLING, SORTING AND STORING RETURNABLE ITEMS OR OBJECTS

FIELD OF THE INVENTION

The present invention is related in general to apparatus far handling items or objects, e.g. for receiving, sorting and storing returnable items or objects, such as empty beverage containers like bottles, cans or the like. The invention is particularly useful in connection with reverse vending machines, although certain aspects of the present invention may also find other fields of use.

BACKGROUND OF THE INVENTION

The present invention came about following the recognition of the need to provide a more cost efficient reverse vending machine, yet simple, reliable and space saving. In particular, it was recognized the need to reduce overall cost of manufacturing such new machines by addressing such important issues to as minimizing the number of expensive components, such as e.g. camera, barcode reader, object sorter, object conveyor, object rotator, and token printer, as well as minimizing required space, especially as regards floor area.

However, in such recognition, it was revealed that the invention would become related to a plurality of aspects which all in their own respective manner would contribute to a desirable end result.

In a decade or so, environmental and economical concerns have sparred significant developments in the field of facilities for collecting cans, bottles, jars and other containers, preferably for recovering the material for recycling purposes. These days, fully automatic systems are available that are capable of receiving and storing many different types of used containers, or even parts of used containers.

Arrangements for handling recyclable items like returnable empty beverage containers are inter alia known from, the European publications EP 0 384 885 (SIG Schweizerische Industrie-Gesellschaft), EP 1311448, and the International Patent Application publication WO02/12096 (EP 1313656) (TOMRA SYSTEMS ASA) and EP 14677328 (TOMRA SYSTEMS ASA).

Till now, available fully automated systems, so-called reverse vending machines (RVMs) and back-room systems, that are capable of receiving and storing used containers have been quite complex and expensive. They have, therefore, mostly been found in larger stores, shopping centers or supermarkets, or in special facilities put up for collecting recyclable items or objects.

Accordingly, for the customer who has recyclable items or objects in smaller quantities, and who may not have at disposal a proper vehicle to facilitate easy transportation of recyclable material to a larger store, shopping center or supermarket that may be located at a distance from the person's home, it is often easier to throw the recyclable items out with the garbage.

The currently available reverse vending machines normally deliver the received objects to a back-room receiving facility or a downstairs facility. The total installation is expensive, requires substantial space, is often complex to install and service, and has operational drawbacks, in particular from a cleaning point of view. Frequent cleaning of soiled operational parts, suitably with water or special cleaning agent, is very important to secure failsafe operation. Returnable beverage containers frequently contain beverage leftovers, which often happen to come into contact with operational parts, thus making such parts sticky and causing operational failure if not properly cleaned. Cleaning is more than often a messy operation, and care has to be made not to harm electrical components.

Most RVMs need to have the ability to inspect identifying features on the object, such as e.g. a bar code. If such features are not immediately seen by a dedicated detector, the object will need to be rotated to find if such features are indeed present. An object rotating mechanism is expensive and requires substantial space in the longitudinal or depth direction of the RVM. Further, if such RVMs are also to provide object sorting, an additional sorter has to be provided, adding further to the cost of the installation, and the dimension of the RVM as regards depth dimension is in some cases prohibitive when both a rotator and a sorter are to be included. Also, most owners of stores, shopping centers or supermarkets are concerned over RVMs requiring substantial and expensive space for collecting the containers received by the RVM, such space frequently being occupied by container collection tables.

OBJECTS OF THE INVENTION

The present invention therefore has as a principal object to meet a long felt need to provide an improved automated facility for collecting returnable objects or items, such as recyclable items of plastic, metal or glass, and for overcoming the well-known mentioned drawbacks, thus yielding a low cost facility which exhibits optimal use of limited space, in particular floor space, that may be available almost everywhere, enabling their placement even in smaller stores, convenience stores, local gas stations and public areas. Thereby, such facilities may be more conveniently available to customers. These features and other features to appear through reading of the specification are some of the objectives of the present invention.

SUMMARY OF INVENTION

The invention relates particularly to a facility which allows storage of a large number of returnable items or objects in a mostly vertically oriented storage space without employing a vertical conveyor for filling the storage space.

The present invention, the invention provides a vertically oriented storage having an interior space for storing heightwise returnable items.

The invention provides for an essentially vertically oriented storage for storing in a substantially upwards filling direction returnable objects or items, particularly returnable containers like bottles, cans and the like, preferably such that are plastic, glass or metallic material.

The present invention relates to a conveyor means for a facility for receiving returnable items.

Such conveyor means are useful for receiving and sorting returnable items, and in the context of the present invention preferably for delivering returnable items for storing in the storage facility, and it has been the purpose of the present invention to provide for a very compact conveyor means for such use.

The invention also provides for a conveyor means having a movable plunger in a stationary elongate housing part.

The conveyor means as defined are particularly suitable for feeding returnable objects or items, particularly returnable containers like bottles, cans and the like, preferably made from plastic, glass or metallic material to a vertically oriented storage for storing returnable objects or items in a substantially upwards filling direction.

More specifically, the conveyor means is adapted to handle, sort and convey returnable items or objects, and for feeding such items or objects into the substantially vertically oriented storage space, without employing a vertical conveyor for filling the storage space.

In recognition of the necessity to be able to view and recognize characteristic features of an object, a fourth aspect of the present invention relates to a device for enabling camera viewing of characteristic features of an object in order to subsequently enable processing of signals related to viewed features.

Further, the invention is related to a device for enabling camera viewing of two regions of an object, in order to subsequently enable processing of signals related to viewed features.

In addition, the invention is related to a device for enabling camera viewing of characteristic features of an object, in order to subsequently enable processing of signals related to viewed features, a single camera being configured to view a location where the object can be placed and thereby cause subsequent recognition of the contour of the object, a lens being arranged between the camera and said location.

Further, the invention is related to a device for enabling camera viewing of characteristic features of an object against light providing or bright background area, in order to subsequently enable processing of signals related to viewed features, a single camera being provided and configured to view a location where the object can be placed and thereby cause detection of its contour.

Still further, the invention is related to a device using a camera to view characteristic features of an object against a light providing or bright background area, in order to subsequently enable processing related to viewed features.

It is important to note that the camera viewing features of the invention are closely interrelated.

From prior art it is conventional to view an object or article, e.g. empty beverage packaging, such as a can or bottle, against a light reflective background, the viewing being made via a lens in order that light rays which are sent towards the object are parallel rays. DE 19512133 A1 discloses such technique. On the basis of such viewing, analysis for object contour is made.

However, simultaneously with viewing of shape of a bottle or can, as disclosed in said DE 195 12 133 A1, there has also been the need to view and recognize or read other characteristic features, such as a bar code on the can or bottle.

In a reverse vending machine (RVM), it is conventional to view and recognize shape of the object at one location in the RVM and to recognize other identifiable characteristic features such as indicia, barcode etc. at another location. If e.g. a barcode is not directly visible to a barcode reader, the object must be rotated until the barcode becomes visible and can be read by the reader.

It is a well known fact that in order to be able to detect both contour of the object and read indicia or identifying features located on the object, including object rotation to find and read identifying features, multiple and separate operating units need to be provided, thus requiring extra space within the RVM to carry out the operations. If there is in addition the requirement of a sorting function, additional challenges arise as regards available space. Said EP publications EP1311448 and 1313656 disclose, with reference to an RVM for beverage container such as bottles and cans, the provisions of contour detection, barcode reading and beverage container sorting. Contour detection and sorting is made by one operating unit (see EP 1313656), and a further operating unit (EP1311448) provides for beverage container rotation to find a barcode and barcode reading.

U.S. Pat. No. 5,934,440 discloses a device with a detection station for reading barcode, rotation of the object such as e.g. a bottle to locate a barcode not immediately visible, as well as a sorting function. However, the possibility of detecting an object contour at such station is not available and needs to be performed by a separate station suitably located upstream, as disclosed in said patent.

It has therefore been a long felt need to provide for a technical solution which yields a more compact, yet simple and cost-effective arrangement and with the possibility of both detection of contour and identifying features located on the object, as well as a sorting function and other optional functions.

Accordingly the present invention provides for a device which makes use of camera aid to provide for major detection functions, and with other benefits resulting from the overall structure.

In recognition of the need to avoid operational hazards as far as possible, and above all avoid any accidental injury to a user of the facility, the present invention relates to a safety apparatus for controlling operation of functional equipment having movable parts.

It is a well known technique in a reverse vending machine (RVM) to provide movement detectors or light curtains in the form of transmitter/receiver pairs to detect when an object has reached a particular position in the RVM to alert if someone tries to move a hand into the RVM, or to view a video image to detect entry into or direction of movement into a detection region as seen by a camera. Upon such detection, action can be taken to inhibit further operation of moving parts and/or trigger an alarm. Further, in the case of transmitter/receiver pairs, expensive hardware has to be installed, aligned and serviced.

European Patent EP-0910485 (TOMRA SYSTEMS ASA) discloses a camera functionality in order to control movements in a camera field of view in connection with a reverse vending machine. Such movement control is software related.

If a particular part of a camera provided image of e.g. an entry region of a device such as a reverse vending machine for empty beverage containers is to be used for monitoring safety hazard, any software update related to camera function must also be documented and certified to ensure that said monitoring capability is still operative. Such process is time consuming and expensive. In case of e.g. camera failure, the image may appear blank as if no activity or events in the camera field of view would be present. In such a situation, an inherent safety hazard may be present.

Safety hazards e.g. include the risk of a person getting a hand injured if put into the RVM, or operational failures due to incorrect handling of the RVM by a person.

The invention therefore avoids the inherent drawbacks of the prior art solutions.

The invention is explained in more detail with reference in particular to drawing FIGS. 37a, 37b, 37c, 40a and 40b.

Reverse vending machines conventionally issue a specially printed token related to the return or redemption value of empty beverage containers received by the reverse vending machine (RVM), and the token is then taken to a rewarding unit or so-called checkout and payment station to get a cash reward or a cash deduction from a bill to be paid for other sales items or objects, e.g. groceries. However, it has also been a long felt desire to simplify dispensing of tokens in a RVM to avoid occasional and inherent printer failures well known to the expert in the art when tokens are to be printed with individual return value related data.

The present invention therefore relates to a token system for use with a reverse vending machine suitable for receiving empty packaging in the form of empty beverage containers.

A further aspect of the present invention is a token system related to a reverse vending machine which is configured to detect and identify features of an object, tokens being dispensable one-by-one from a token dispenser and configured to be related to an object being observable and detectable for object identification.

Security measures have over the past years been implemented in order to avoid recurring swindle attempt through presentation at the rewarding unit of home-made tokens with a redemption value printed thereon. Thus, the new tokens issued have also included a particular serial number, and both the redemption value and the serial number have been communicated from the RVM to a central computer, suitably located in the store or supermarket, in order to validate the token, and when the token has been presented at the rewarding unit, payment is made to the customer and the central computer then invalidates the token by removing the data from availability at the rewarding unit.

The tokens are usually made from thin paper from a roll of paper passing through a printer, suitably a thermal printer, before it is issued to the customer. Experience has, however, shown that use of such printed paper tokens has the drawback that the printer occasionally fails, the printer is expensive and needs maintenance service at regular intervals, and the paper from the paper roll is expensive and needs to be of a particular quality to yield as low failure rate as possible.

Given some of the disadvantages of the prior art tokens, the tenth and eleventh aspects of the present invention have as an object to provide for a token system that avoids printing of tokens in an RVM, yet provides the required security against swindle attempts and avoids the use of any printer and related printer maintenance.

According to the invention, the characterising features of the token system appear from the attached independent patent claims. Further embodiments appear from the related sub-claims.

Finally the present invention is concerned with the inherent problems in a reverse vending machine of disconnecting operational units for cleaning purposes, services etc., and the twelfth aspect of the present invention is accordingly related to a drive device in a reverse vending machine to forcibly drive at least one handling unit suited to handle empty packaging in the form of empty beverage containers.

It is well known in the art that equipment used for handling empty beverage containers in a reverse vending machine (RVM) is frequently soiled by beverage leftovers coming from the interior of such containers, and causing malfunction of the equipment or drive motor overload if not properly washed and cleaned at regular intervals, in many cases with a necessity for cleaning once every day.

Such equipment is conventionally made with drive motors firmly attached to the equipment either on the outside or internally, and with sophisticated or expensive plug/socket connection to power supply in the reverse vending machine.

When cleaning such equipment, often with hot water and/or pressurized water or other cleaning agent, motors and connectors may be damaged or get moist through intrusion of water, with the inherent risk of malfunction through leakage currents or even short-circuit. Therefore, expensive and sophisticated technical solutions have to be designed to avoid such damages or other operational problems or hazards. Such solutions may therefore include special purpose motors, plug and socket units, wiring etc.

The present invention therefore intends to overcome the present every-day problem linked with the operation of reverse vending machines which are in need of frequent cleaning to remove spillage of beverage leftovers which are more than often with a very high sugar content, resulting in sticky functional components and adherence between components, causing unnecessary wear and tear on functional components and drive units, causing reduced life of many components, as well as substantial risk of malfunction.

In the following, aspects of the present invention will be explained in their respective order by way of examples and by reference to the accompanying drawings, wherein the same reference numerals indicate the same elements, although as regards some elements, different reference numerals have been used for elements having same properties of functioning and for practical reasons.

BRIEF DESCRIPTION OF THE DRAWINGS

In the drawings:

FIG. 2a shows an exemplary embodiment of an essentially upwardly oriented storage or storage chamber according to the invention.

FIG. 40a is a partial view of a supporting device and a background area or panel, FIG. 40b is a variant of the background area or panel shown on FIG. 40a, FIG. 41a is a sketch of a first embodiment of a token reading means, FIG. 41b is a sketch of a second embodiment of a token reading means, FIG. 42 is a perspective view of a part of the view of FIG. 38, FIGS. 43-45 are perspective views of a token dispenser seen from below, from the side and above, and substantially from above, respectively, FIG. 46 is a block schematic diagram of electrically or electronically operative elements in a system incorporating the invention.

SPECIFIC DESCRIPTION

RVM Overview

Figure 1A:
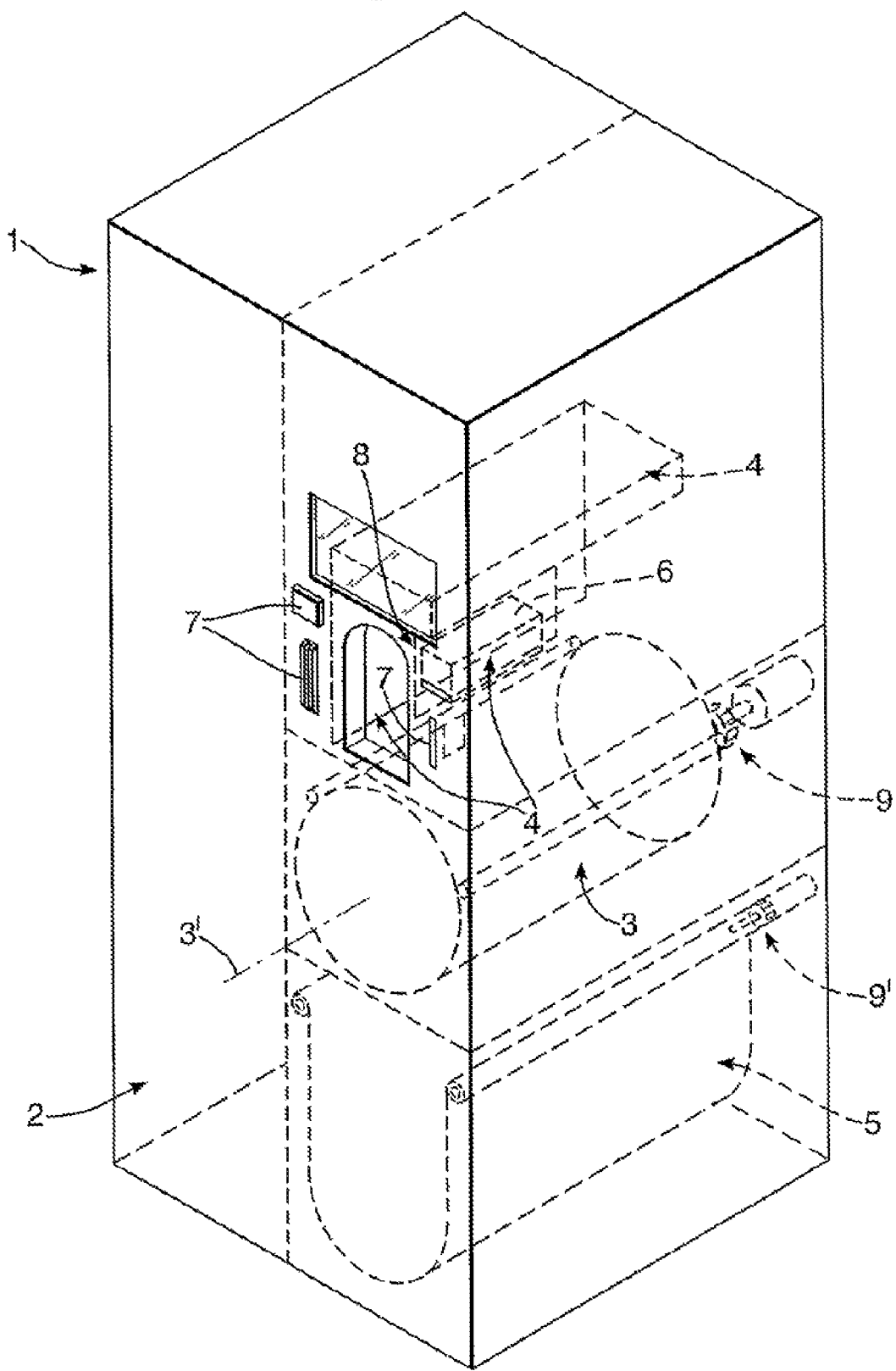
FIG. 1a shows in a perspective view, an exemplary mode of a reverse vending machine with object storage chamber; object supporting, rotating, sorting and conveyor means; camera-aided detector device; supplementary item/object collector means; token dispenser; token reader; safety apparatus; and drive means.
Figure 1B:
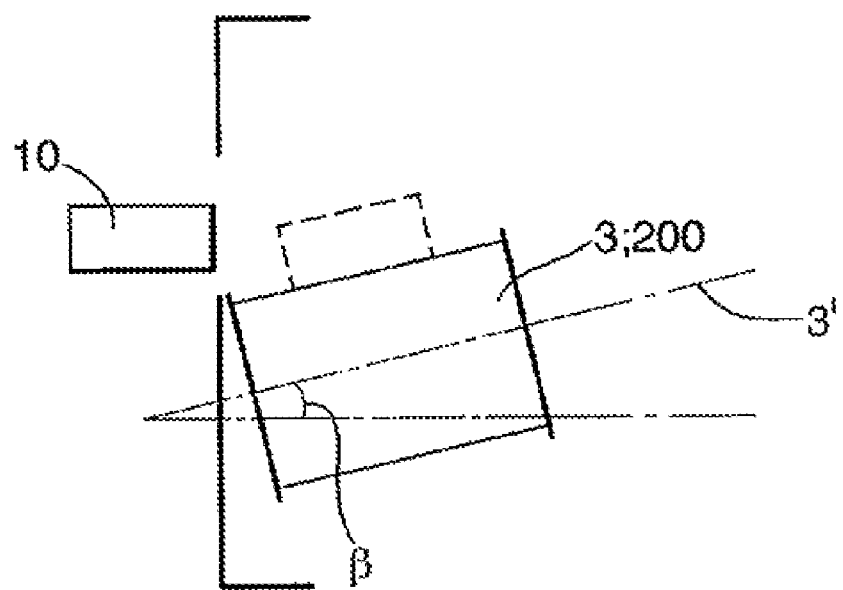
FIGS. 1b and 1c show the object rotating, sorting and conveyor means with its longitudinal axis tilted relative to the horizontal.
Figure 1C:
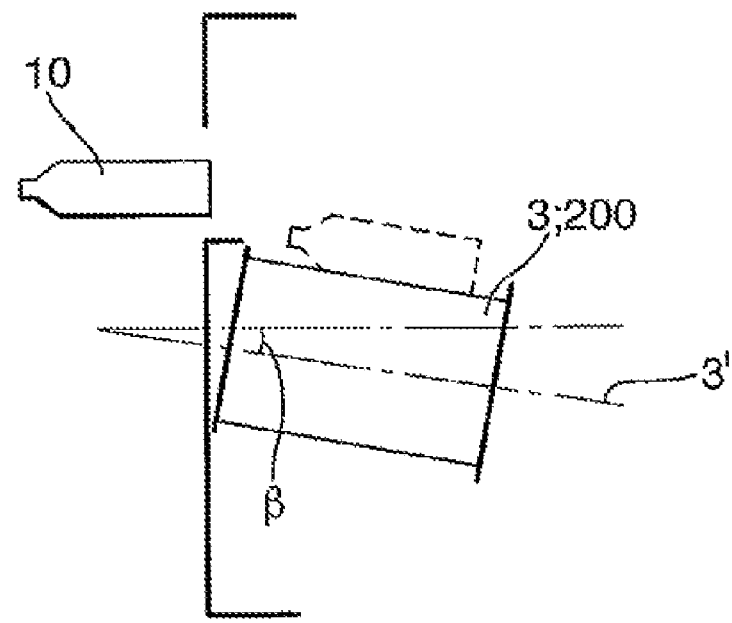
Figure 50A:
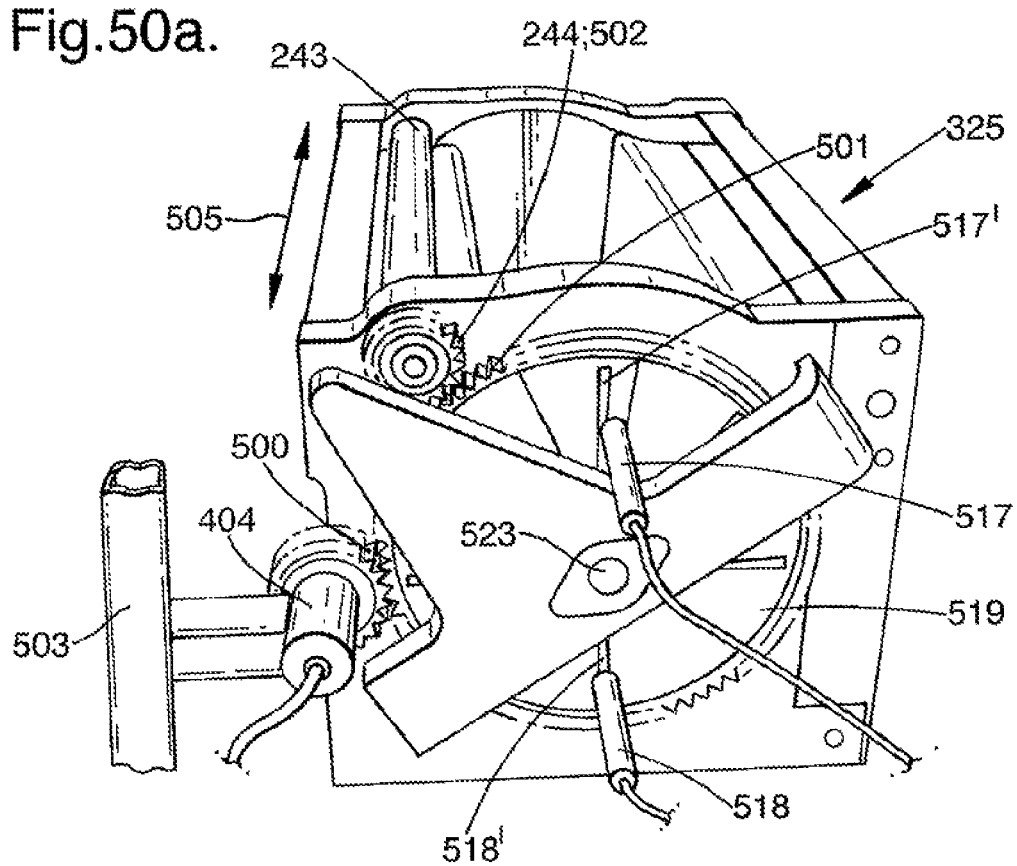
FIG. 50a shows the sketch of FIG. 47 with a first type of drum rotational position sensors indicated.
Figure 50B:
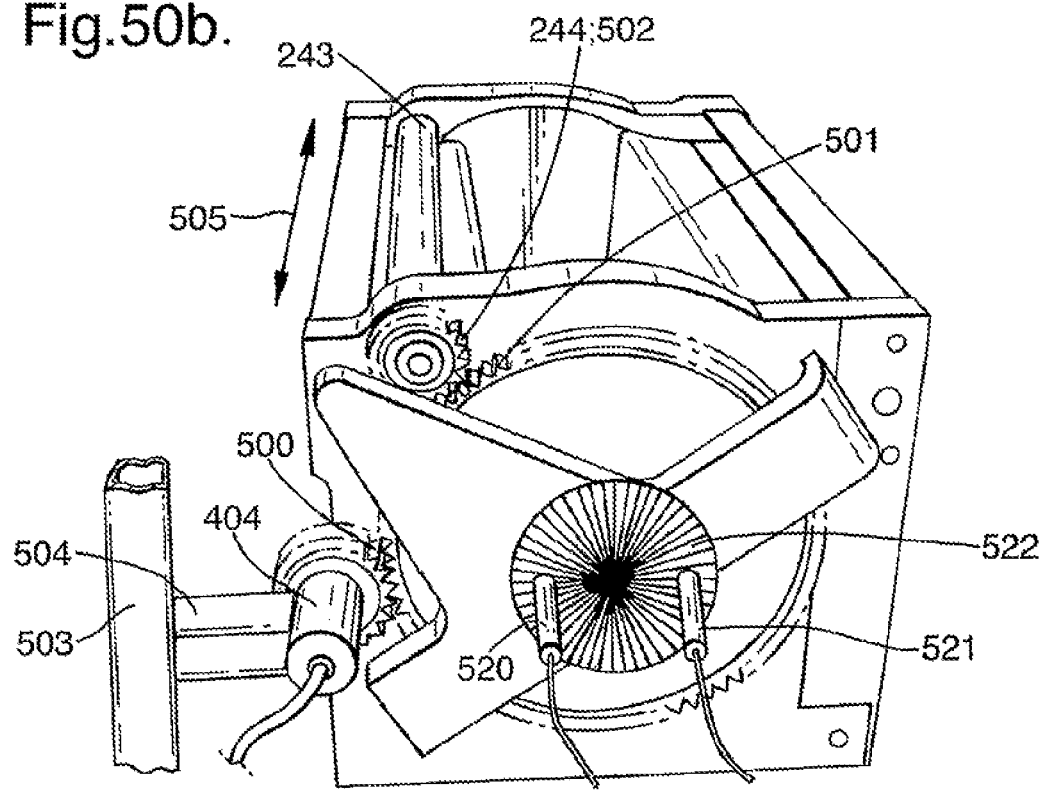
FIG. 50b shows the sketch of FIG. 47 with a second type of drum rotational position sensors indicated.
Figure 51:
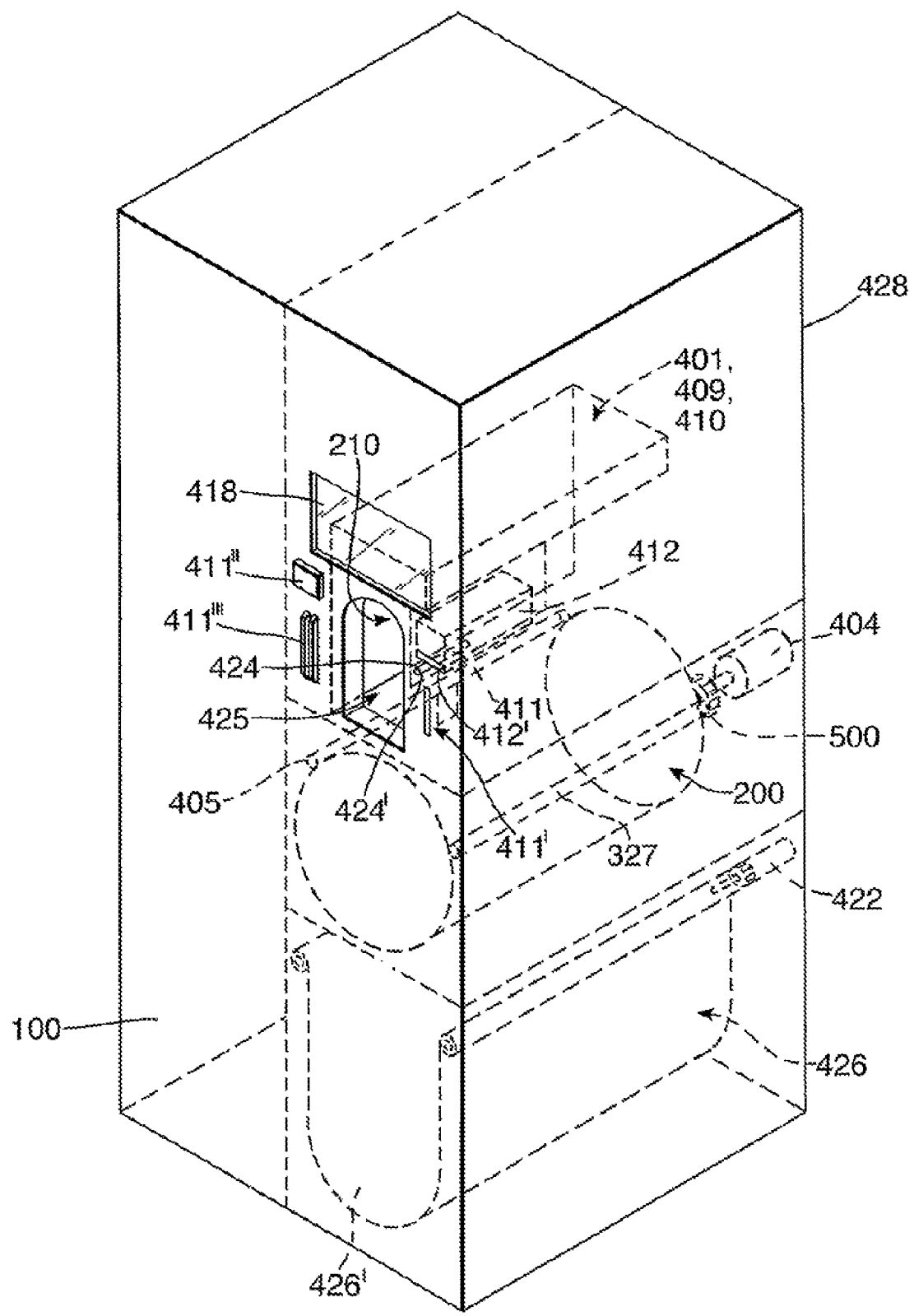
FIG. 51 shows in a perspective view a reverse vending machine with object storage chamber; object supporting, rotating, sorting and conveyor means; item collector means; token dispenser; token reader; and drive means.

FIG. 1a illustrates in an exemplary embodiment a reverse vending machine (RVM) 1 embodying main inventive aspects of the present invention, i.e. object storage chamber 2; object supporting, rotating, sorting and conveyor unit 3; camera-aided detector device 4; supplementary item/object collector means 5; token dispenser 6; token reader 7, safety apparatus 8, and drive means 9; 9'. The unit 3 (later denoted as 200) could have to have its longitudinal axis 3' horizontal or forming an angle $\alpha$ with the horizontal, yielding angle $\beta$ in the range $\pm 0°$ C.-30°, as indicated on FIGS. 1b and 1c. In the more detailed disclosure to follow, the operational means 2-9 just mentioned will for practical reasons be denoted by other reference numerals. Direction is also made to FIG. 51 showing the figure of FIG. 1a, however with more reference numerals inserted to identify location of some of the various operational means which are extensively disclosed in the disclosure to follow in connection with FIGS. 2-50.

Upwardly Oriented Storage

With reference to FIG. 2a showing a principle drawing of a storage chamber according to the present invention, certain features relating to the storage chamber and the principles of the invention will now be explained. In an advantageous embodiment of the invention, the storage chamber has an elongated and vertically oriented shape, with bottom and side walls, wherein the side walls are spaced apart, preferably sufficiently to allow for a side-by-side storage of a plurality of returnable items. The storage chamber has an in-feed opening in the lower part of the chamber, preferably arranged in one of the side walls, and feeding of the storage is obtained by driving returnable objects or items to be stored in the chamber into the storage chamber through the in-feed opening. By properly selecting the force by which the objects or items are driven into the storage chamber, and preferably by applying a forced pushing or thrust mode drive, objects/items already positioned in the storage chamber will be driven away from the in-feed opening and into the interior or back of the chamber until the chamber has been filled to the level at which the in-feed opening is located, and thereafter driven upwards by further objects/items being driven into the chamber.

In the illustration of FIG. 2a, the storage chamber 100 illustrating the invention is provided with a bottom part 120 and a side wall 130, 131 or 132, respectively, and an upper part 150. An in-feed opening 140 is located in the lower part of one of the side walls. To allow the storage space 110 to be safely emptied into removable transport container (not shown), e.g. a large box, for removal of returnable items 10 collected in the storage space or chamber 110, the bottom 120 can be made movable or removable, or one of the side walls 130 can be made movable such that items stored in the chamber or space 110 can be removed therefrom. As the chamber is being filled by returnable objects/items 10, if can be expected that the force applied to drive additional objects/items 10 into the storage through the in-feed opening 140 may give rise to some tension in the items already in the storage, due to other forces such as from friction or the weight of the stored items 10. Tension or friction may typically result in problems when trying to empty a filled storage space, for which reason a movable interior wall 132 is proposed, such that, in the case where the bottom part 120 is adapted to be opened to empty the storage space, the interior wall 132 may be moved in a direction away from the items 10 already located in the storage room. Thus, the tension is relieved and friction is reduced. This will allow for easy emptying of the storage. As the storage room becomes filled above the input opening, there is a risk that objects/items already positioned in the storage space may flow back through the in-feed or inlet opening. To stop such possible back-flow, a back-flow blocking arrangement 170 is preferably provided in the area of the in-feed opening.

The storage space exhibits a width dimension 111 being a multiple of the width dimension 11 of a returnable item for storage in said upwardly oriented storage, whereby a plurality of returnable items can be accommodated substantially or at least in part side by side in the interior space.

On FIG. 2a, a conveyor 200 for feeding items into the storage 100 is shown. Exemplary embodiments of such conveyor will be described with particular reference to FIGS. 8-24.

Although FIG. 2a illustrates a theoretical side-by-side stacking of returned items 10 lowermost inside the storage, practical tests have proved that the items in fact may be lying at least partly in a "criss-cross" manner, as indicated higher in the storage chamber. Thus, in general at least a partly "criss-cross" stacking will be present throughout the stacking in the chamber.

Figure 2B:
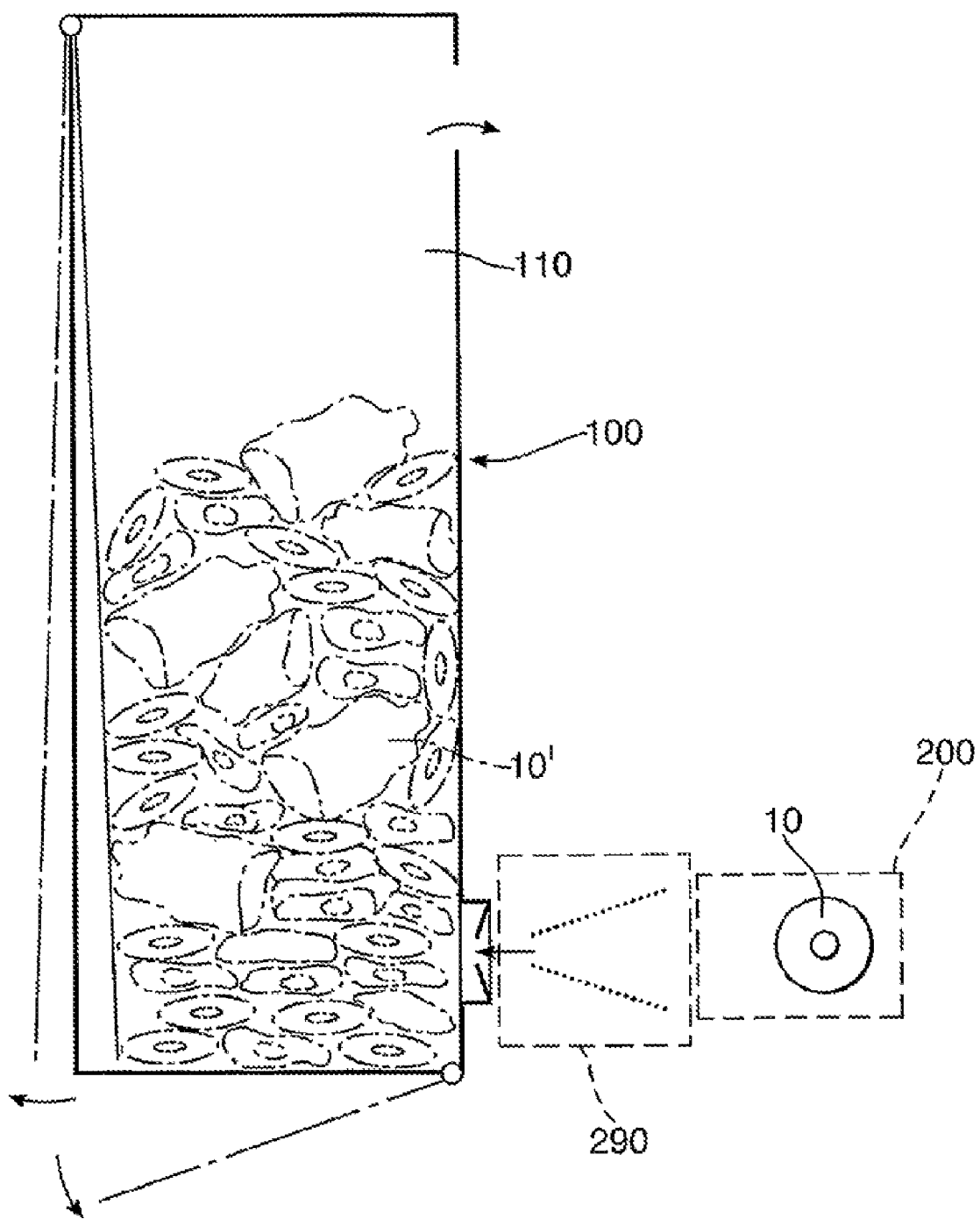
FIGS. 2b and 2c show the embodiments of FIG. 2a in association with a compactor.

FIG. 2b illustrates the use of an item or object compactor device 290 between the conveyor 200 and the storage 100. The compactor device 290 could be of any suitable type. In a particular exemplary embodiment it could be in the form of a set of spike-provided chains in a wedge-like arrangement in order to provide gradually flattened and punctured returnable items. The use of a set of flattening rollers acting as a compactor device could also be envisaged, as well as other types of well-known compactors.

Although the conveyor 200 is included upstream of the compactor 290 on FIG. 2b, it will be appreciated that in a particular embodiment the storage 100 and the compactor 290 could be able to work without the use of the conveyor 200. In an alternative, as generally indicated on FIG. 2c, a conveyor could be included, as indicated on FIG. 2b, or the conveyor needs not to be provided, or it could be operationally integrated with the compactor unit, the integrated unit being labeled 291.

Figure 2C:
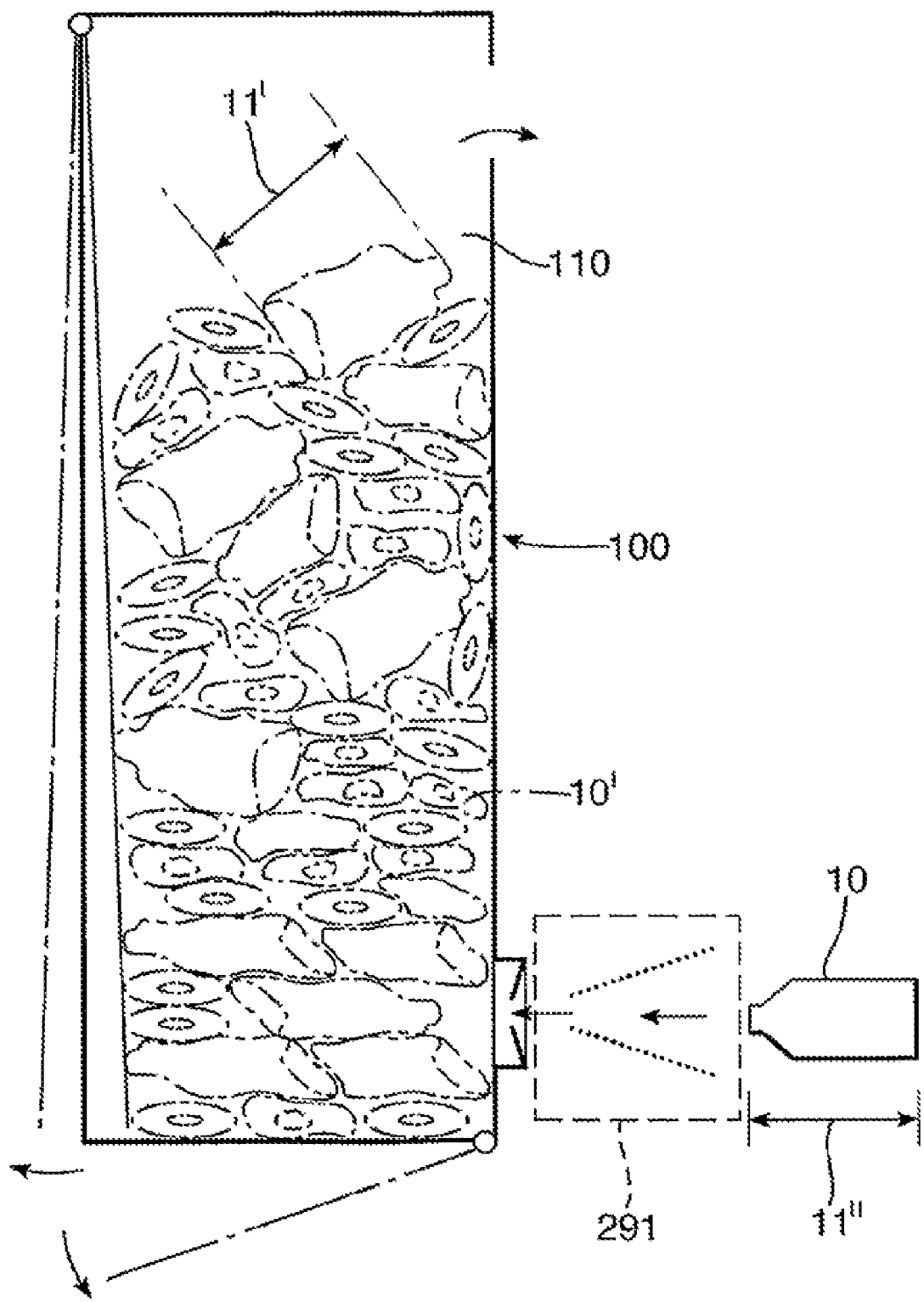

The compactor device 290 of FIG. 2b indicates that it receives returnable items with the longitudinal axis of the item 10 in question transverse to the in-feed direction. The compactor device 291 shown on FIG. 2c, is suitably of a type capable of receiving the returnable item 10 with its longitudinal axis in the in-feed direction. This implies however that the transverse dimension 111 of the storage should preferably be a dimension 11' related to the compacted item 10' which exceeds at least a maximum longitudinal extent 11" of an item 10 to be compacted.

It will be noted that when items are fed into the storage 100, after compaction, the orientation of the compacted items will be rather arbitrary or highly in a "criss-cross" fashion, irrespective of whether the items where fed into the compactor in a transverse or longitudinal direction.

Figure 3:
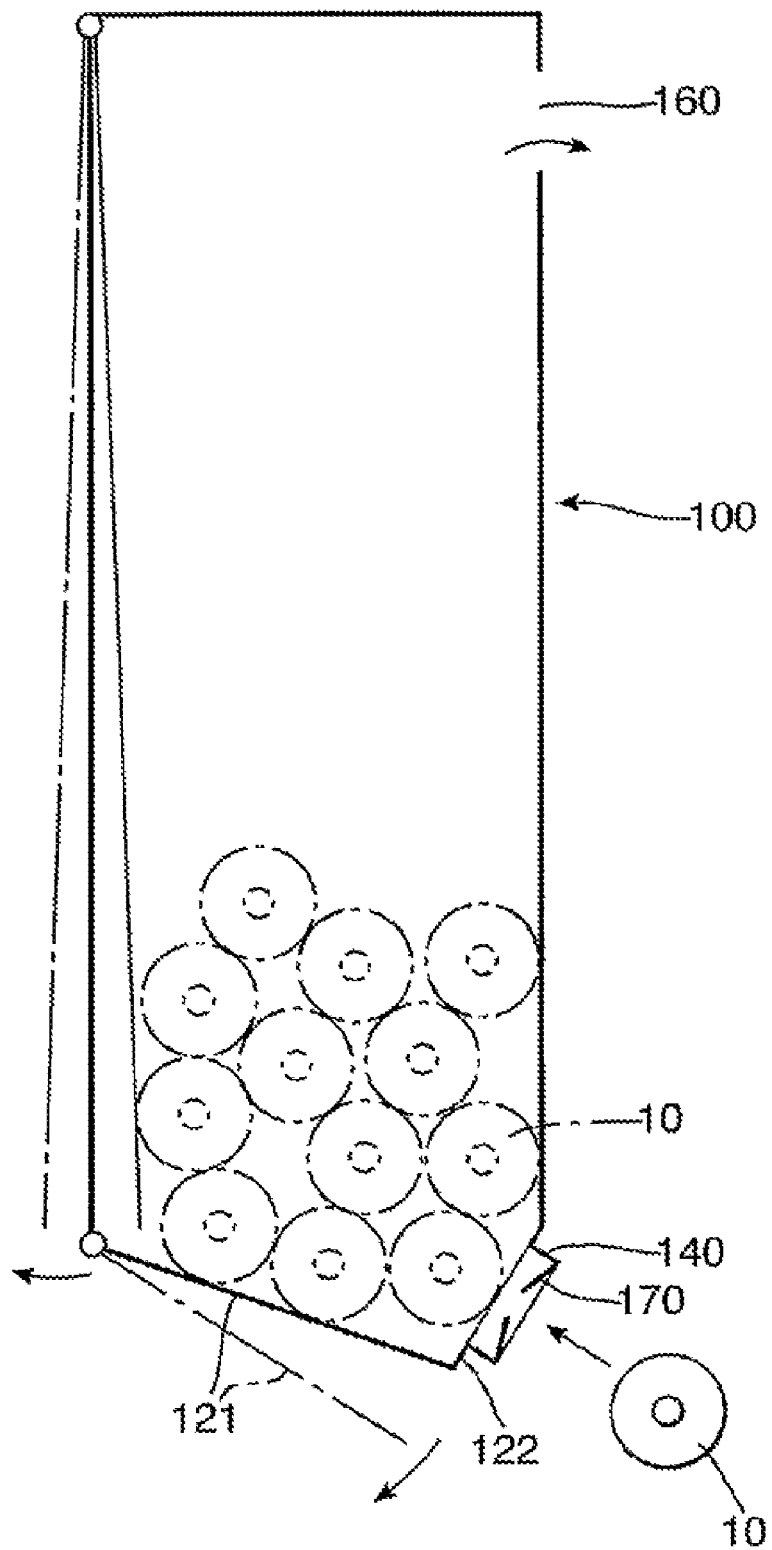
FIG. 3 is a further a principle drawing of a storage space or chamber for a storage facility according to the present invention.

Now, with reference to FIG. 3, an alternative storage chamber in-feed arrangement is explained. In the principle shown in FIG. 3, when compared with the principle shown in FIG. 2a-2c, the in-feed opening 140 is no longer positioned in a side wall, but rather in a bottom part 122 of the storage chamber 100. By this arrangement, items 10 to be stored will be provided with an upwardly directed movement or drive force component as a result of the in part upwardly directed drive component applied to drive items into the storage space. Similarly to what is shown in FIGS. 2a-2c, there may be provided several options for removing items stored in the storage space, such as by a movable or removable bottom part 121, or by a side wall arrangement as shown by 130, 131 or 132 in FIGS. 2a-2c. The storage chamber illustrated is adaptable to handle an overflow of stored items 10 by being provided with an overflow opening 160 through which excess object/items due to an overfilling of the storage space may exit from the storage chamber 110 and thereby relieve the storage chamber 110 from possible additional stress, as may result from further filling of the chamber by additional items 10 when the chamber has reached a point of maximum filling.

Figure 4:
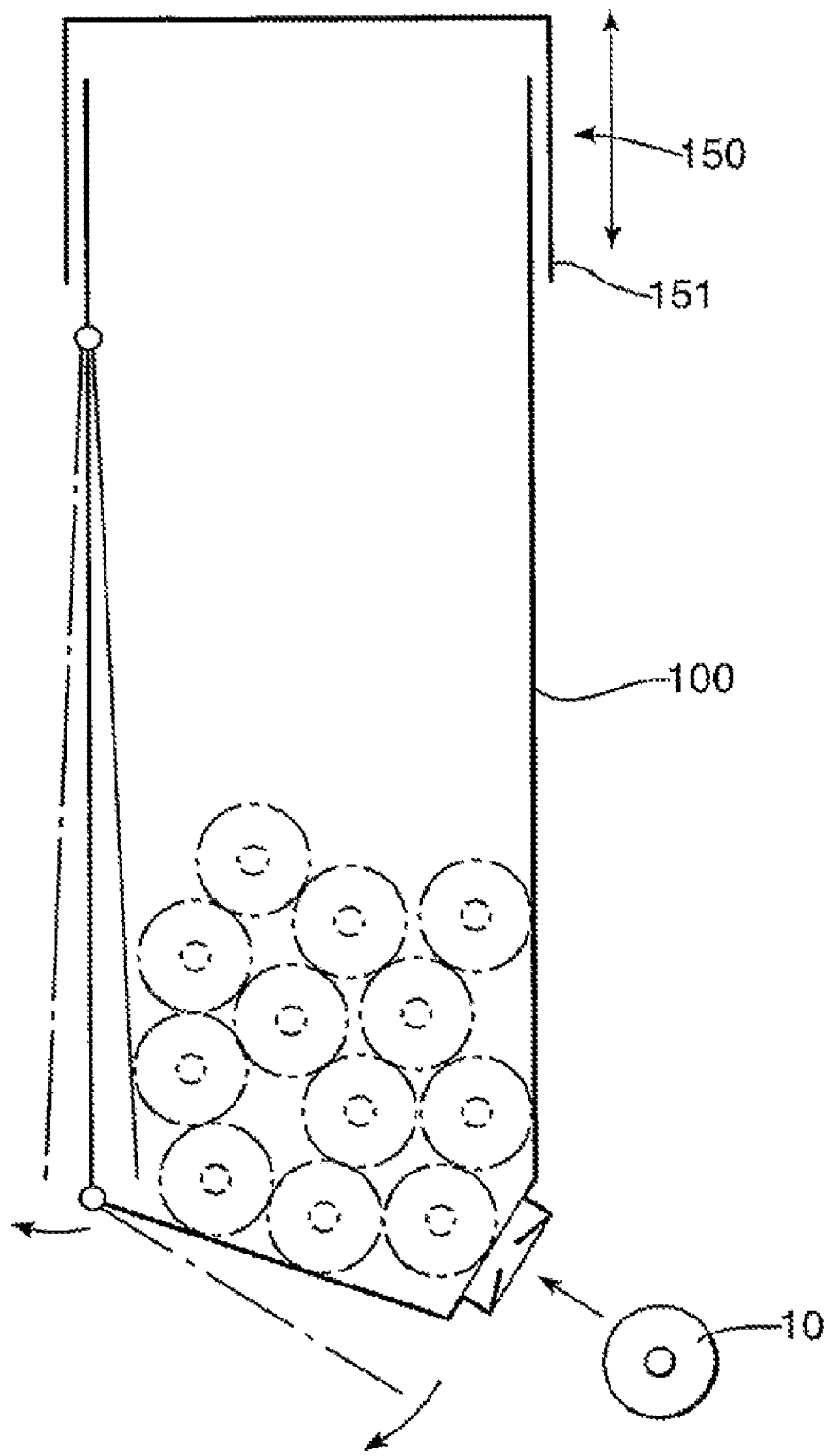
FIG. 4 is a principle drawing showing a first embodiment of an expandable storage chamber for a storage facility according to the present invention.

FIG. 4 illustrates in principle an expandable storage chamber for a storage facility according to the invention. The storage chamber may have any type of in-feed opening in its lower part as illustrated by FIGS. 2a-2c or 3 and is made expandable by a movable top section 151. Advantageously, by making the movable top section 151 from a light weight material, the driving force applied to a returnable object/item that enters the storage space through the in-feed opening will be sufficient to move the top section in an upward direction to allow an expansion of the storage chamber. The upward movement of the top section 151 can also be facilitated by mechanical, electrical, hydraulic or pneumatic means, to mention a few, such that the driving force applied to an object or item 10 that enters the storage space can be kept at a level that is independent of the design of or materials selected for the top section.

Figure 5:
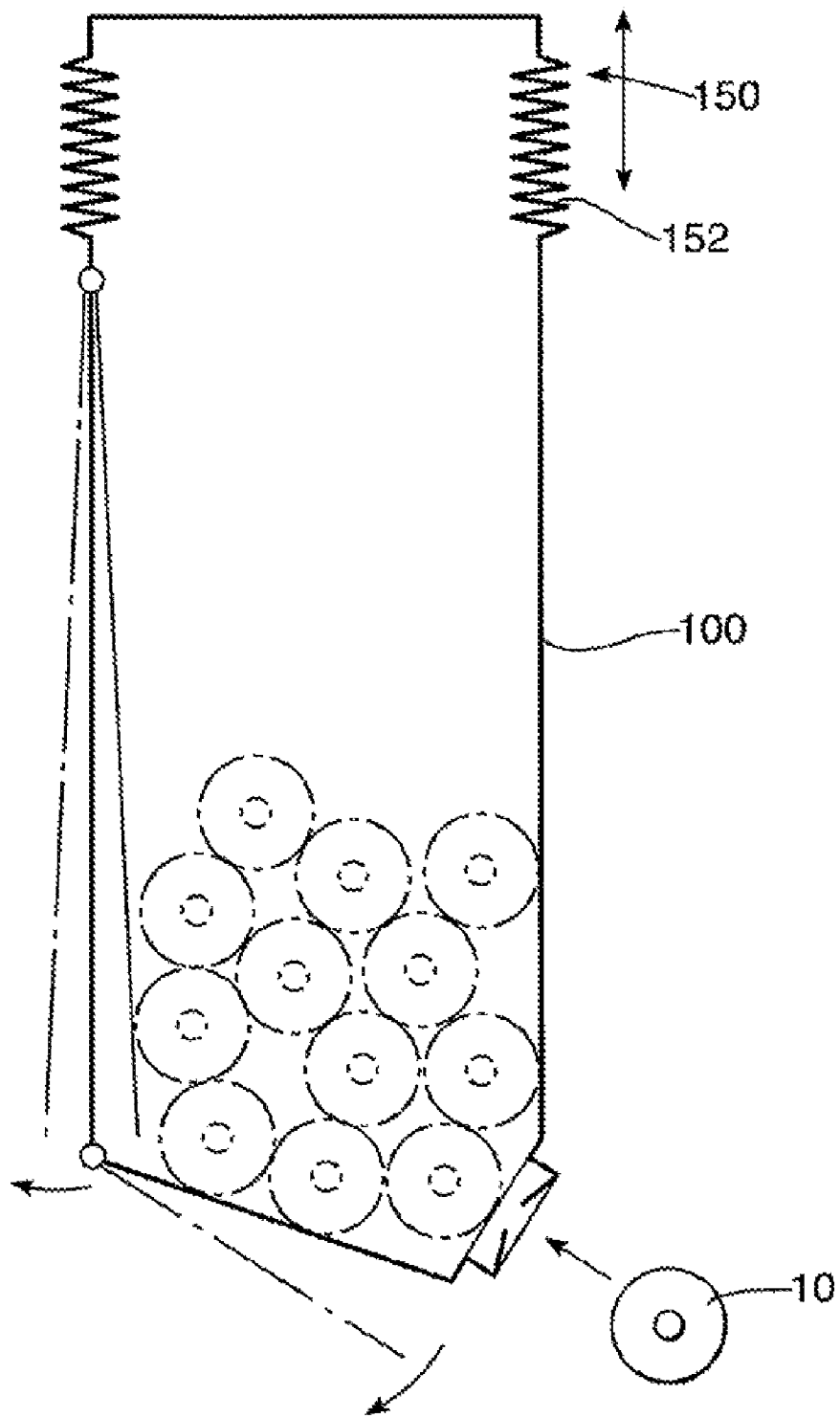
FIG. 5 is a principle drawing showing a second embodiment of an expandable storage chamber for a storage facility according to the present invention.

FIG. 5 illustrates the principle of another alternative for providing an expandable storage chamber, wherein the upper part 150 comprises flexible members that by an upwards movement of the upper part and the connected flexible members 152 will provide an increase of the storage space as the storage fills with returned items. Advantageously, as explained above with reference to FIG. 4, the top section and flexible members preferably are made from light weight material, such that the upward movement required for expanding the storage chamber may be facilitated by the force applied when driving an element into the storage space through the input in-feed opening. A vertical movement of the upper section and the flexible members 152 can be provided by other means, such as electrical, mechanical, hydraulic or pneumatic, to mention a few.

Figure 6:
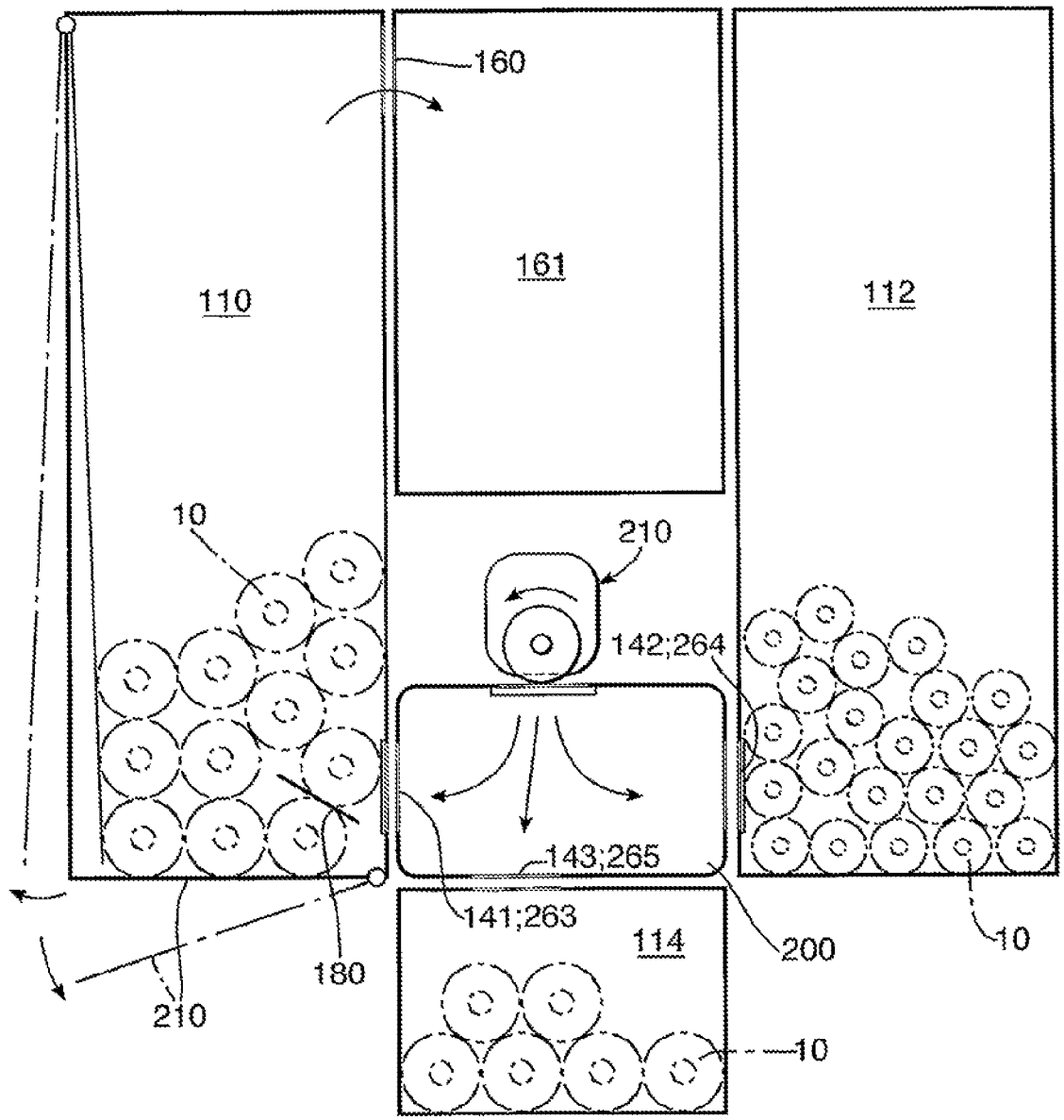
FIG. 6 is a principle drawing showing an exemplary layout of a storage facility according to the present invention having multiple storage chambers.

Reference is now made to FIG. 6, which provides an illustration of the principles of the present invention in a possible layout having multiple storage chambers. The exemplary storage facility illustrated in FIG. 6, comprises as many as three storage chambers 110, 112 and 114, respectively, each having a respective in-feed opening positioned for being in communication with a conveyor 200 being capable of receiving an item in an input receiving area 110 and conveying the received item 10 to a selected one of in-feed openings 141, 142 and 143 (see also reference numerals 263, 264 and 265 with respect to the embodiments of FIGS. 20-24 and 32) of the storage chambers 110, 112 and 114, respectively. The storage chamber 110 is provided with a cooperating supplementary storage space 161 in communication with the first storage chamber 110 by overflow openings 160 in the upper part of adjacent side walls. Storage chambers 110 and 112 have respective in-feed openings 141 and 142 located in respective side walls in their lowermost parts, and are dimensioned appropriately to provide a filling of the respective chamber in an upwardly direction when the appropriate item is driven into the chamber through the respective in-feed opening. In the example of FIG. 6, storage chamber 110 has been provided with a deflector 180 located inside the chamber and at an appropriate distance from the in-feed opening 141 to provide an upwardly directed force component to objects/items being driven or forced into the storage space in a specific direction, although the driving force may already have an upwardly directed drive component. Thus, the upwardly directed drive forces exerted on the item 10 as it enters the chamber may become more consistent, and also less dependent on the shape and nature of other items 10 already located in the storage. Advantageously, the deflector can be moveable, such as by being tiltable or even removable, to allow easy and complete removal of all items held in the storage chamber when the storage chamber is to be emptied.

Figure 7:
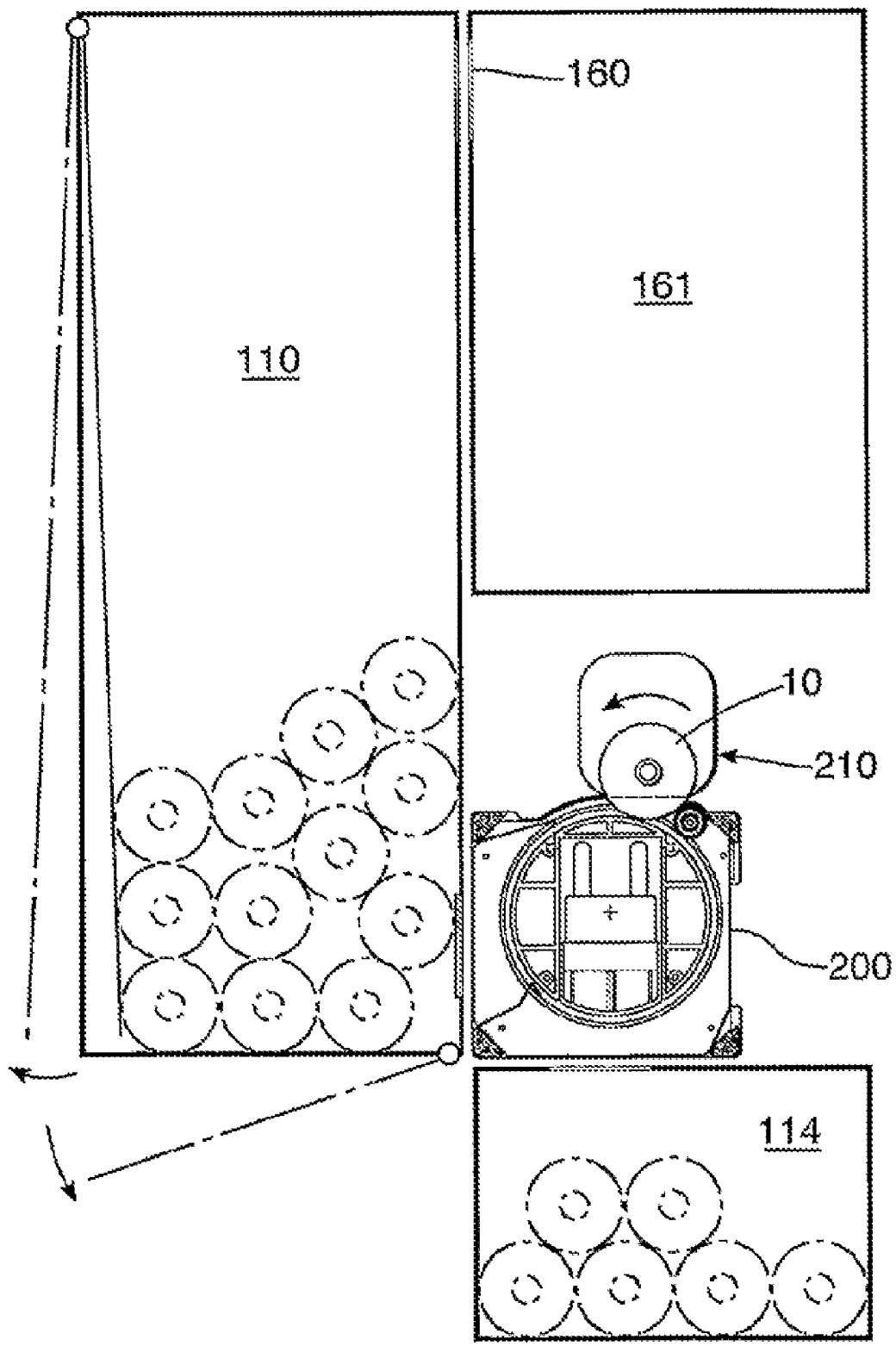
FIG. 7 is a principle drawing showing an exemplary possible layout of a storage facility according to the present invention having multiple storage chambers and a drum type conveyor unit.

FIG. 7 shows a simplified valiant of the layout depicted in FIG. 6, and with a conveyor of a drum type that provides a highly compact facility for receiving, transporting, sorting and storage of returnable items. The arrangement shown in FIG. 7 is capable of sorting, conveying and storing large quantities of returnable items while requiring a very small floor space, by employing the compact conveyor and sorter 200 and the vertically oriented storage system of the present invention. Thus, the need for use of a separate lifting arrangement to fill from a low level a tall storage space is being eliminated, such that in a practical implementation and embodiment the storage chamber may extend from any level and up to a ceiling above as desired, which is highly beneficial in a small business environment, like in a convenience store or a gas station, where available floor space typically is quite limited. The FIG. 7 embodiment provides for the additional storage or item collector 114 below the conveyor and sorter 200. In the case of receiving returnable items like bottles and cans, glass bottles could e.g. be dropped by gravity into the collector 114 when the conveyor and sorter 200 has brought such a type of item to be just above a receiving opening of the collector 114.

Figure 8:
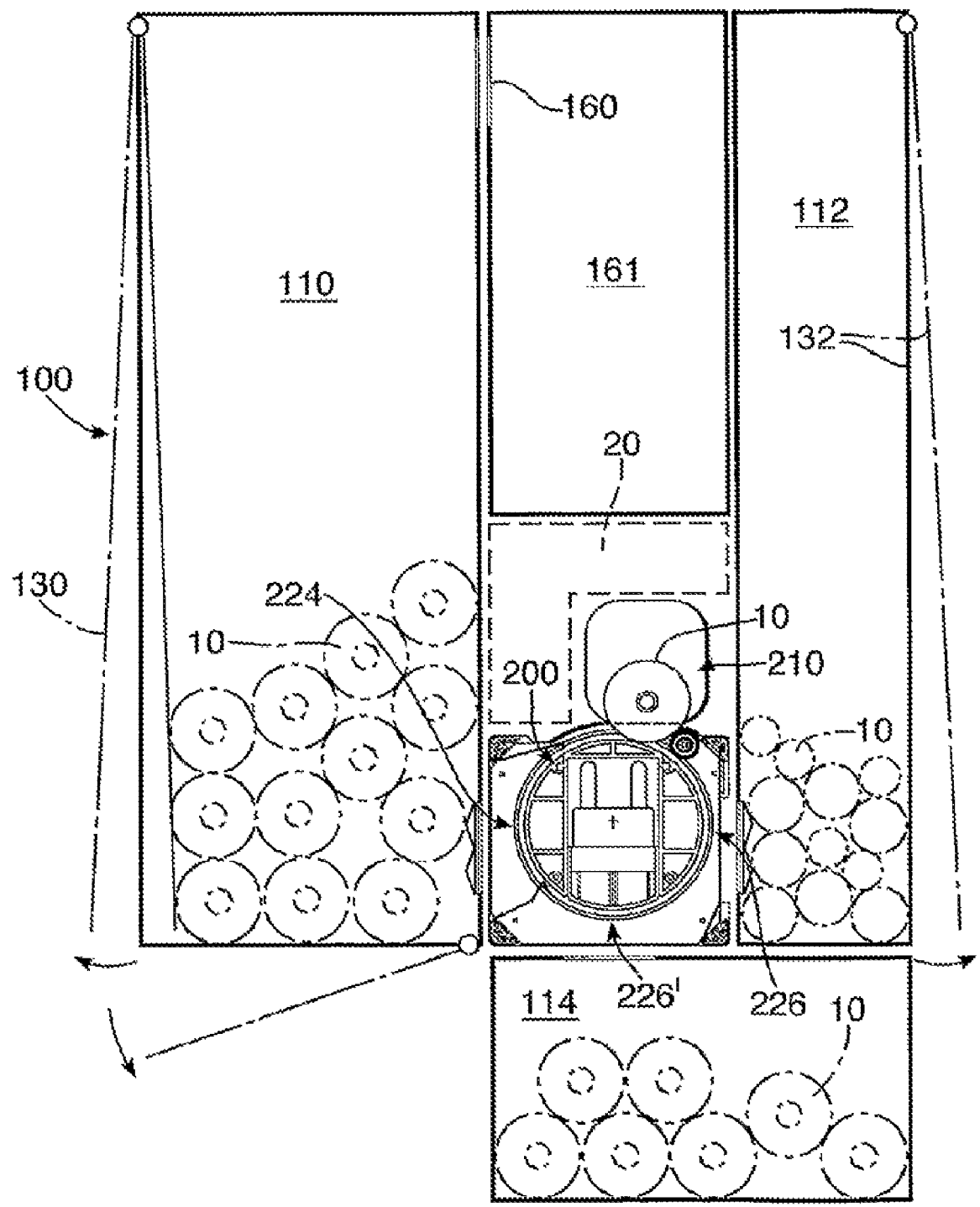
FIG. 8 is a principle drawing showing a possible layout of a storage facility according to the present invention having multiple storage chambers, a conveying and sorting means, and means for reading information from, or detecting the type of, returnable item or object being positioned in an input receiving area.

FIG. 8 illustrates a further exemplary embodiment layout of the present invention that utilizes a highly compact drum based conveyor with as many as three different storage chambers, denoted by 110, 112 and 114, for storing different types of returnable items 10. The conveyor 200 is adapted to receive items 10 in an input receiving area 210, and to move and output the item, based on certain criteria and a decision made by a controller that operates a drum drive unit, at either a first output 224 for driving the item into a storage space 110, or to a second output, which is either the second output 226 for driving a received item 10 into the related storage chamber 112, or the second output 226' for, in this particular embodiment, allowing also gravity to assist in moving the item 10 from the conveyor to the related storage space 114. The storage space 114 is particularly useful for items to which a relatively high driving force should not be applied, such as for example fragile glass items or heavy items, such as bottles that carry significant amounts of liquid contents, or for other reasons are found unsuitable for being driven into one of the upright storage spaces 110 or 112 for elevated storing above the level of the input receiving area.

Although three storage chambers 110, 112 and 114 are shown on FIG. 8, in a practical embodiment with a rotary conveyor and sorter as depicted, only two storage chambers will be used e.g. 110, 112; 110, 114; or 112, 114 with the related outputs 224, 226; 224, 226; or 226; 226'.

In the layout of FIG. 8, the storage chamber 110 is provided with an overflow opening that provides communication to a supplementary storage chamber 161. The facility layout shown provides a highly compact design, augmented by the use of the compact drum type conveyor means. For a person who is to deposit a returnable object/item at the facility, there is conveniently an input receiving area 210 located as shown in the lower half of the facility. The facility includes a returnable object/item recognition unit 20, which can include, or be connected with a controller for controlling the operation of the conveyor 200. The recognition unit 20 can be of an optical or acoustic type, or employ other or supplementary technology, such as magnetic, mechanical or electrical sensing to determine the type of returnable object/item 10 that has been placed in the input receiving area 210, or to read information or identifying features (e.g. bar-code) carried by, or located on, the item 10. A preferred embodiment of a recognition unit is further disclosed in connection with FIGS. 25-42, and 46. In particular, with regard to the storage chambers 110; 112, by employing a movable side wall 130; 132 or a removable storage chamber 114, the storage chamber 114 can be extended to fill the unused space shown to appear below the first storage chamber 110. To facilitate easier filling of the upright oriented storage chambers 110 and 112, a deflector 180, such as is shown, in FIG. 6, can also be included.

Rotary Drum Type Conveyor Means

Figure 9:
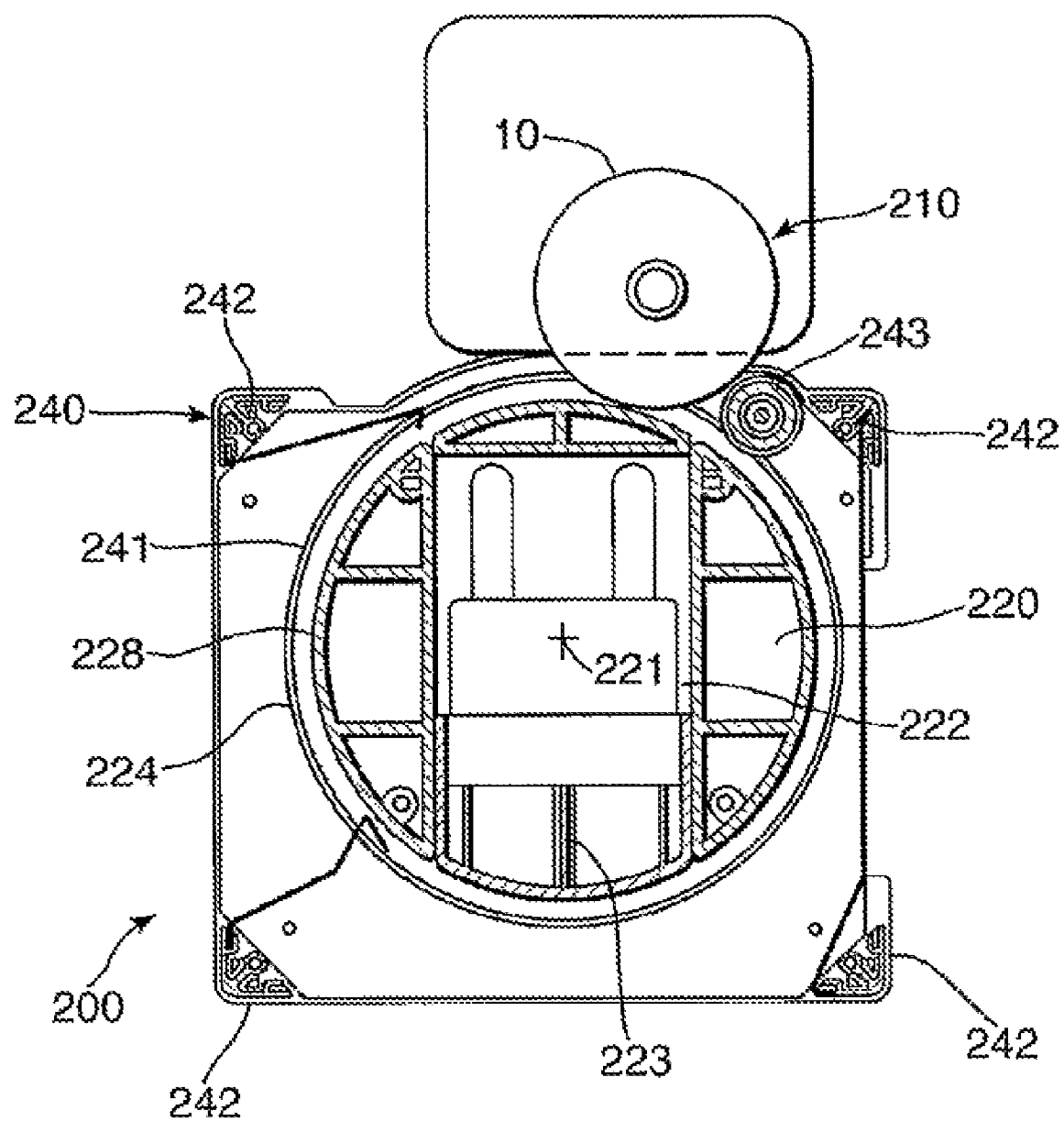
FIG. 9 is a partial sectional view of a drum type conveyor for a storage facility according to the present invention, being positioned in a first rotational position.

Reference is made to FIG. 9, to explain the drum type conveyor of the present invention. The drum type conveyor includes a drum shaped element that is rotary about a central, longitudinal axis of rotation 221. A substantially rectangular and elongate recess-like space or cavity, being open at the peripheral area of the drum, is provided in the drum, for holding an elongate movable element which can be retracted and advanced, the movable element having an outer surface that in the advanced position preferably becomes substantially aligned with an outer surface of the drum. In the accompanying drawings, the movable element is denoted by the numeral 223, and the space or cavity in the drum is denoted by reference numeral 222. The rotational capability of the drum 220 is obtained through use of bearings positioned in a region at each end of the drum, and positioned on the axis of rotation 221. A part of the structure as shown in principle for example in FIG. 8, such as a cabinet, can be adapted to hold the bearings in place, thereby allowing the drum to rotate with its outer surface 228 in proximity to the input receiving area 210 which is made to coincide with an inlet opening 425 (see FIG. 51) in the cabinet 250 (see FIG. 18), 428 (see FIG. 51). As an alternative, as shown in FIG. 10 and in other drawing figures, the drum 220 may be positioned in a frame 240 to form a conveyor assembly for easy conveyor assembly removal for convenient conveyor cleaning, test, maintenance and replacement.

To ensure proper alignment and good fixation of the conveyor unit when located in a storage facility according to the invention, the frame 240 is suitably adapted to match a receiving frame 251 (FIG. 18) that preferably is part of a cabinet 250 (FIG. 18), 428 (FIG. 51), and which facilitates any of the possible layouts of a storage facility, as exemplified by several of the previous figures.

Figure 10:
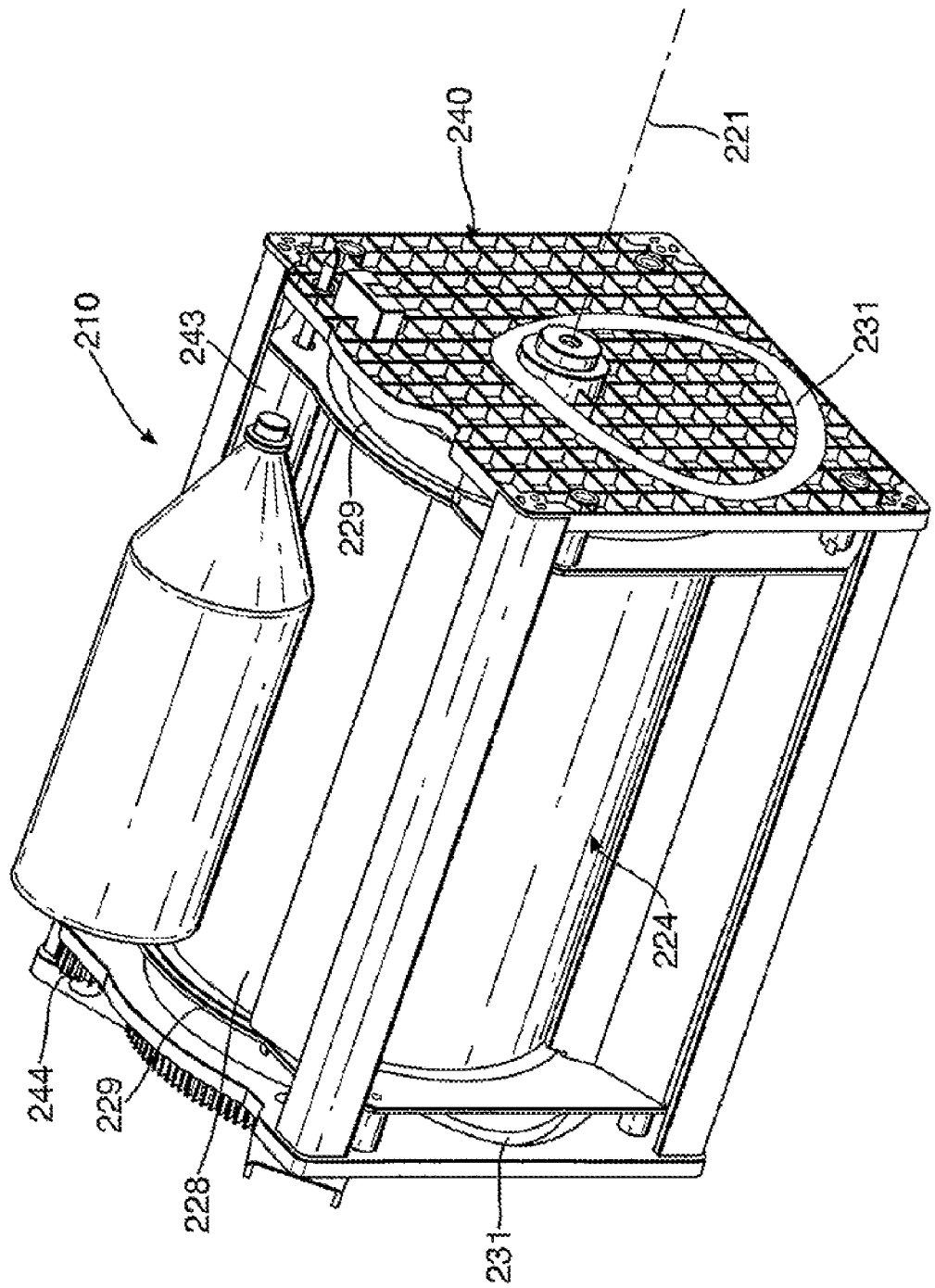
FIG. 10 is a perspective view of the drum type conveyor shown in FIG. 9.
Figure 14:
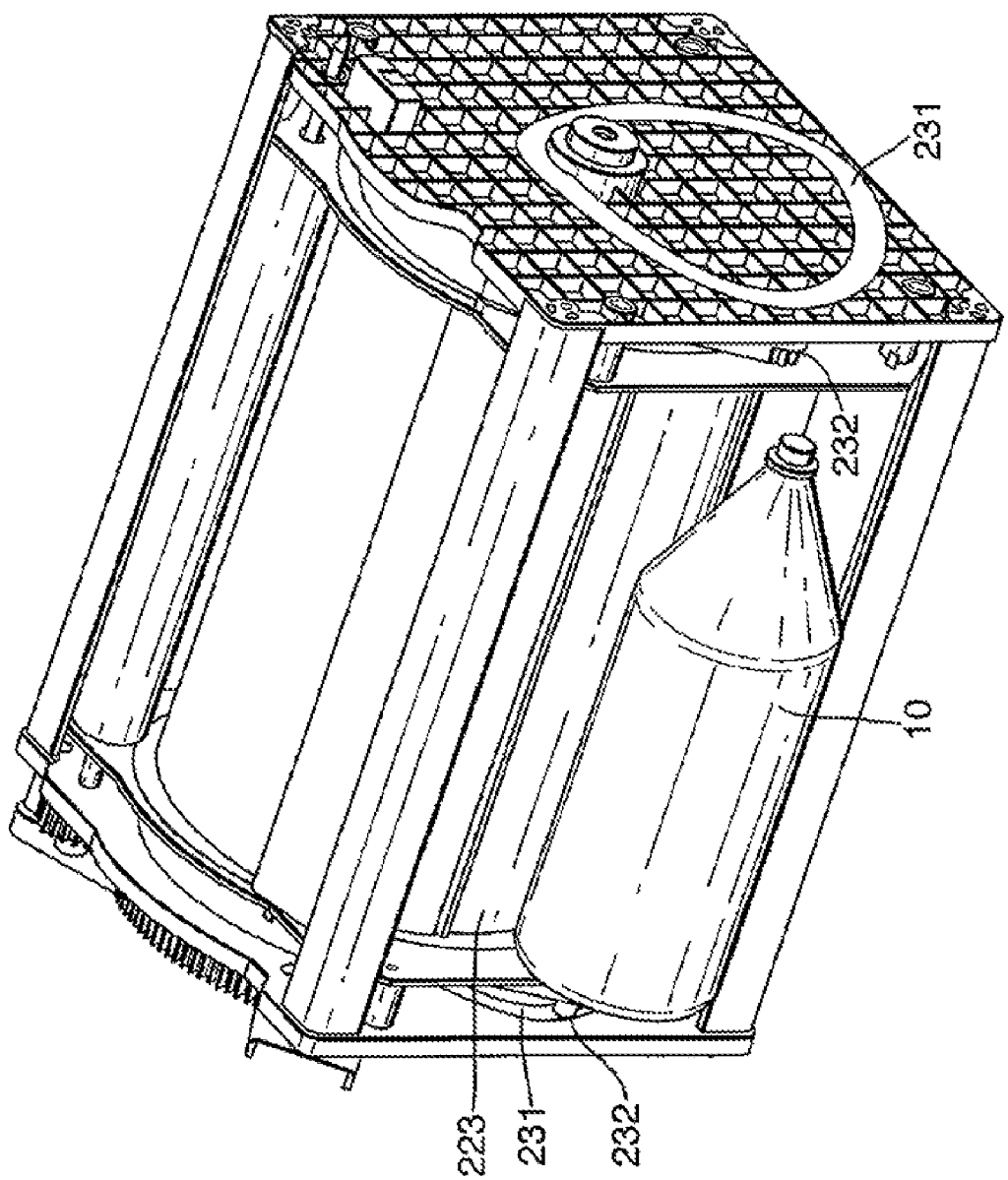
FIG. 14 is a perspective view of the positional state of the drum type conveyor of FIG. 13.
Figure 16:
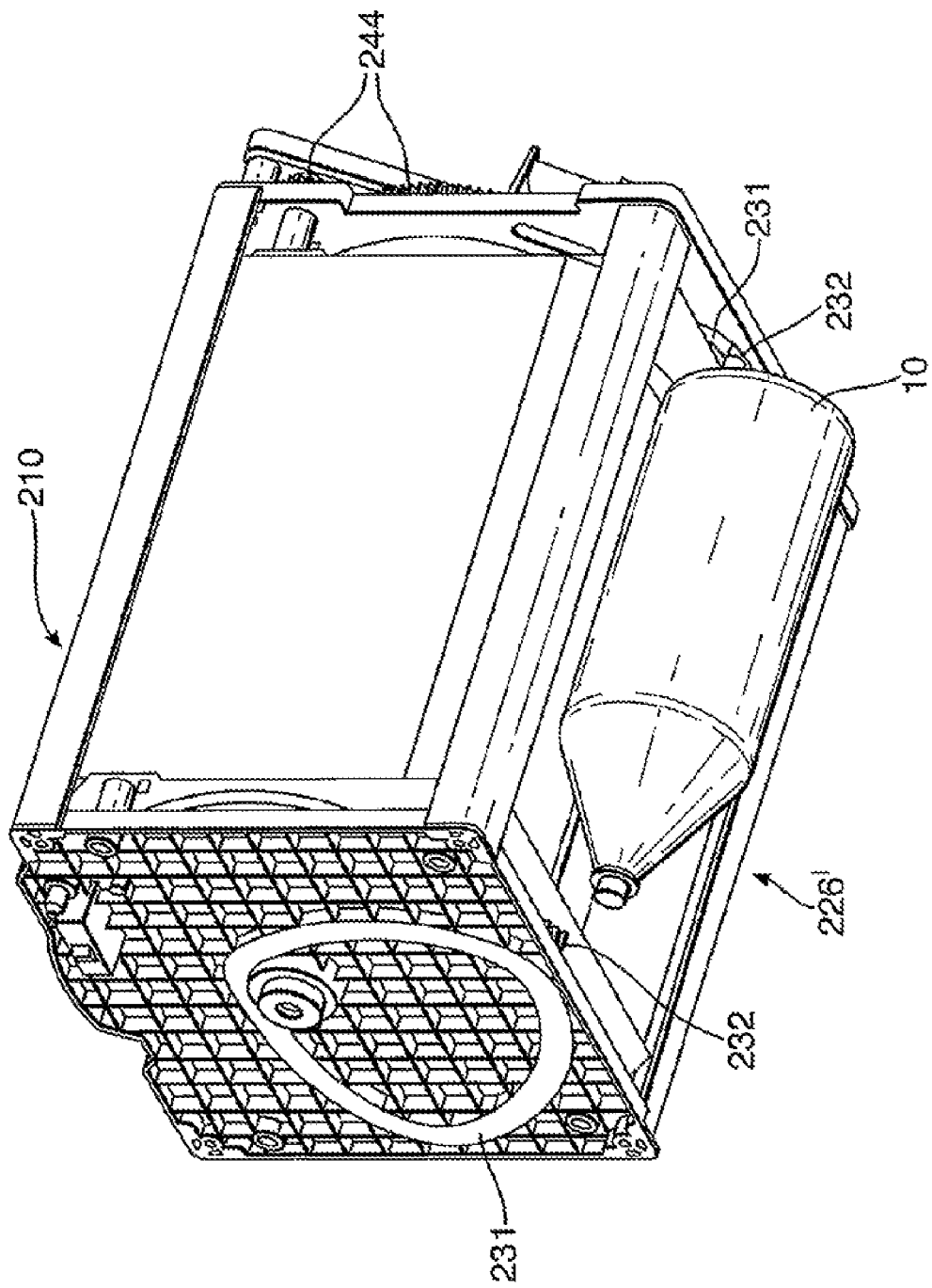
FIG. 16 is a perspective view of positional state of the drum type conveyor of FIG. 15, as seen partly from below.

Preferably, as shown in FIG. 10, 14 or 16, the moveable element 223 is driven by way of a moveable element drive means comprising a tappet or a roller 232, being attached to the moveable element 223, that follows a track 231 located proximal to an end of the drum and being stationary in respect of the drum. By providing a tappet or roller 232 on each side of the moveable element, made to engage with respective stationary tracks 231 located proximal to respective ends of the drum, a balanced driving force can be applied to the moveable element by the rotation of the drum. Thus, only the drum will require a drive for the assembly to operate as described here, as the moveable element will be driven by the movement of the drum relative to the stationary track. The shape of the track, i.e. the distance of the track from the axis of rotation of the drum, controls the position of the tappet or roller 232, and, hence, the position of the moveable element, in a radial direction with respect to the drum center axis. The track is a single, continuous track 231 followed by the tappet or roller means 232.

In FIG. 9, the drum 220 is shown in a first rotational position with the movable element in an advanced position and pointing downwards, and with a returnable object/item 10 entered into the input receiving space or area 210 to be placed on an upward facing region of the outer circumferential surface 228 of the drum 220. In a preferable embodiment, the drum type conveyor includes an elongate roller 243, or other means to allow rotation of the item while keeping the item in the input receiving area, to facilitate a rotation of a returnable object/item 10 resting on the drum surface 228 as the drum 220 is put into rotation about its axis of rotation 221. In particular, when the returnable item is provided with a readable code for identification of the item or for providing specific information about the container, rotation of the object/item 10 will often be required to position the part of the object/item 10 carrying the code such that it becomes readable, for example by use of a reader or recognizing device 20 located to observe the input receiving area, as shown in FIG. 8. The drum type conveyor has also a guide 241, e.g. a curved plate member, that extends from the area 210 to the output 224, as will be further explained in connection with FIG. 15. Further guides 241, e.g. as also shown on FIG. 15, could extend from the area 210 down to the output 226'.

FIG. 10 depicts in a perspective view the drum 220 in the first rotational position as shown in FIG. 9 and with the returnable item 10 resting on an upwardly facing part of the drum circumference. In the embodiment of FIG. 10, the conveyor is provided with a roller driving 244 means for driving the roller 243 in conjunction with driving of the drum, such that the surface velocity of the roller 243 is in a range of a velocity of a rolling surface 228 of the drum when rotated. Preferably, the roller driving means 244 comprises a gear drive arrangement that mechanically provides a rotation of the roller 243 by the rotation of the drum 220. Movement in an axial direction of a returnable object/item 10 being positioned in the input receiving area and resting on the drum 220 and roller 243 is in part restricted by end walls 229 associated with and located at each end of the drum 220, and in part by elements 242 that constitute the frame 240. Depending on the design of the means for driving the movable piston-like element 223 between its retracted position and its advanced position, the conveyor shown in FIG. 10 can be provided with a single output 224, corresponding to only one particular angular drum rotary position, or with a second output at a different angular rotary position of the drum.

Figure 11:
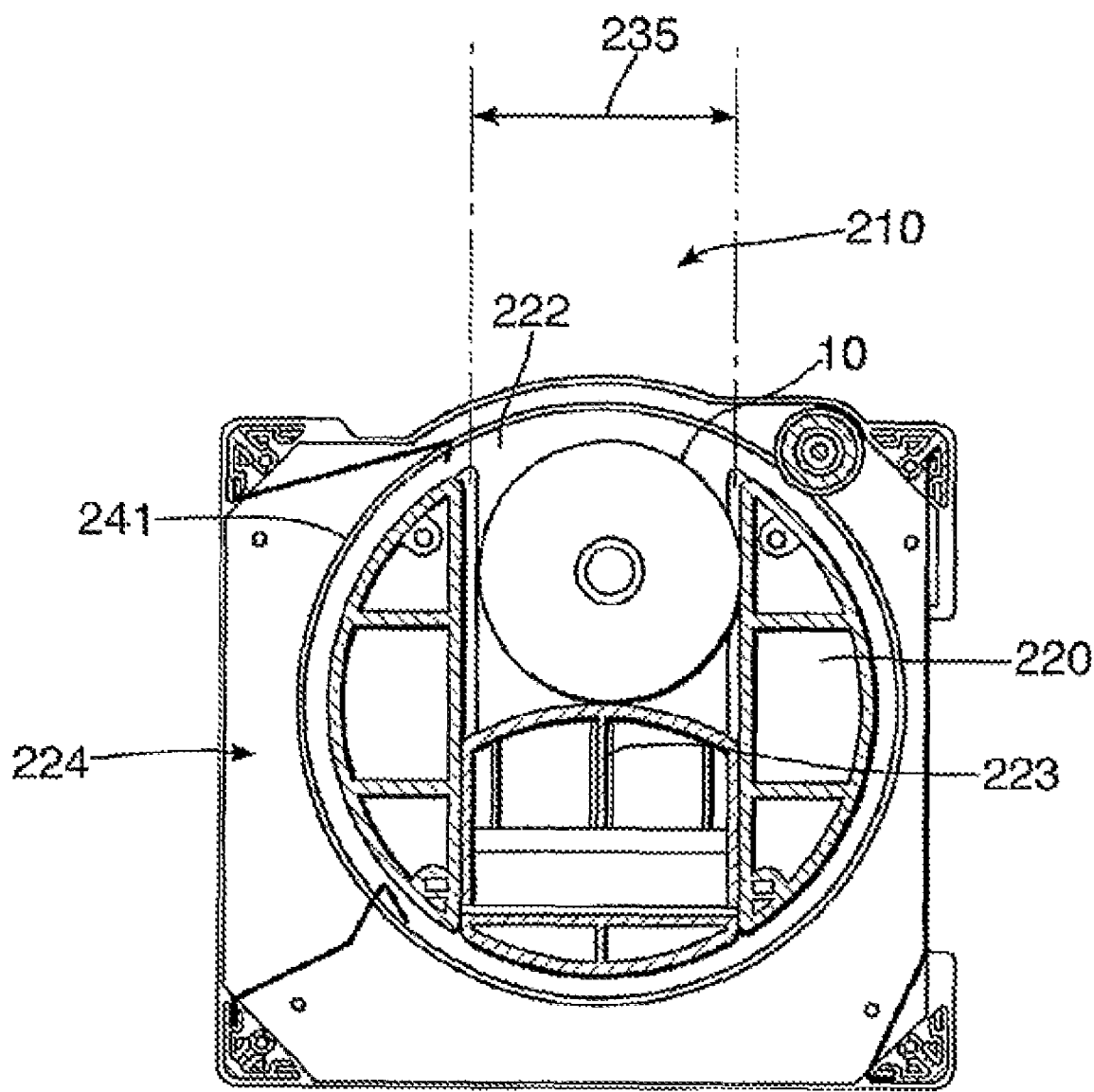
FIG. 11 is a partial sectional view of an embodiment of a drum type conveyor for incorporation in the present invention, the drum being in a second rotational position with a piston like plunger element in a retracted position.

In FIG. 11, the drum 220 is shown in a second rotational position with the space or cavity opening in the drum facing the input receiving area, and with the movable element 223 moved to the retracted position. This has thereby allowed the returnable object/item 10, shown in FIG. 9 as resting on the circumferential drum surface 228, to fall into the recess-like space or cavity 222, as the drum is rotated to arrive at the second position after rotation from the first position, and be contained by the drum 220. The same situation is also shown in the perspective view of FIG. 12, which shows parts of interior side walls of the space 222 and the drum end walls 229, which contribute to restrict a movement of the returnable object/item 10 such that it may not go beyond the space provided by the cavity 222.

Figure 12:
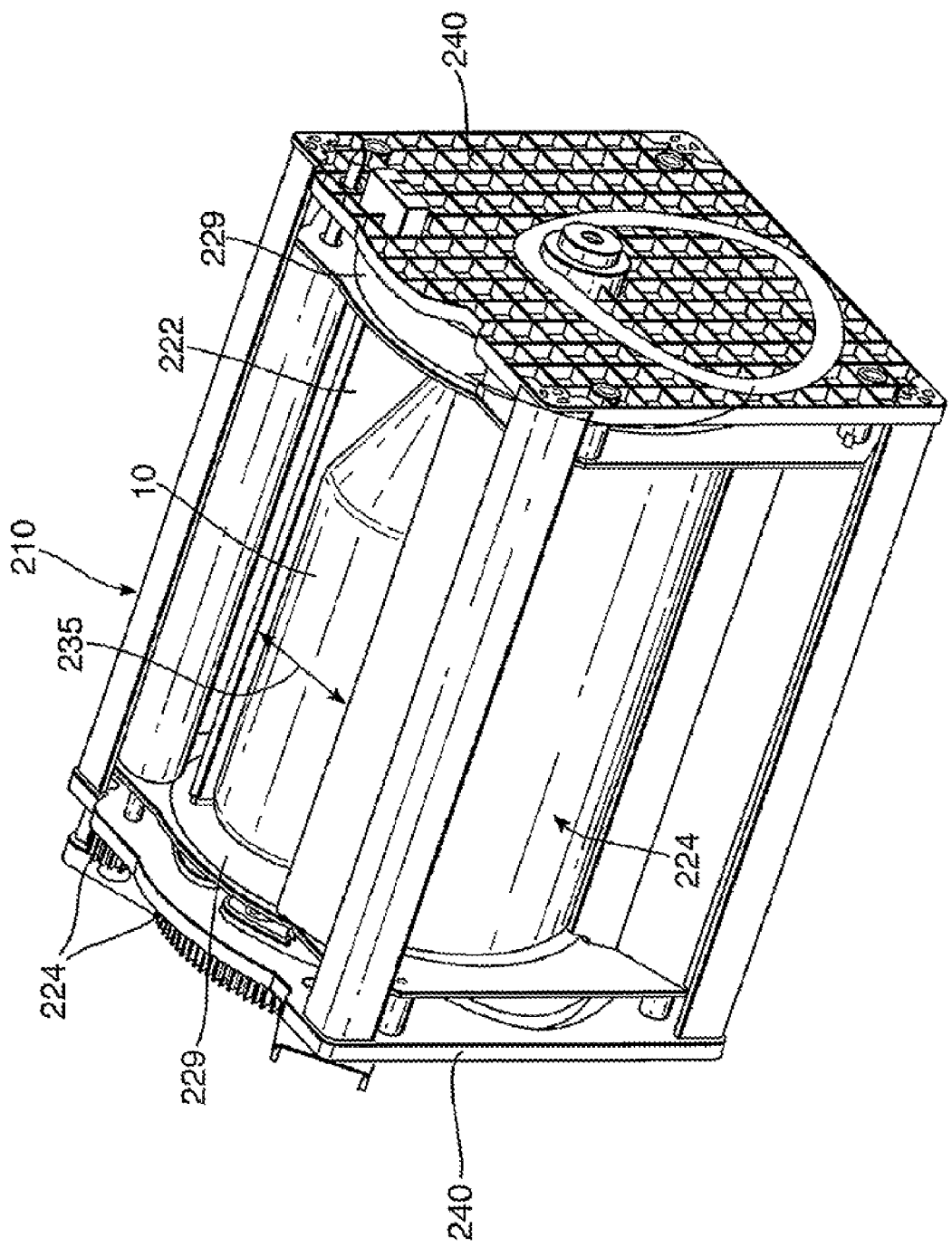
FIG. 12 is a perspective view of the conveyor of FIG. 11.
Figure 13:
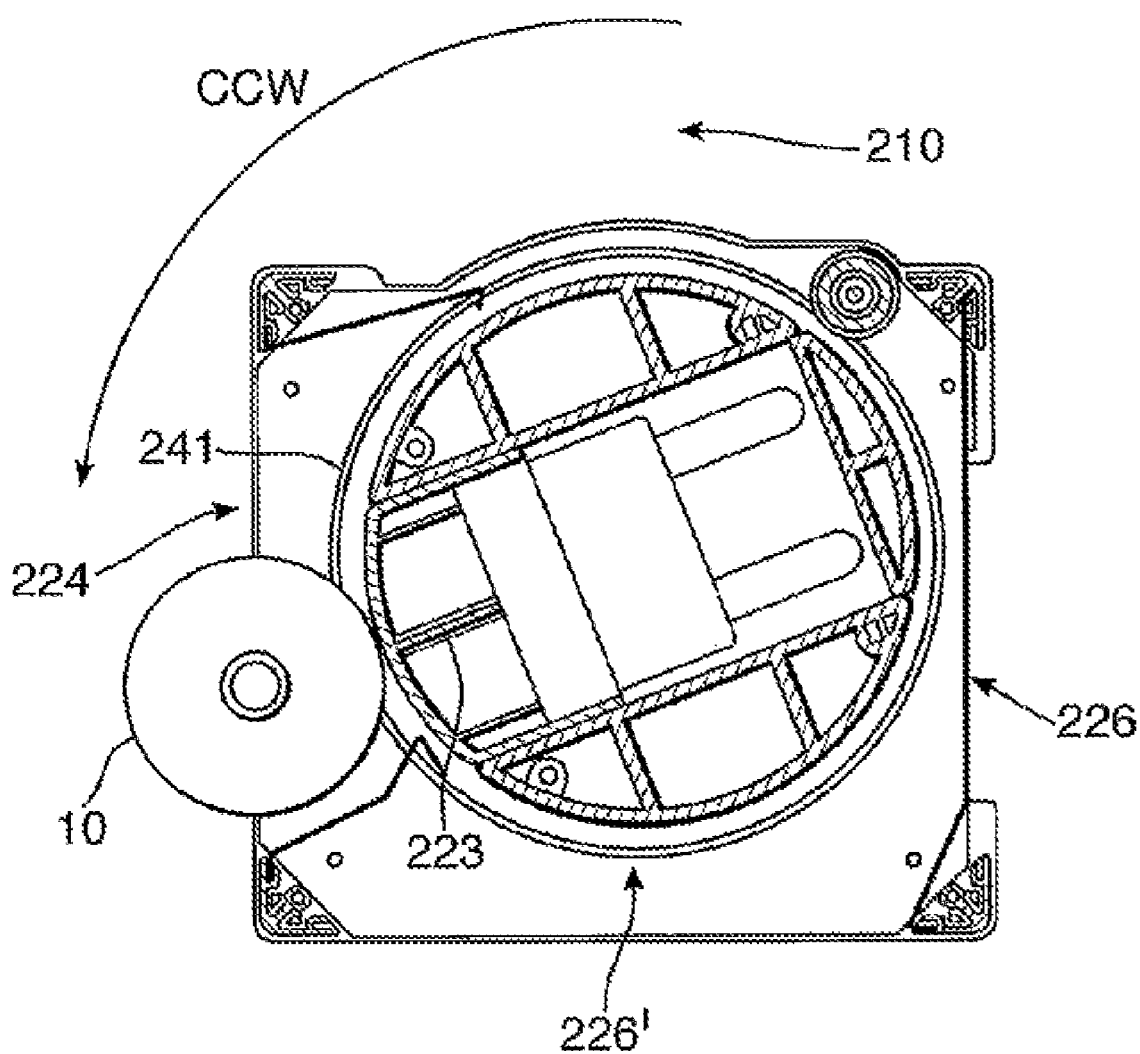
FIG. 13 is a partial sectional view of an embodiment of a drum type conveyor for incorporation in the storage facility of the present invention, the drum being rotated in a first direction from the second position to assume a third rotational position in which with the piston-like plunger element is in an advanced position.

In FIG. 13, a partial sectional view of the drum type conveyor shows the drum in a third angular position, where the movable element has been moved in a first and counter-clockwise direction from the retracted position shown in FIGS. 11 and 12 to an advanced position to drive the returnable item to the first output 224, preferably for the purpose of driving the object/item 10 towards the in-feed opening of a storage chamber 110. If driven in a second and clockwise direction to a second output, which is either output 226 or output 226', but not both, in-feed to a respective storage chamber 112 or 114 could be envisaged. The drum type conveyor is provided with said guide 241 to restrict the item 10 to its location in the cavity 222 while the drum is being rotated from the second position with the space 222 facing the input receiving area 210 to the third angular position where the opening of the cavity 222 is facing the first output 224. The same situation is also shown in perspective view FIG. 14, with the opening of the cavity 222 aligned with the first output 224 and with the movable element 223 in an advanced position.

Figure 15:
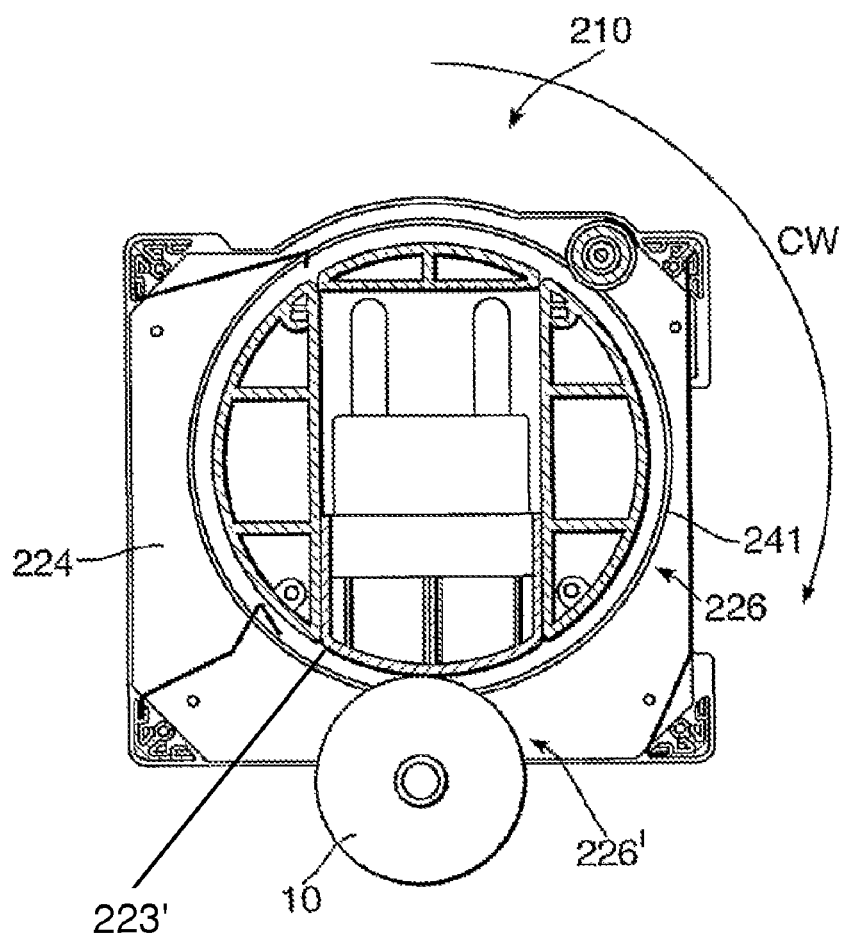
FIG. 15 is a partial sectional view of an embodiment of a drum type conveyor for incorporation in a storage facility according to the invention, with the drum rotated in a direction opposite to that starting at FIGS. 11, 12 and ending at FIGS. 13, 14, i.e. a rotation in clockwise direction—as viewed on FIG. 15—from the second position to the first position to assume a further rotational position with the piston-like plunger in an advanced, downwardly facing position.

In FIG. 15, a partial cross sectional view of the drum type conveyor shows the situation based on the situation shown in FIG. 11, now with the drum rotated in a second and opposite rotational direction (clockwise direction in the example), whereby the returnable object/ item 10 that was received in the space or cavity 222 when the drum was in its second rotational position has been carried by the drum through a rotation of the drum through approximately 180° so that the drum assumes its first position as shown on FIGS. 9 and 10. The object/ item is driven out from the space 222 by the movable element 223 moving from a retracted position to an advanced position, but also by the effect of gravity. A guide 241 is provided to restrict the movement of the object/ item 10 when held in the space 222 while the drum is being rotated from the second rotational position with the space facing the input receiving area 210 to the first rotational position with the opening of the space 222 and the curved face 223' (FIG. 15) of the element 223 being in register with the output 226'. The situation of FIG. 15 is also shown in the perspective view from below of FIG. 16, with the item 10 exiting from the conveyor at the alternative output 226'.

For conveying an item 10 that has entered the recess-like space or cavity to one out of two possible outputs in a specific embodiment of the combined drum conveyor and sorter, different directions of rotation can be used. For example, in the embodiments shown in FIGS. 9-16 of the accompanying drawings, the drum would be rotated in a first direction (e.g. counter-clockwise, as shown) to deliver the item at the first output 224, while a rotation in a second direction (e.g. clockwise, as shown) would be applied to the drum for delivering the item 10 at a second output 226 or 226'.

Thus, in the present context, there are in effect four main rotary positions of the drum 220:
a) the first rotary position with the recess 222 and the element 223 facing downwards;
b) the second rotary position with the recess 222 and the element 223 facing upwards, thus facing the input receiving area,
c) the third rotary position with the recess 222 and the element 223 facing the first output 224, and
d) the fourth rotary position with the recess 222 and the element 223 facing the second output 226 or facing the alternative second output 226'. If facing output 226', the fourth rotary position will in effect be the same as the first rotary position.

Now, with reference to FIGS. 17, 18 and 19, a load cell arrangement for determining a mass of a returnable item positioned on the drum type conveyor of the invention will be explained. When positioned to rest on the drum 220 or when rotating the drum 220 to spin the item 10, the item 10 will also in part be resting on or rotating with the roller 243, if such roller 243 is provided. Reference is also made to FIG. 9 to see how the object/item 10 will be resting against the roller 243. For making a decision as to whether or not to accept the object/item 10 for storage in the facility according to the invention or to determine an appropriate storage chamber in an embodiment having multiple storage chambers, the mass of the object/item 10 should be determined. To facilitate a mass determination, the roller 243 is provided with at least one bearing 245 support the roller shaft 247 at one end of the roller, which bearing 245 is connected to and supported by a load cell 246. In the exemplary embodiment shown in FIG. 17, the load cell 246 is attached to a frame 240 for the conveyor, while a further bearing 248 is provided at an opposite end of the roller.

Figure 17:
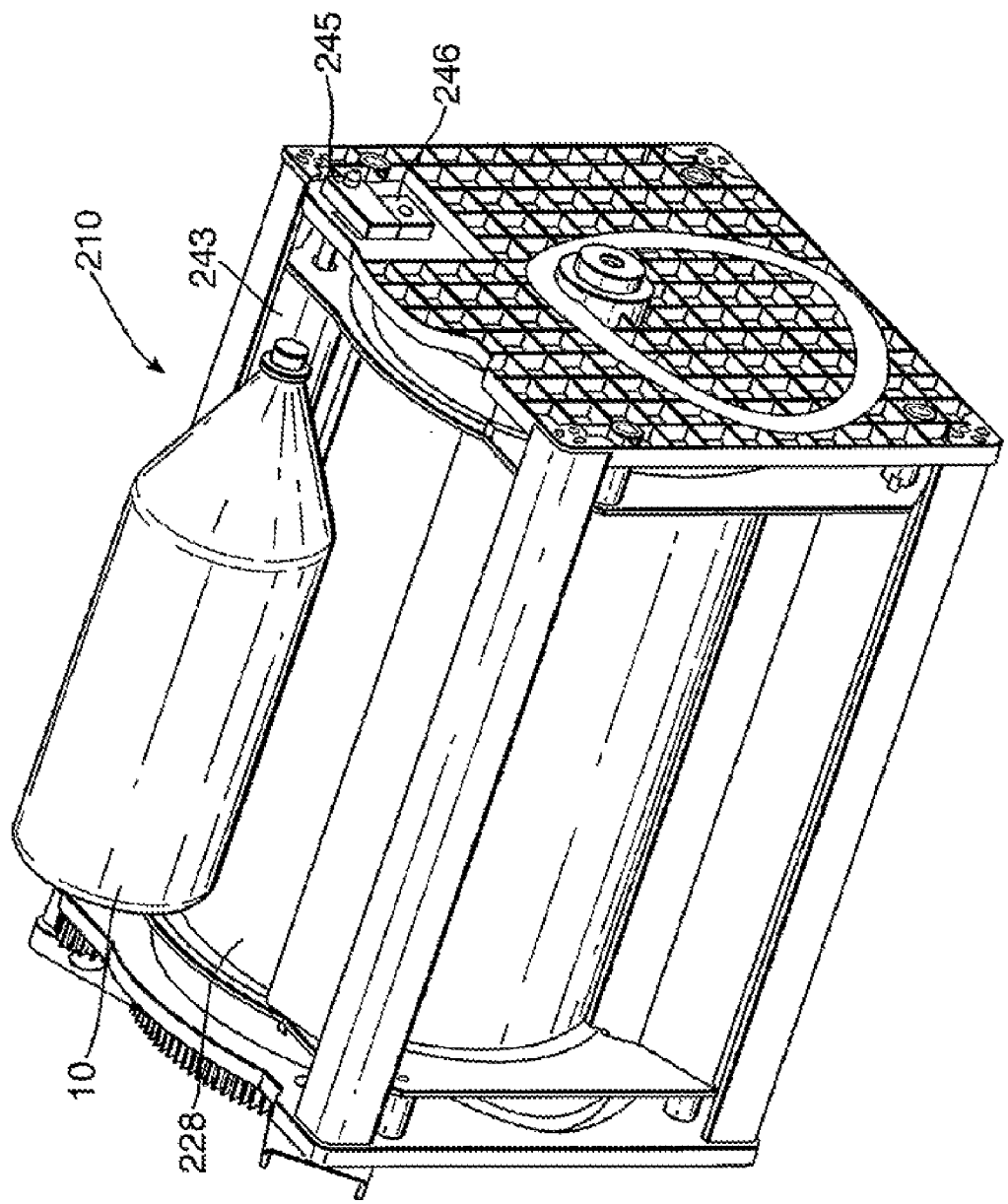
FIG. 17 is a perspective view of an embodiment of a drum type conveyor for incorporation in a storage facility of the present invention, having a roller and a load cell applied to the roller.
Figure 18:
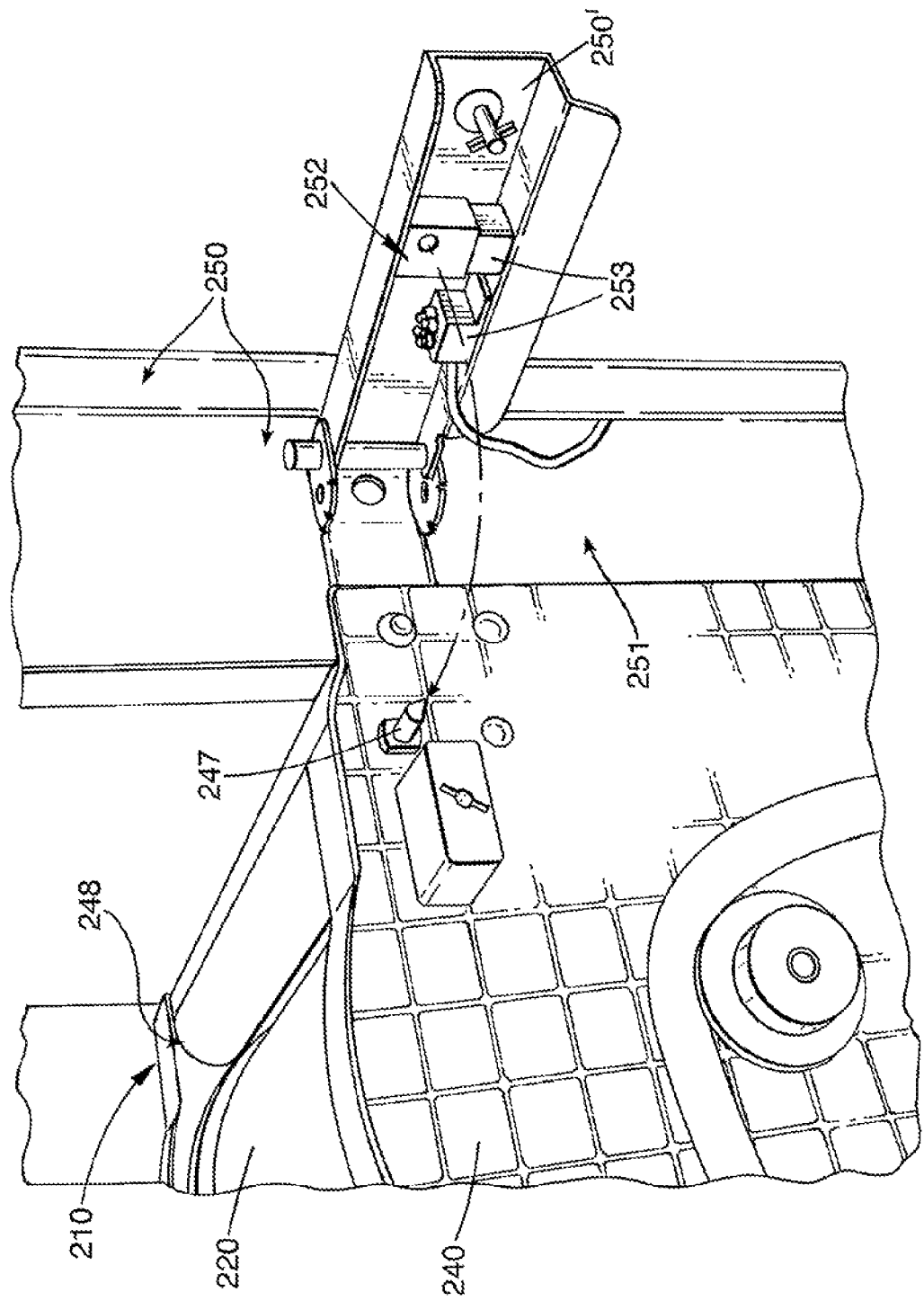
FIG. 18 is an illustration of a drum type conveyor embodiment positioned in a cabinet with a bearing for the roller and load cell on a movable arm.
Figure 19:
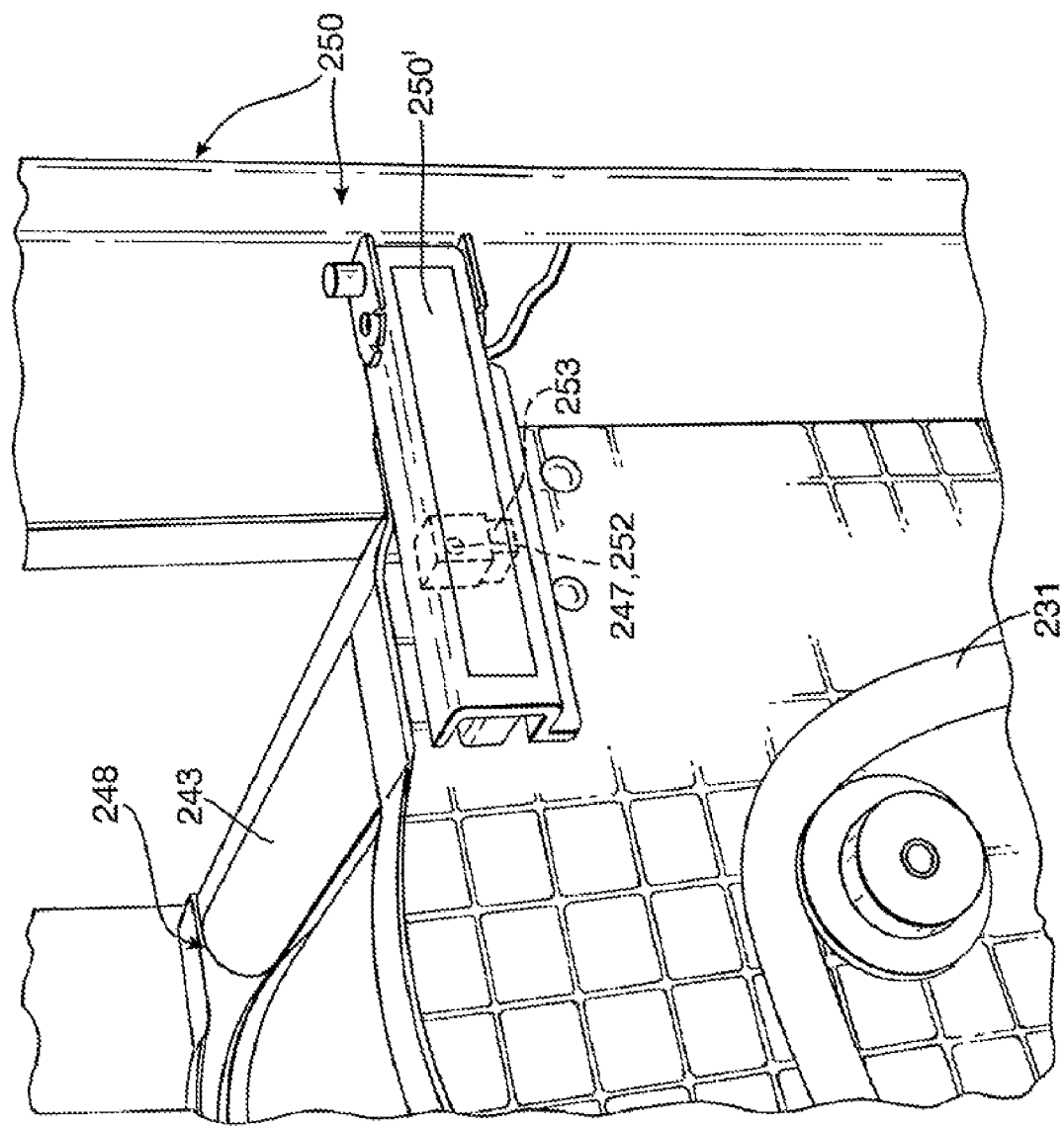
FIG. 19 shows the bearing and load cell arrangement of FIG. 18 with the movable arm positioned for bearing and load cell engagement with a roller.

A second and alternative embodiment of a load cell arrangement of FIG. 17 for determining a mass of a returnable object/item 10 resting on the roller 243 is depicted on FIG. 18. The arrangement includes a bearing 252 to be applied to one end of the roller shaft 247 when the conveyor is positioned in a cabinet 250. In this particular embodiment, the shaft 247 is partly free to move about in a plane perpendicular, suitably vertically, relative to the roller's 243 axis of rotation, and with the bearing 252 applied to the end part of the shaft 247 of the roller 243 after positioning the drum type conveyor in the cabinet 250. 251 denotes an electrical connection to the load cell 253. Thus, in FIG. 18, the removable bearing 252 and its associated load cell 253 is shown in a detached position, while, in FIG. 19, the cabinet arm 250' holding the bearing 252 has been relocated to a position where the bearing 252 engages the bearing receiving end of the roller shaft 247 to provide a bearing with a load cell 253 referenced to the cabinet 250 or to the frame 240. The embodiments of FIG. 17-19 are particularly advantageous to avoid as far as possible the risk that remaining liquid contents in returnable objects/ items 10 that are positioned on top of the conveyor typically can be spilled, as such spillage will likely require more frequent removal of the conveyor assembly from the cabinet than normally for cleaning away spilling of such unwanted liquid. Also, the use of the load cell prevents an RVM user from being successful with a swindle attempt by entering a full, unopened beverage container into the receiving area and place on top of the drum. The detection system 20 (see FIG. 8) will—as to be explained later—according to predetermined data determine that a specific observed and recognized item should have a specific weight or weight range. If the item is a full beverage can or bottle, the RVM will determine that there is a potential swindle situation and may trigger an alarm. Furthermore, in the embodiment shown, the drive means for operating the conveyor is separable from the drum type conveyor itself (as will be explained later), such that, by removing the conveyor from the storage facility assembly, the load cell will remain at the facility (i.e. located on the cabinet arm 250') and thus be protected from being subject to possibly harmful cleaning agents and water that typically would be used for cleaning the conveyor. If the load cell is located on the frame 240 of the conveyor, as depicted on FIG. 17, special measures must be taken to ensure that the load cell is not damaged in any washing or cleaning operation of the conveyor 200. Thus the embodiment of FIGS. 18 and 19 would be the preferred embodiment.

Plunger-Type Conveyor Means

In the following, a piston-like moveable plunger in a stationary housing-type of conveyor part of the present invention will be explained.

Figure 20:
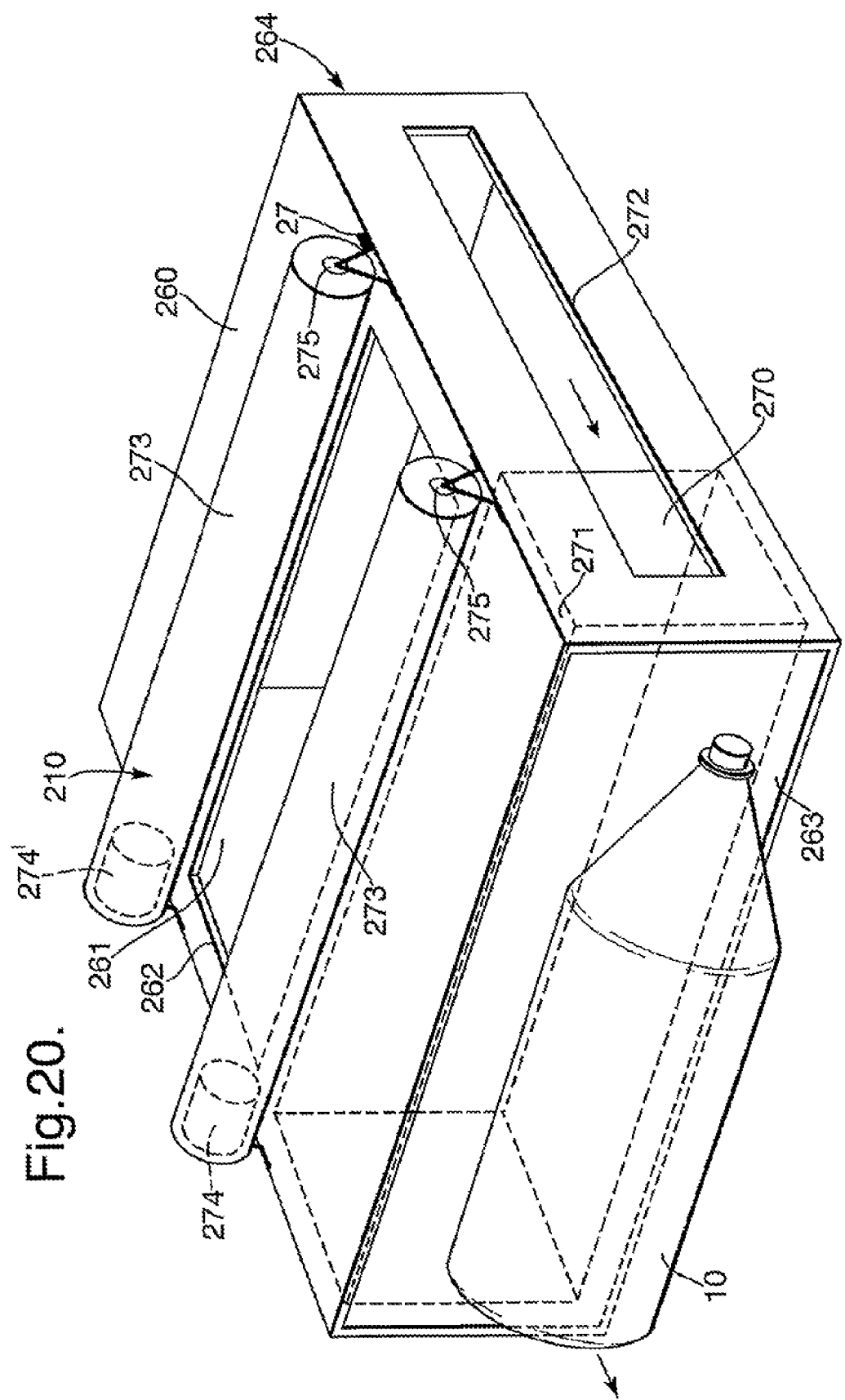
FIG. 20 is a principle drawing of a first embodiment of a conveyor having a moveable plunger in a stationary housing and useful for a storage facility according to the invention.

Reference is first made to FIG. 20, which in principle shows a first embodiment of a substantially linearly moveable plunger in a stationary housing type conveyor, as comprising an elongated housing 260 with an input opening 262 on one side adapted to face the input receiving area 210 of the storage facility, an interior space 261, a substantially linearly movable plunger or slide member 270, a first output 263 and a second output 264. Although exemplified here with a housing based on a straightforward design for a rectilinear movement of the plunger, the housing may be designed to be curved in any direction to allow an output in an arbitrarily chosen angle. With a housing having a curved shape, naturally, the plunger would follow a curved path corresponding to the shape of the housing. Also shown in FIG. 20, is an elongated slot 272 in one side of the housing, which is provided as an access means for allowing a plunger drive means (not shown) to be attached to the plunger 270 for positioning of the plunger in different parts of the interior space 261. Such a slot can be provided at any longitudinally extending side of the housing, and also at more than one side to provide a balanced drive force to the plunger. In FIG. 20 is also shown a returnable object/item 10 which has been positioned in the input receiving area, and which by the aid of gravity and the provision of the input opening 262 will fall into the interior space 261 of the housing, and thereby become located adjacent to the plunger 270 when the plunger initially has been positioned in a first position which is below the opening 262.

Figure 21:
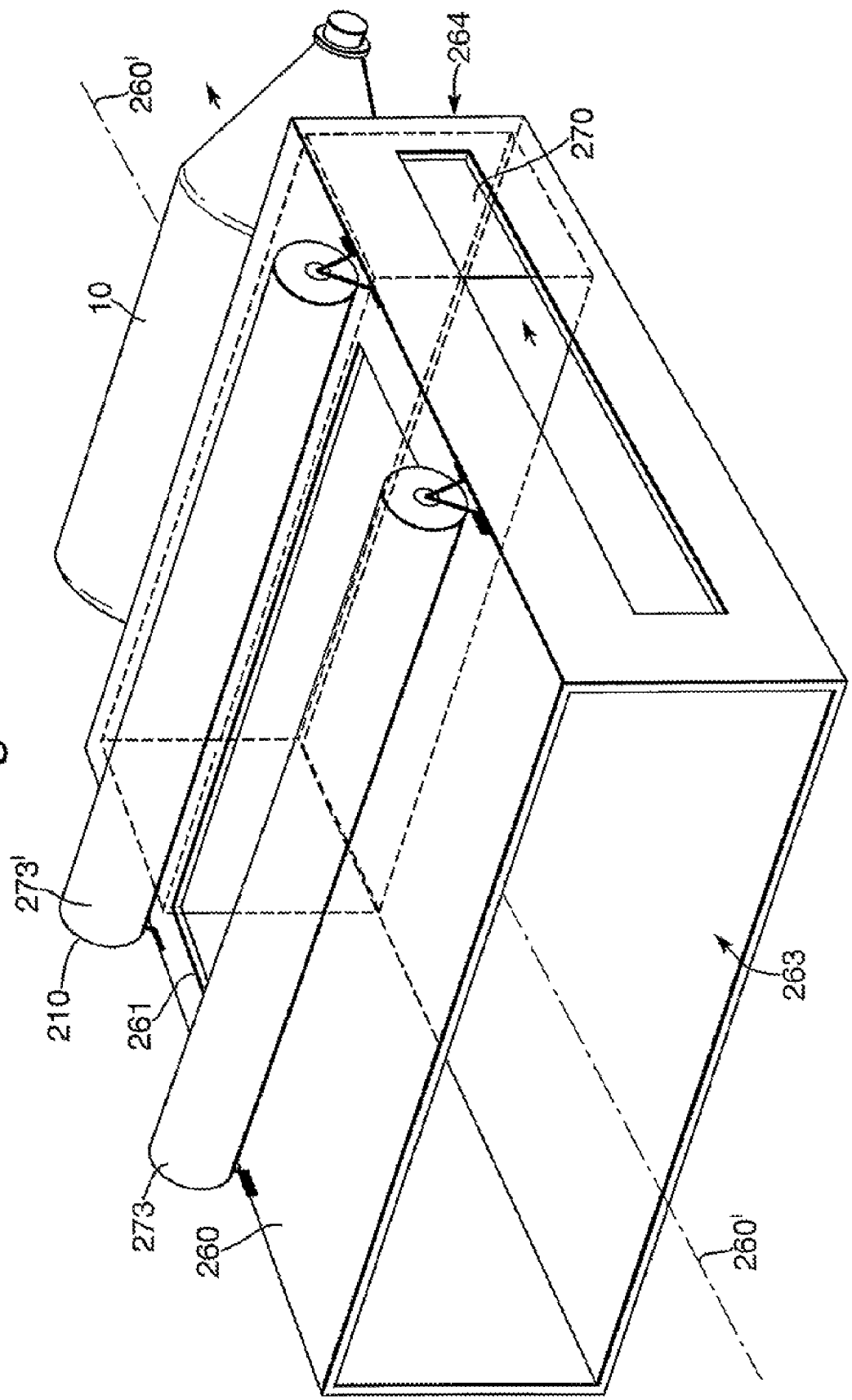
FIG. 21 is a principle drawing of the conveyor of FIG. 20 in a different operational state.

In a preferred embodiment of the conveyor and sorter of the present invention, as shown on FIGS. 20 and 21, embodying the moveable plunger in a stationary housing type conveyor, the conveyor suitably includes an item turning device, preferably using at least one roller 273 or preferably two rollers 273, 273" if two outputs 263, 264 are two be used. The device is located adjacent the input opening 262. The upper side face 271 of the plunger, i.e. the side of the plunger that will be facing the input opening 262, has a surface structure that is specially prepared to provide good friction against a returnable object/item 10 that has been deposited in the input receiving area and brought to rest on the upper side face 271 of the plunger. A rotation of the object/item 10 that rests on the upper side face 271 of the plunger 270 is then obtainable by movement of the plunger 270 while the object/item 10 is resting on top of the plunger 270, which rotation is further augmented by the rollers 273, 273'. The rollers 273, 273' also cause the object/item 10 to not move away from the opening 262 while rotated or if the longitudinal axis 260' (see FIGS. 21 and 23) of the housing forms an angle with the horizontal. The upper side face 271 of the plunger 270 can be extended in any direction of movement of the plunger 270, to obtain a desired range of turning of the item 10 that rests on the upper side face 271 of the plunger 270. Although just one roller 273 may suffice, a preferred embodiment of the plunger type conveyor and sorter has two rollers 273, 273', one at each side of the input opening 262, to facilitate rotation of the item 10 in any direction in connection with a movement of the plunger 270 in the longitudinal direction of the housing 260. The rollers are rotatably supported at each end by mountings 275. The rollers 273; 273' can be freely rotatable, or they can be driven by a driver arrangement 274 by way of a separate drive means or by a linkage to the plunger 270 or the driver for the plunger. Preferably, but not necessarily, the drive means 274; 274', e.g. a motor inside the roller, is arranged such that a surface velocity of the roller 273 during its rotation is about the same as the surface velocity of the upper face 271 of the plunger 270, relative to the housing 260 as the plunger 270 is moved in the housing 260. In order to obtain a measure for the mass of a returnable object/item 10 resting on the plunger 270, any roller arrangement 273 can include a load cell 276 suitably supporting the roller at one end thereof in order to measure a reaction force exerted on the roller as a function of an acceleration or turning of the object/item 10 due to movement of the plunger 270, or a reaction force due to the weight of the item 10, in particular if longitudinal axis of the housing 260 is made to tilt, e.g. in the range of ±0°-30° relative to the horizontal.

In a next step of operation of the linear movement type conveyor, when the upper face 271 of the plunger has moved away from the opening 262 either towards output 263 or 264, the returnable object/item 10 will enter into the interior space 261, the plunger 270 will then upon movement in an opposite direction apply a driving force to the object/item 10 to drive it towards and through e.g. the first output 263 if the plunger at first had moved away from the opening 262 towards output 264, or towards and through e.g. the second output 264 if the plunger had at first moved away from the opening 262 towards output 263. In either case the plunger 270 would preferably force the item, towards an in-feed opening 140 (see FIG. 2a) or an in-feed opening 141 or 142 (see FIG. 6) of a storage chamber of a storage facility as disclosed herein.

Figure 22:
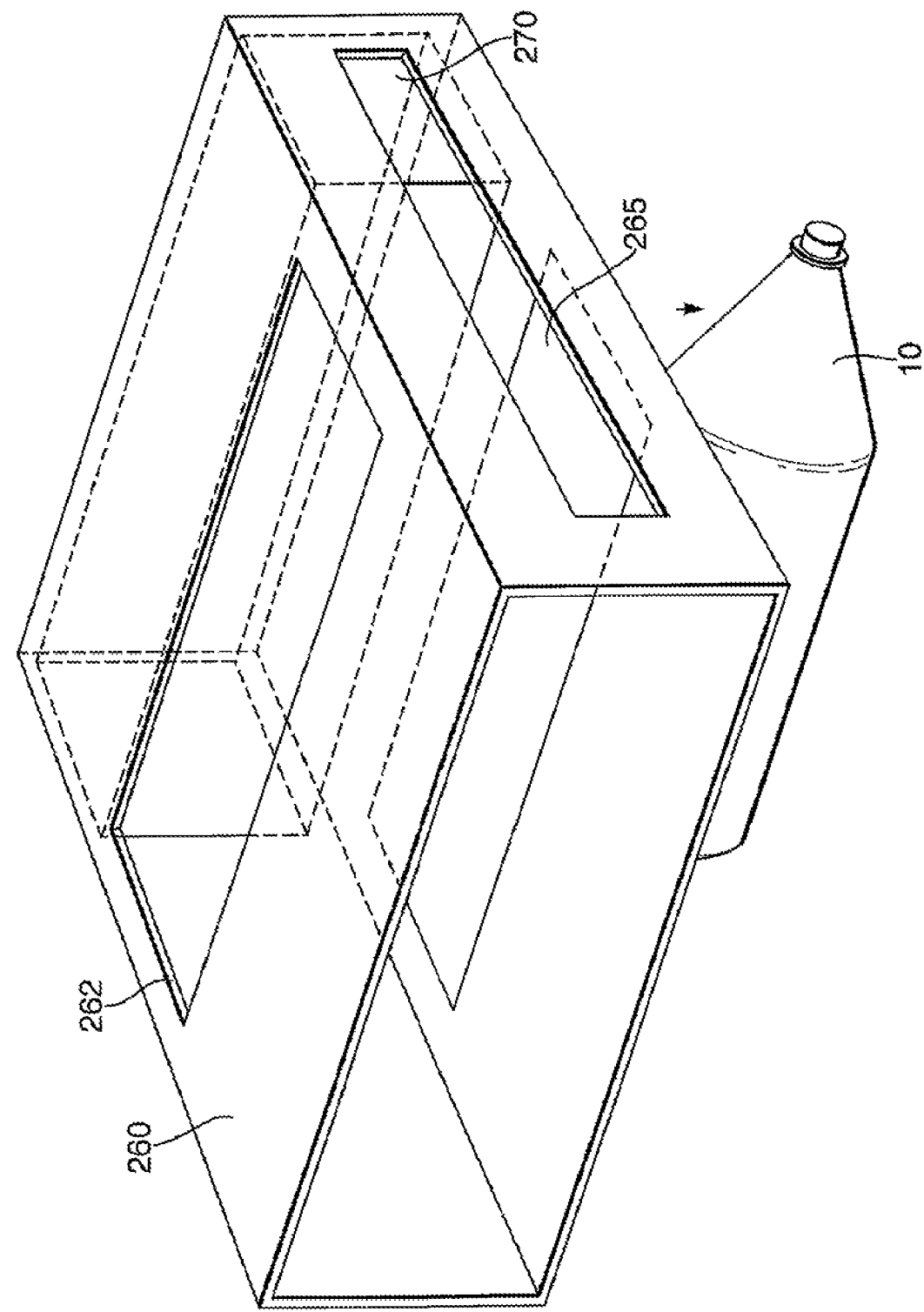
FIG. 22 is a principle drawing of a second and modified embodiment of the conveyor of FIGS. 20 and 21.
Figure 23:
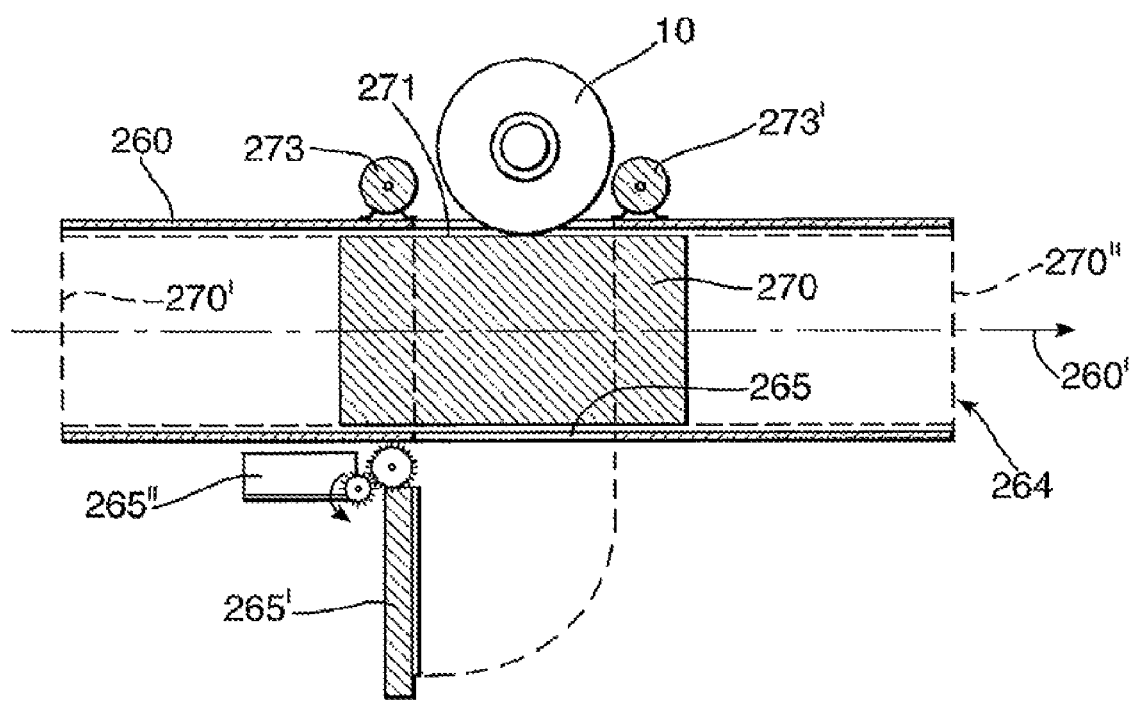
FIG. 23 is a schematic side view of the conveyor of FIG. 22.

Now, with reference to FIG. 22, a further variant of the conveyor and sorter of the type having the moveable plunger in a stationary housing will be explained, this embodiment exhibiting three outputs. In this variant, at least three positions for the plunger element in the housing are defined, namely with the plunger positioned immediately under the input opening 262, with the plunger positioned toward a first output 263 in the first movement direction of the plunger 270, and a further position where the plunger has been moved near a second output 264. For the sake of clarity, the rollers 273, 273' have not been shown on FIG. 22, but the rollers will preferably be present in a practical embodiments. The variant shown in FIG. 22 includes a third output 265 of the housing, the third output being located opposite to and below the input opening 262 in the bottom of the housing 260. Preferably, the third output 265 includes a closing means 265' which is shown on FIG. 23, but not on FIG. 22. The closing means 265 is capable of controllably blocking the output 265 such that an object/item 10 that has entered the interior space 261 of the housing 260 selectively can be kept from exiting the housing through the output 265 if the object/item 10 is instead to be directed towards a different output, e.g. output 263 or 264. The means 265' for selectively closing the third output 265 can be made operational by way of a separate driver or actuator 265", e.g. a solenoid, or by a linkage to the plunger 270, for example by placing the output in an open state when the plunger is placed in an extreme position within the housing, such as for example in connection with a movement of the plunger beyond the position of the plunger 270 as shown in e.g. on FIG. 22. By the depositing of an object/item 10 in the input receiving area 210 immediately above the input opening 262, and with the third output 265 in an open state, and by locating the plunger 270 is a position where it does not block a passage provided between the input 262 and the third output 265 by the interior space 261 of the housing, the object/item 10 is allowed to pass through the opening 262, the interior of the housing 260 and then exit through the opening 265. The exit of the item 10 after having traveled straight through the housing from the input 262 to the output 265 is shown in FIG. 22.

Figure 24:
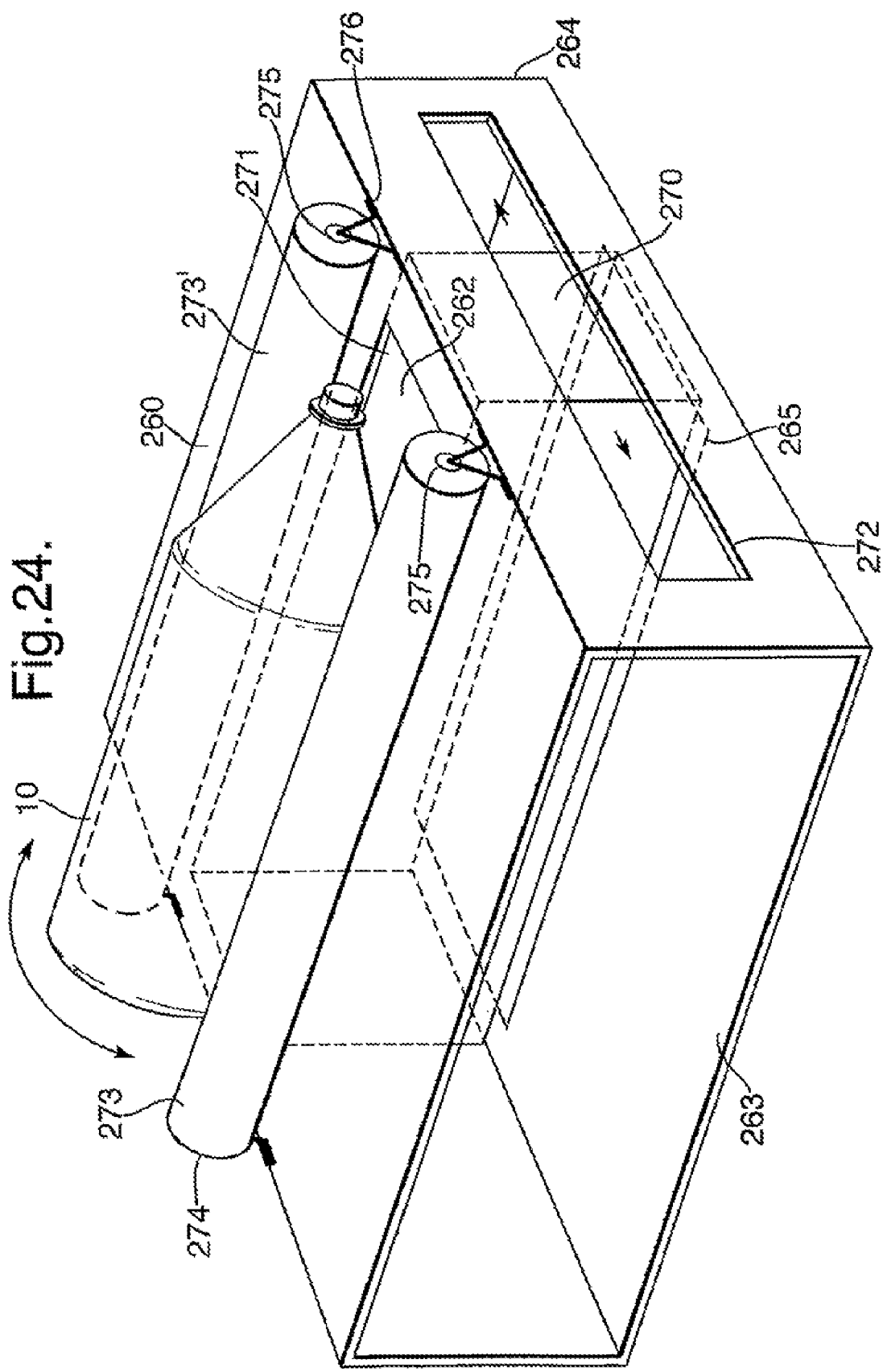
FIG. 24 is a principle drawing of the conveyor of FIGS. 20-23 to illustrate rotation of a returnable item received in the input receiving area of the conveyor.

FIG. 24 illustrates how the plunger 270 may be used to rotate the object/item 10., e.g. a bottle, by moving the plunger either way, the rollers 273, 273' assisting a safe and efficient rotation of the item 10. The understanding of FIG. 24 as regards rotation of the item 10 before it enters into the interior 261 of the housing 260 will be the same, irrespective of the presence of the output 265. In effect, the three-outputs embodiment could be made instead as a two-outputs embodiment, having e.g. outputs 263 and 264, outputs 263 and 265 or outputs 264 and 265.

Single Camera Viewing Device

Figure 25:
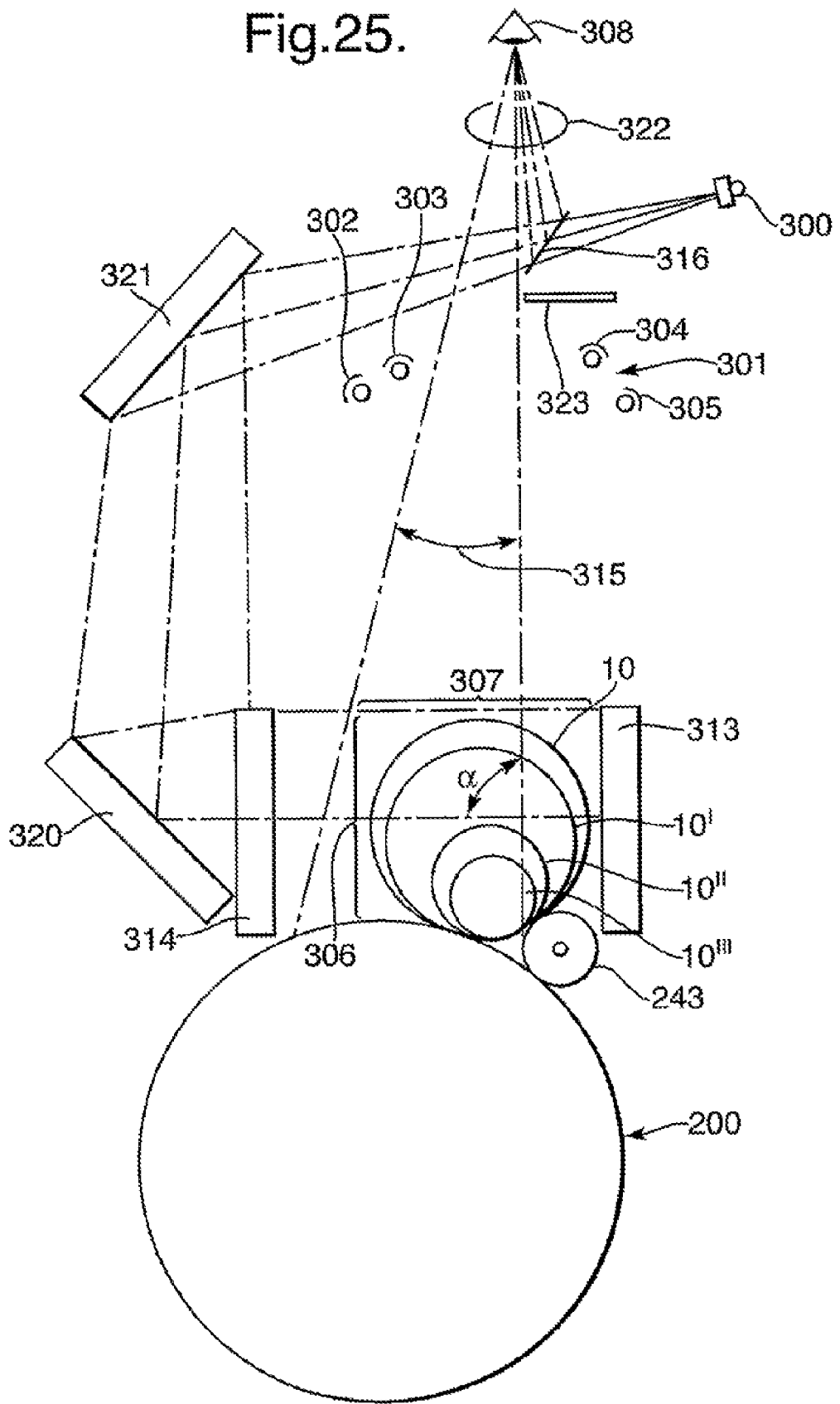
FIG. 25 is a principle sketch of a first embodiment of a camera-aided viewing device for viewing an object with regard to contour of the object and identifying features or indicia on the object.

FIG. 25 depicts a first light source 300 and a second light source 301, the light source 301 suitably consisting of a plurality of light sub-sources 302, 303, 304, 305. The light sources 300 and 301 are separately configured to illuminate a first region 306 and a second region 307 of an object, e.g. a returnable item 10; 10'; 10", 10'''. A single camera 308 is provided to view at least part of the regions 306 and 307. The first light source 300 is configured to assist the camera 308 in viewing of contour of objects, items or articles 10, 10', 10", 10''' of different cross section, e.g. empty beverage packaging such as cans and bottles against a light reflective area or background 313 forming a bright, light emitting background. The light from the first light source 300 is directed towards the object (e.g. one of those labeled 10 through 10''') as parallel light using a lens 314. The second light source 301 is configured to assist camera viewing by the camera 308 for detection and recognition of any identity features located on the object in viewing sector labeled 315.

Said identity features are suitably at least one of: bar code, graphic symbol and alphanumeric characters.

Although it would be feasible to use two cameras instead of a single camera, the use of a single camera yields less technical complexity, a simpler and more maintenance friendly structure, in addition to requiring less space in order to carry out the required functions. Further, from a components cost aspect and installation cost, the invention also offers a substantial advantage over a two-camera solution.

When a camera views e.g. an object contour or identifying features thereon, the camera sensor matrix provides a string of matrix pixel signals to be processed in order to identify or recognize such contour or features, including the possibility of letting the camera read and causing identification of e.g. a bar code.

As seen from FIGS. 25-28, the first light source 300 illuminates the first region 306 via a light path which includes an optical beam splitter (or view splitter) 316 (FIGS. 25 and 26), 318 (FIG. 27) or 319 (FIG. 28), at least one inclined mirror 320 and the lens 314. However, it is noted that in the most preferred versions, there is suitably used two mirrors 320 and 321, as shown on FIGS. 25-27, in the light path.

Figure 26:
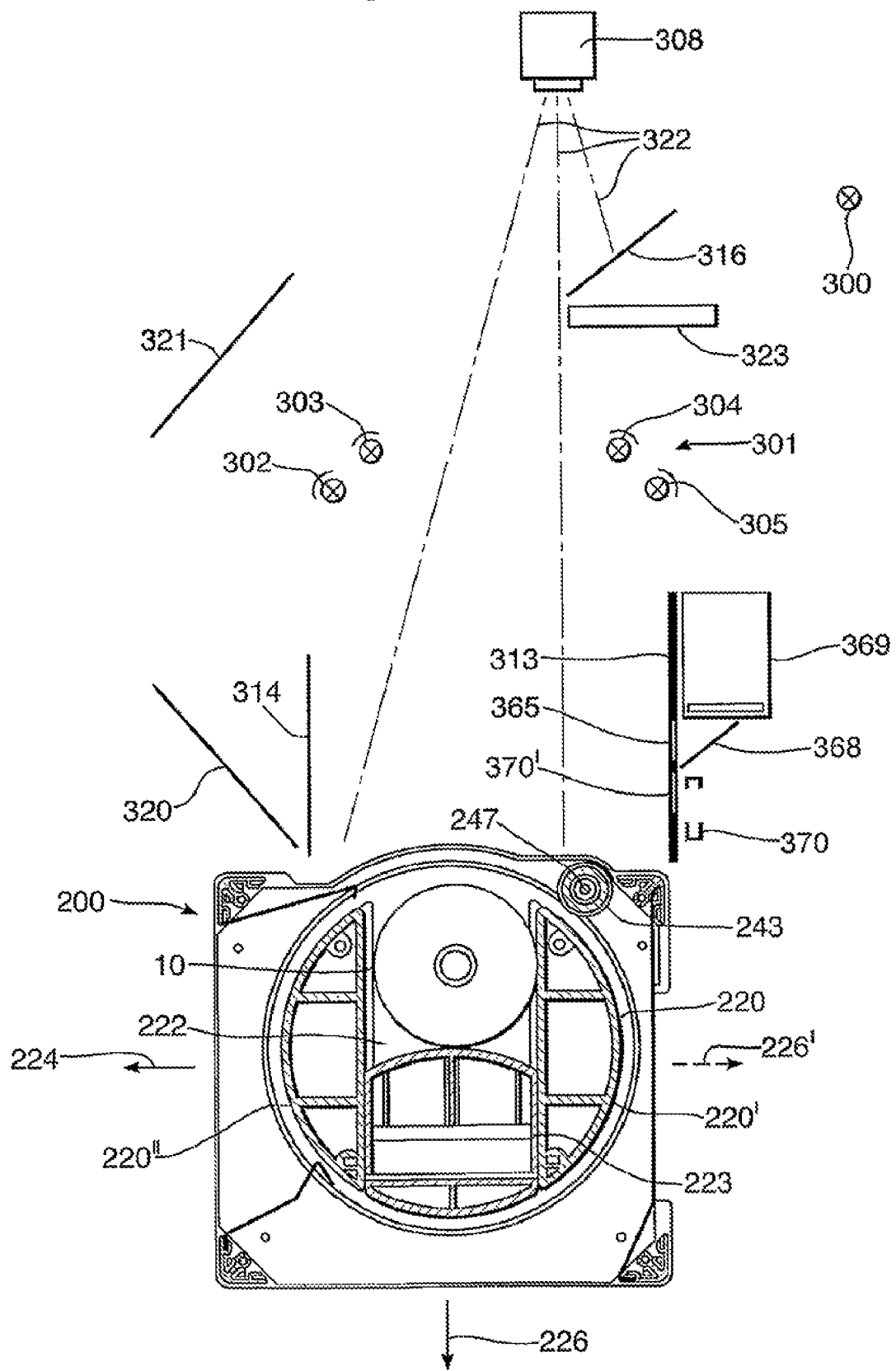
FIG. 26 is a principle, though slightly more detailed sketch of the first embodiment of the camera-aided viewing device showing in more detail a first object supporting, rotation, sorting and conveying means.
Figure 27:
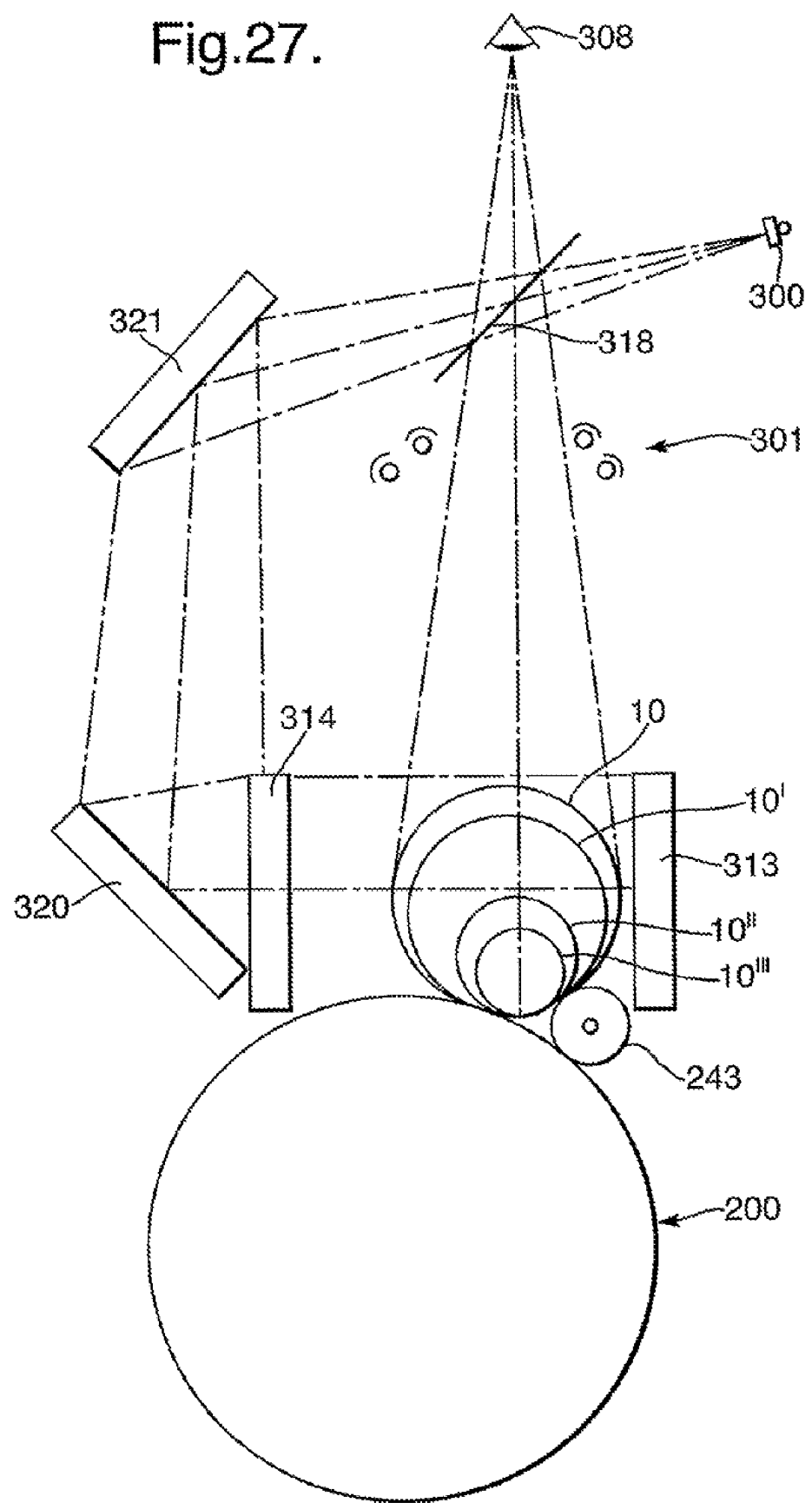
FIG. 27 is a principle sketch of a second embodiment of the camera-aided viewing device.
Figure 28:
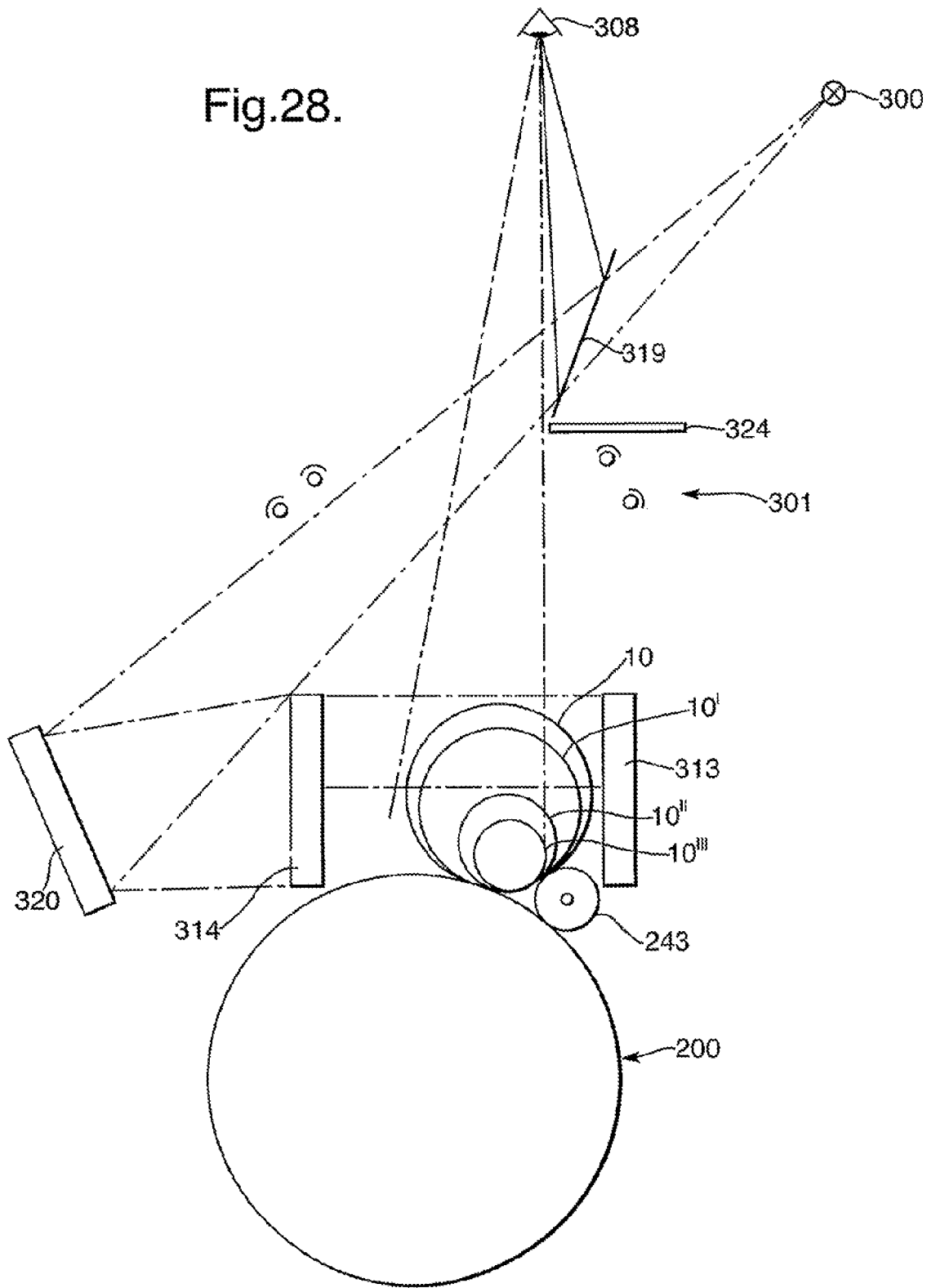
FIG. 28 is a principle sketch of a third embodiment of the camera-aided viewing device.

FIGS. 25, 26 and 28 depict a light beam splitter 316; 319 located in an inclined posture in the camera field of view 322 and covers at least part of said field of view, suitably approximately half of the camera field of view. FIG. 27 depicts an optical beam splitter 318 which covers the complete camera field of view.

It is seen from FIGS. 25-28 that camera viewing of the first region 306 via one mirror 320 or two mirrors 320, 321 is suitably made with line of sight towards the object shifted by an angle α of 90°±30° relative to camera line of sight towards the object when viewing the second region 307. In the drawing FIGS. 25-28 the angle α is shown as 90°. However, by arranging the mirrors 320, 321 differently, it is evident that the angle range of 90°±30° is possible.

In the case that there is used an optical beam splitter 316 or 319 which is within only half or less of the camera field of view, there is the possibility that when the camera is set to view the second region or part thereof, the splitter is suitably assisted by a vision blocker 323; 324 to prevent the camera from viewing both directly in the sector 315 and through the splitter, the splitter providing a less clear viewing. If the vision blocker 323; 324 is omitted, then the camera will be able to view the entire region 307.

FIG. 27 shows the camera in a configuration set to view the second region 307 completely via the beam splitter 318. This implies that the camera 308 views either the first region 306 via the splitter, the mirrors 321, 320 and the lens 314, and secondly the second region 307 through the splitter. In this latter situation, the light source 301 is fully or partly activated, and the light source 300 is deactivated.

Figure 32:
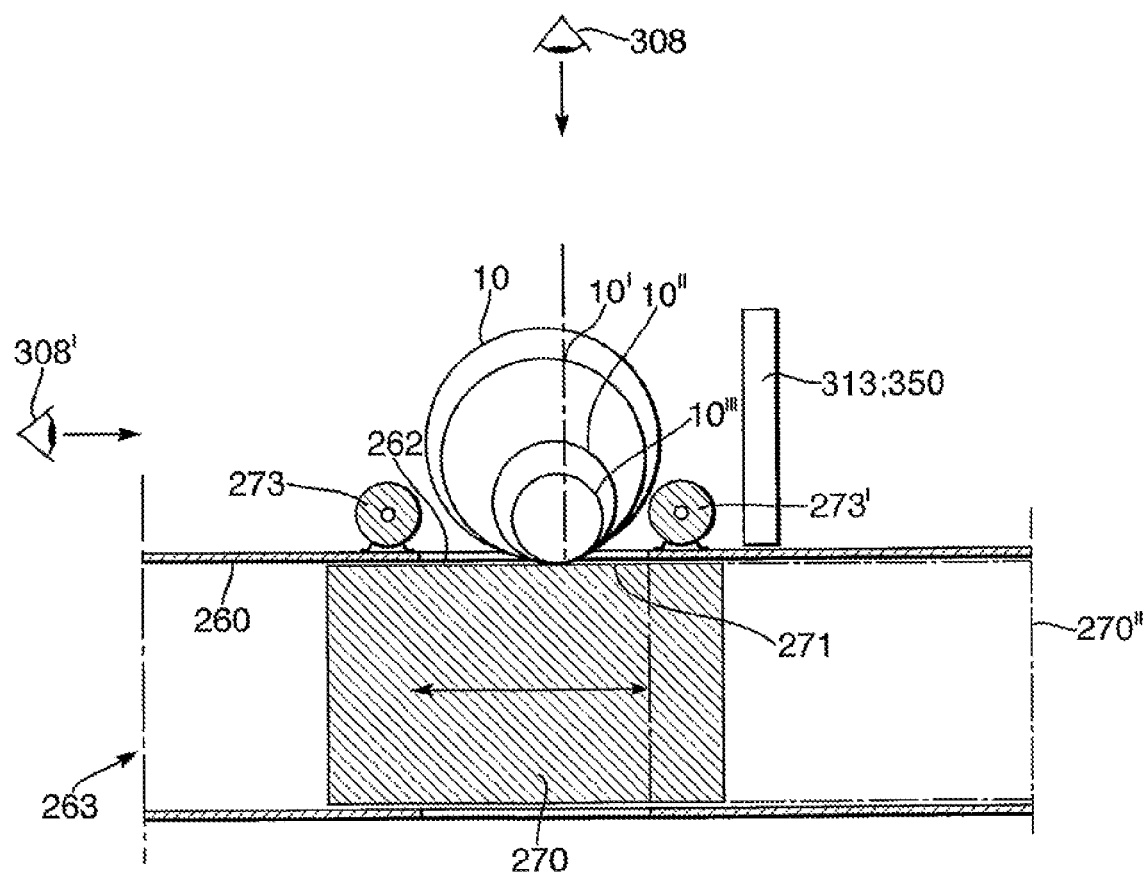
FIG. 32 is a principle sketch of a second object supporting, rotation, sorting and conveying means.

The light source 301, suitably comprising a plurality of light sub-sources 302-305, is notably located in a region between the beam splitter 316; 318; 319 and an object supporting means in the form of said compact conveyor and sorter 200. In the embodiments show on FIG. 25, 28-30, the object supporting means 200 is shown only schematically, but in more detail on FIG. 26. A more detailed operation of the object supporting means 200 and a possible, schematically shown alternative on FIG. 32, is disclosed in the preceding disclosure of FIGS. 1-24.

It will now be briefly highlighted some of the earlier disclosed features of the object supporting means 200 in a specific context of camera aided viewing of an object, e.g. the object 10, located on the object supporting means 200, said supporting means is in the form of the rotary drum 220 (see FIG. 26) with the auxiliary roller 243. The drum 220 and the roller 243 will controllably, but forcibly rotate the object 10 on a portion 220' or 220" of the circumference of the drum. The drum 220 has at least one radial inwardly directed, adjustable space or cavity 222 for receiving the object 10 after its rotation on said circumference portion and for transporting the object 10 through rotation of the drum to an output location, e.g. at generally indicated by arrows 224, 226 and 226'. The camera 308 will be able to view and cause detection of the presence of the object 10 when it has dropped into the adjustable space 222. This has a safety function aspect and also a security function aspect., i.e. to prevent any swindle attempt. This means that the drum 220 will not start turning until the camera 308 actually observes and causes detection of the object being present in the space 222 and with the movable element 223 operating as a movable bottom in its fully retracted state.

The direction which the drum will then turn is determined by set criteria which are compared to recognize characteristic features of the object. This will be more fully explained and considered in connection with the disclosure of FIG. 38. Further, in case the contour of the object is to be viewable from above, rather than sideways, it would be advantageous to let at least a part of the rotary drum 220 be provided with a coating which is retro-reflective to light, in particular at the portions labeled 220' and 220" of the drum 220. Such a situation is in particular suitable in connection with the embodiment shown on FIG. 29 and will be further explained later.

A brief repeated disclosure is now made of the alternative supporting means as shown on FIGS. 20-24 in the context of camera aided viewing of an object 10. The single camera is generally denoted by 308, 308', the reference 308' symbolizing viewing by the camera 308 via e.g. a beam splitter 318 and mirrors 321, 320 (see FIG. 27). Said supporting means is suitably in the form of the housing 260 forming a guide with an object receiving input opening 262 and a reciprocating plunger or 270 therein. There is suitably at one or both of two longitudinal sides of the opening 262 an auxiliary roller 273; 273' for roller support upon rotation of the object or item 10; 10'; 10"; 10''' on the plunger 270 when it is set to move with its upper surface 271 past said opening, thus enabling the camera 308 to read an identifying feature on the object or item 10 if not immediately viewable by the camera. The plunger 270 is controllable to move beyond said opening 262, e.g. to the position shown by dotted lines 270" to allow the object to drop into the interior of the housing 260 through said opening 262 and by return movement of the plunger 270 (towards left as shown on FIG. 32) causing the object to be pushed out of the housing to an output location 263. From the understanding and concept depicted in connection with the supporting means 200 on FIG. 26, it is readily appreciated that the object 10 is camera observable while at a location inside said housing 260 below said opening 262, provided that such location is in at least part of a field of view of the camera 308. In a particular embodiment, at least at the upper part 271 of the plunger 270 can be provided with a coating retro-reflective to light, thus enabling the contour of the object, e.g. 10, to be viewed from above.

Figure 29:
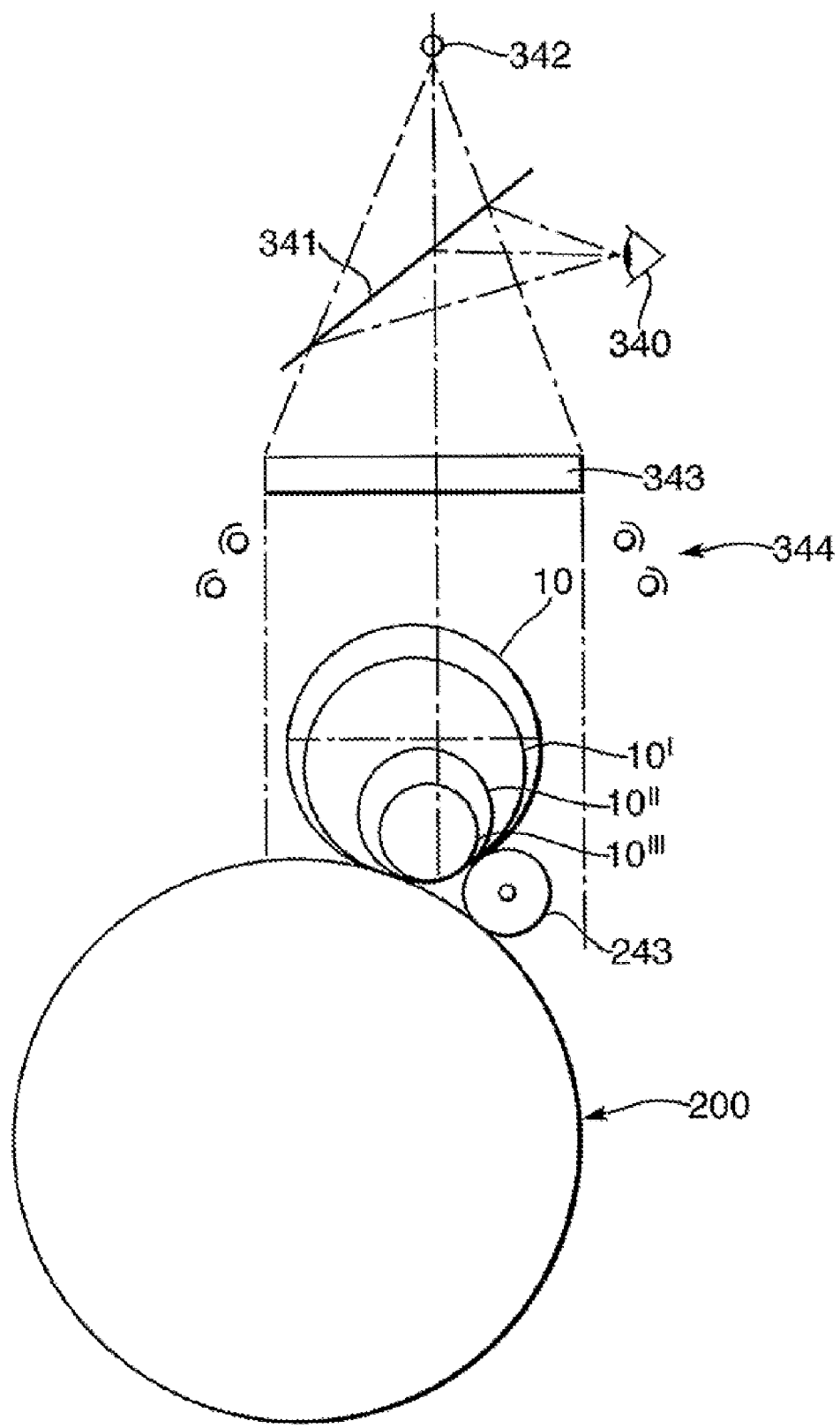
FIG. 29 is a principle sketch of a fourth embodiment of the camera-aided viewing device.

FIG. 29 shows the use of a single camera 340 and with an optical beam splitter 341 inclined relative to a lens 343. A light source 342 provides for illumination of the object, e.g. 10, through lens 343 to provide parallel light rays towards the supporting means 200, which has its drum parts 220' and 220" (see FIG. 26) provided with retro-reflective material or property enabling light not hit by the object to be retro-reflected back to camera 340 via the lens 343 and the splitter 341 to provide an image of the contour of the object. When it is desirable to view and read identifying features on the object, such as e.g. bar-code, a light source 344 is activated, the light source suitably being of the same type as the light source 301. At the same time, light source 342 may be deactivated, if required.

Figure 30:
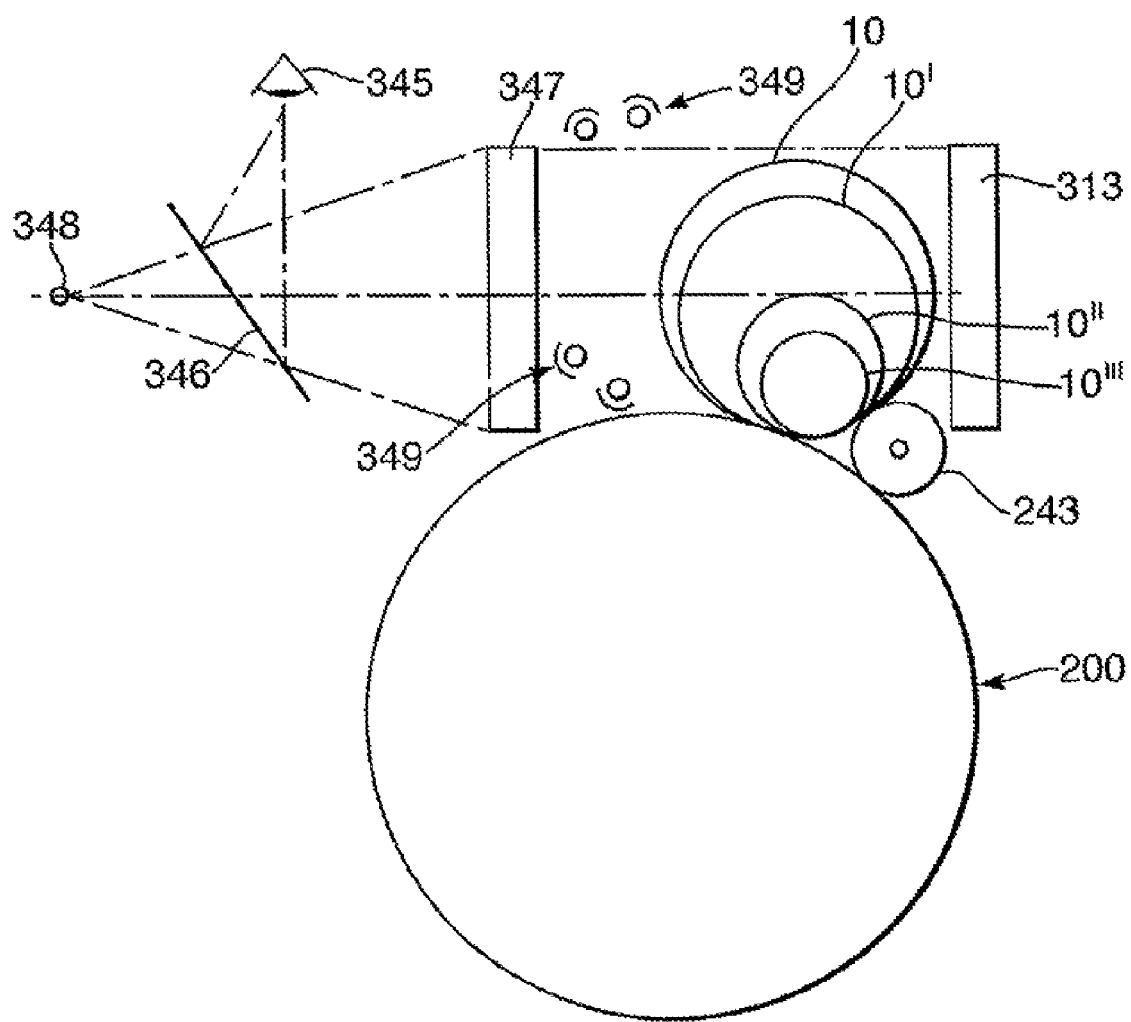
FIG. 30 is a principle sketch of a fifth embodiment of the camera-aided viewing device.
Figure 31:
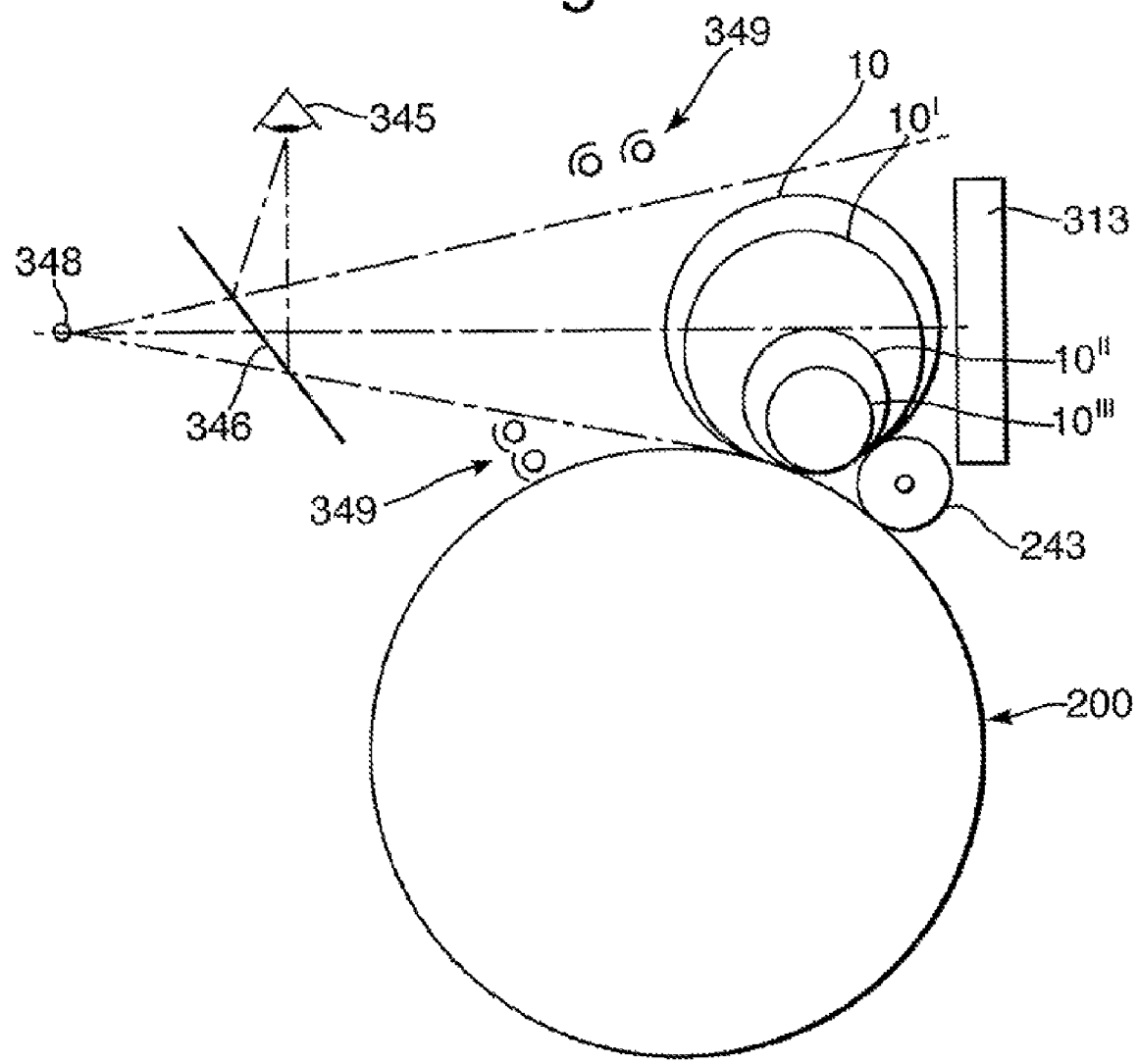
FIG. 31 is a principle sketch of a sixth embodiment of the camera-aided viewing device.

FIG. 30 shows an embodiment which in operation is similar to that of FIG. 29. A single camera 345 is used with an optical beam splitter 346 inclined relative to a lens 347. A light source 348 provides for illumination of the object, e.g. 10, through lens 347 to provide parallel light rays towards a light reflective background or area 313 enabling light not hit by the object to be retro-reflected back to camera 345 via the lens 347 and the splitter 346 to provide an image of the contour of the object. When it is desirable to view and read (or detect) identifying features on the object, such as e.g. bar code, a light source 349 is activated, the light source suitably being of the same type as the light source 344, i.e. comprising a plurality of light sub-sources. At the same time the light source 349 is activated, light source 348 may be deactivated, if required. FIG. 31 is a modification of the embodiment of FIG. 30, the major difference being the non-existence of the lens 347, thus yielding that the object contour is not viewed by means parallel light rays.

FIGS. 25-28 clearly demonstrate that the first and second regions 306, 307 are partly overlapping, and FIGS. 29-31 indicate full overlapping.

Figure 33:
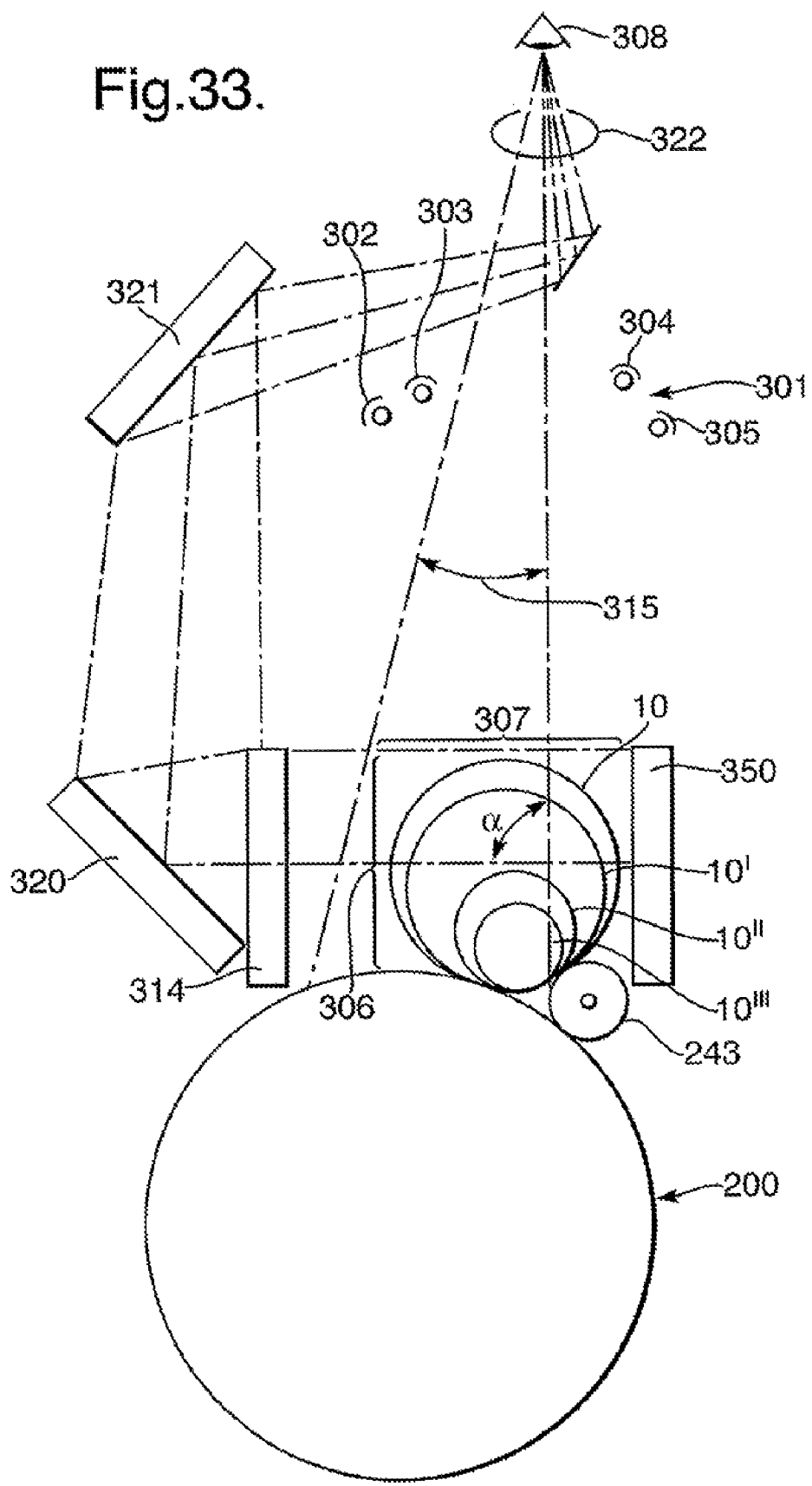
FIG. 33 is a principle sketch of a seventh embodiment of the camera-aided viewing device.

FIG. 33 is identical to the embodiment shown on FIG. 25, apart from the light source 300 and the retro-reflective background 313 having been deleted and replaced by a light emitting, illuminated or backlit panel 350, the panel 350 thus forming a bright background. Ambient light may in some applications be sufficient in order that the camera views a bright background.

The panel 350 will provide the bright background against which e.g. the object 10 is to be viewed by the single camera 308.

Figure 34:
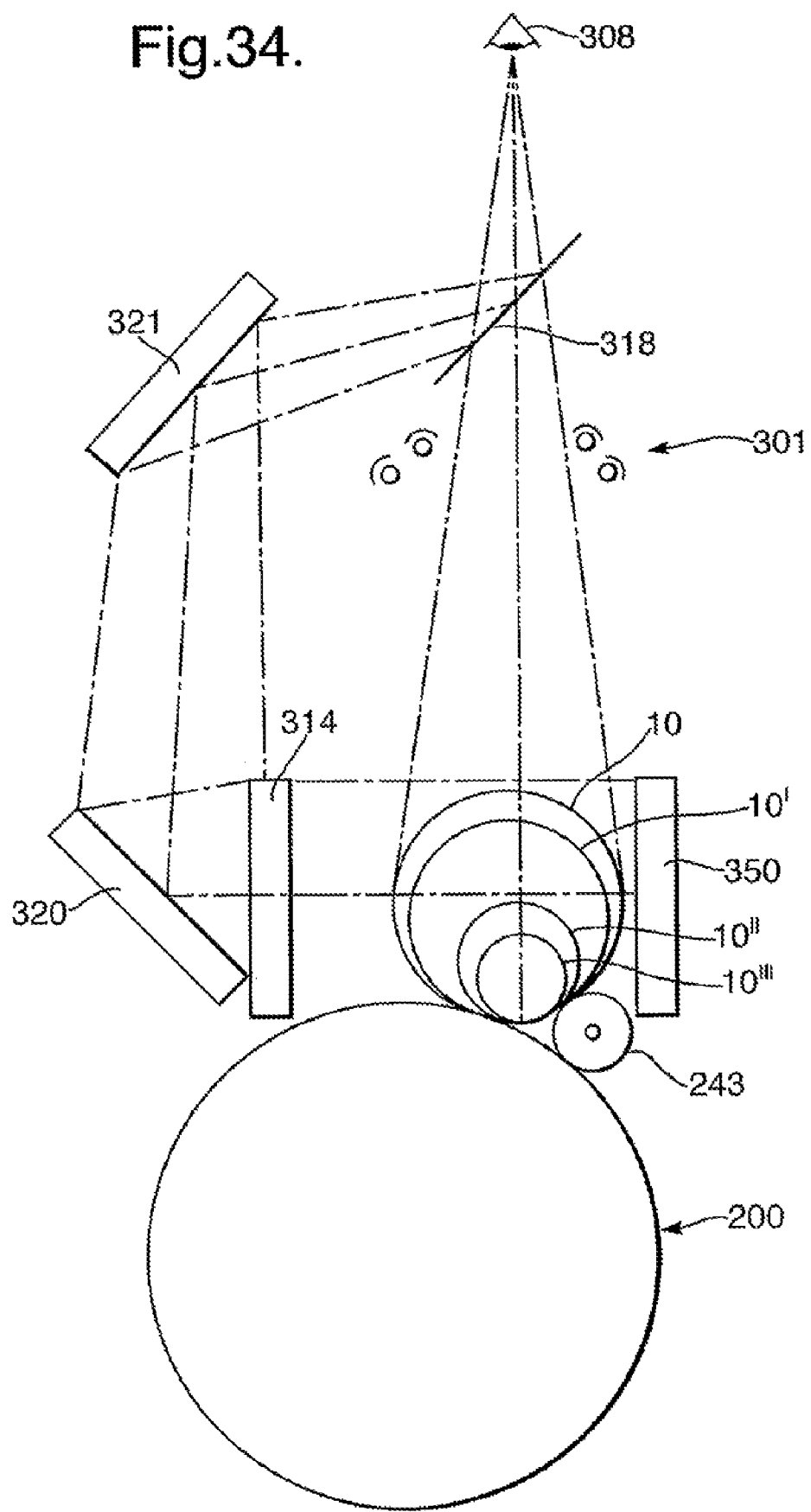
FIG. 34 is a principle sketch of an eight embodiment of the camera-aided viewing device.

A similar situation is present with the embodiment of FIG. 34, which is identical to the embodiment shown on FIG. 27, apart from the light source 300 and the retro-reflective background area 313 having been deleted and replaced by a light emitting area, suitably in the form of the panel 350 to form a bright background against which e.g. the object 10 is to be viewed by the single camera 308 to provide for e.g. detection of object contour.

Figure 35:
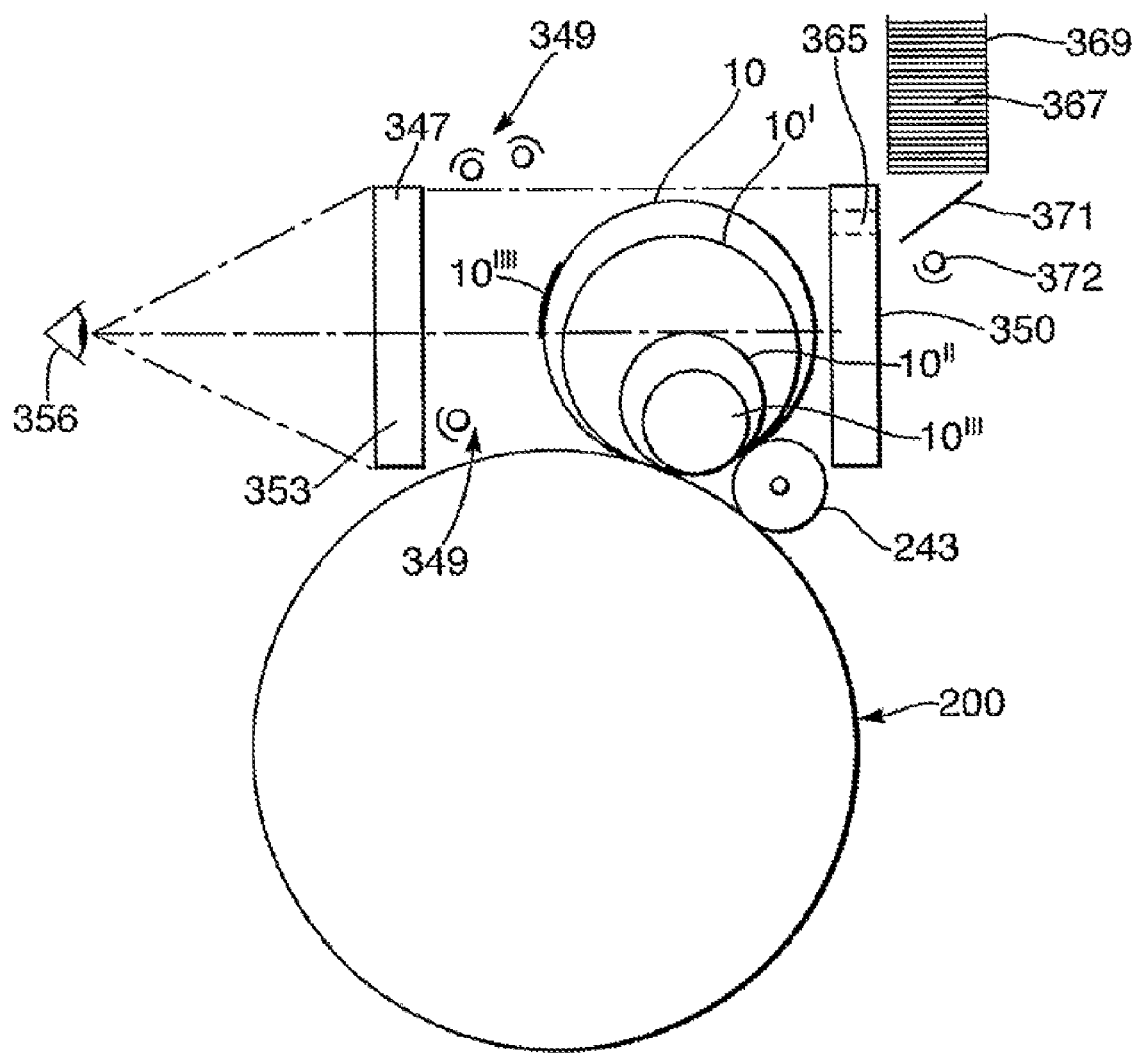
FIG. 35 is a principle sketch of a ninth embodiment of the camera-aided viewing device.
Figure 36:
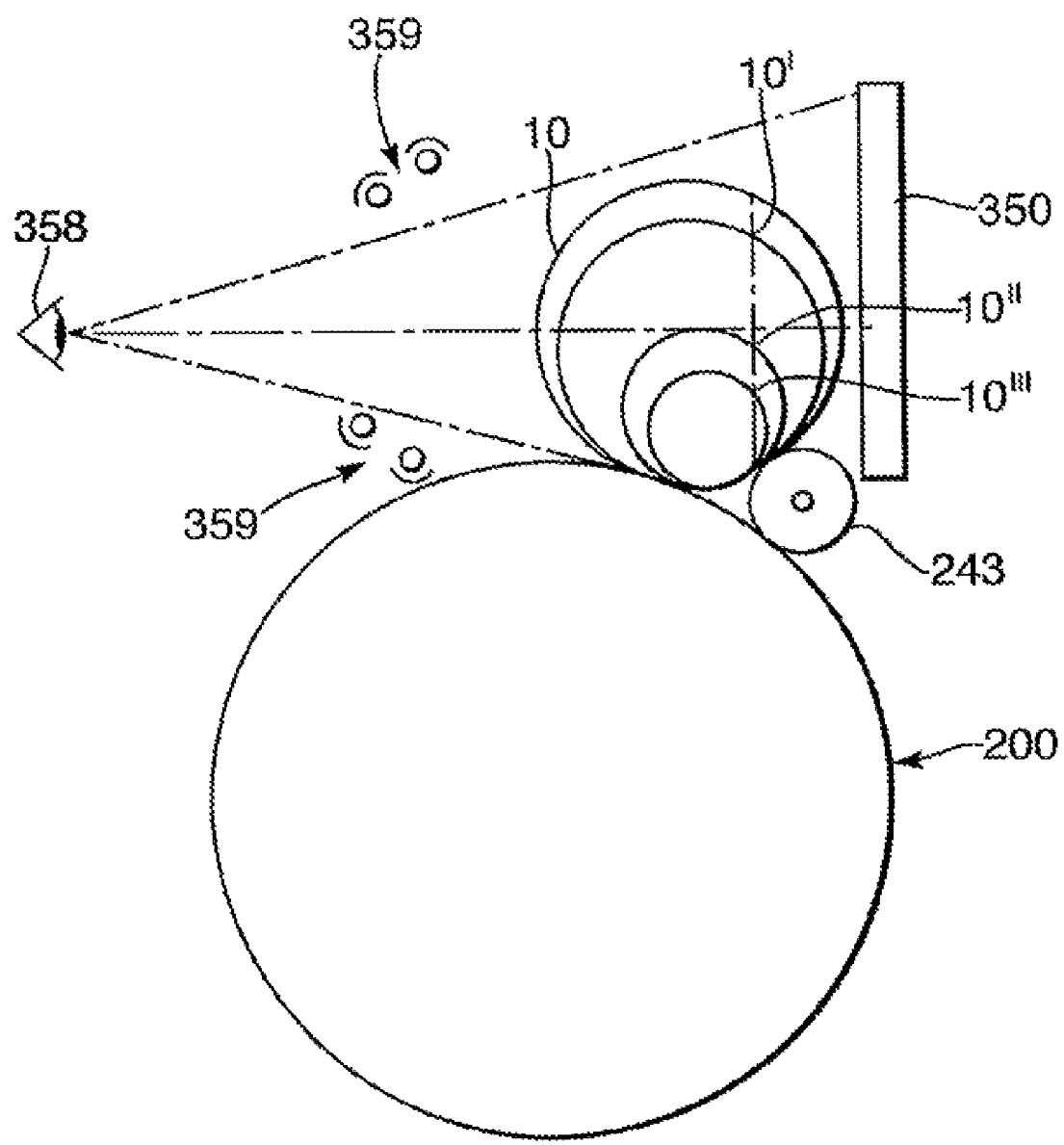
FIG. 36 is a principle sketch of a tenth embodiment of the camera-aided viewing device.

The further embodiments depicted on FIGS. 35 and 36 are also related to the use of a light emitting panel 350 to form said bright background and against which camera viewing of an object can be made, as will be further explained.

FIG. 35 is a modification of the embodiments of FIG.30. It is noted that the lens 353, which is suitably of same type as lens 347 in FIG. 30 or lens 314 in other drawing figures, is present in order to let a single camera 356 view and detect object contour, e.g. contour of object 310 against the panel 350 which in this embodiment constitutes the first light source. The second light source is that labeled 349, which could be constituted by two or more light sub-sources. The camera 356 uses the lens 347 to enable viewing through use of parallel rays, in order to get as accurate contour image of the object as possible. The light source 349 is activated when the camera is to view and read identity features, like e.g. bar code 309', located on the object. Suitably, panel 350 is then not exhibiting a light emitting surface or background area, or its light emitting intensity could suitably be reduced. Other structural details shown on FIG. 35 will be further explained later with reference to FIG. 39.

FIG. 36 is an embodiment with a single camera 358 which is capable of viewing an object, e.g. an empty beverage bottle or can 10; 10'; 10'' or 10''' against a light emitting background area, such as the panel 350 as described earlier. In order for the camera 358 to view and read identifying features located on the object, e.g. a bar-code 10'''' on object 10, it is preferable to use a second light source 359. When the light source 359 is activated, it would be preferable, though not essential, to reduce light intensity from the panel 350 or even turn off emission of light from the panel 350. The light source 359, which is similar or identical to the light source 349, could be constituted by two or more sub-sources.

From a viewing of FIGS. 33-36 it will be appreciated that turning of the object to be inspected, e.g. to suitably find an identifying feature to be detected, is made by means of the object supporting means 220, 220, 243 or 260, 262, 270, 271, 273, 273' as shown on in more detail on FIGS. 26 and 32, respectively.

Further, it could be of advantage to let the first and second light sources, e.g. 300, 301; 300', 301; 342, 344; 348, 349; 350, 301; 350, 354; 350, 349; 350, 359 have different spectral range or composition. Also, it would be possible to have the second light sources 301; 344; 349; 359 composed of two or more sub-sources. Further, the sub-sources could have different spectra range or composition, either all different, different in pairs or in groups. Such features of the light sources and possible sub-sources are of importance to be able to detect e.g. identifying features on the objects appearing e.g. with different colours, different reflective properties etc.

Further aspects of the invention are now to be explained with reference to FIG. 37. In the particular case of the embodiments of FIGS. 25, 26 and 28, as well as FIG. 33, it would be suitable to split the camera video image in two with a part 360 related to the first region 306 and another part 361 related to the second region 307. In the embodiments of FIGS. 27 and 34 it may be visualized the possibility of dedicating half of the camera video image to region 306 and the other half to region 307, or alternatively have alternating full video images of regions 306 and 307. For the embodiments of FIGS. 29, 30 and 36 the choice is alternating full video images only.

Camera viewing of the first region of the object 362 related to its contour 363 can in addition include observation or rather recognition of mere presence or absence of said identifying features 364, e.g. bar code located on the object.

The focus of the camera will not be exactly on the features 364, but the camera will at least sense or detect with relation to the partial image 360 whether the features 364, here labeled 364' are indeed present or not, although on the partial image 360 appearing "blurred" or a bit out of focus. If the features 364 are not visible on the image part 361, but visible on part 360, this will indicate necessity to rotate the object one way or the other through a maximum angle of 180°. The comparison between the two images 360 and 361 in this respect has some impact on the required amount of rotation of the object in order to be able to view and read the feature 364 properly in region 307, and consequently has also importance with regard to processing time in order to find the feature 364, read and record it.

When using in this manner a single camera for camera viewing of both said first and second regions, the camera has preferably, but not necessarily its image field subdivided into said at least two partial images 360, 361, the first partial image 360 being dedicated to object contour detection and/or detection of presence or absence of said identifying features, and the second partial image 361 being dedicated to observation and reading of said identifying features.

It is readily understood that the principle of detecting presence or absence of identifying features in region 306 and the need for rotation of the object is equally well useful when the camera switches between viewing regions 306 and 307.

Operational Safety Means

As indicated in the introductory part of the specification it is important also to focus on safety aspects when using an apparatus as extensively disclosed in the present specification and on the drawings, in particular to avoid injury to persons operating the apparatus or to avoid functional breakdown or jamming of the apparatus.

Therefore, the invention is in this aspect focused on implementation of safety measures which are provided from actions obtained by operating a hardware circuit which is adapted to read predefined or dedicated pixels on the sensor matrix of the camera, i.e. reading hardware assigned physical pixels of the camera sensor matrix when a camera image is made.

This will yield a reliable safety measure related to possible operational hazards, thus e.g. preventing a motor from operating through halting its rotation or removing current supply thereto to thereby remove its torque.

This aspect of the invention is therefore through use of camera functionality able to provide an efficient hardware implemented light curtain functionality, as will be more closely explained in the following description with reference to FIGS. 37a, 37b, 37c, 40a, 40b and 46.

In the present embodiment there is used a camera image, such as e.g. image 360 or 385 for detection of so-called "border crossing", i.e. an event in a field of view of the camera.

As indicated above, it is important to provide for personnel or an operator (e.g. a supermarket customer) operational safety of an apparatus, e.g. a reverse vending machine, and also protect in such apparatus machinery, having movable parts, against externally created interference that could cause operational damages or personal injuries, or operational or personal hazard. With a light curtain functionality it is possible to disable operation or stop the machinery altogether immediately and inhibit further operation until the cause of such operational disruption has been attended to.

Figure 37A:
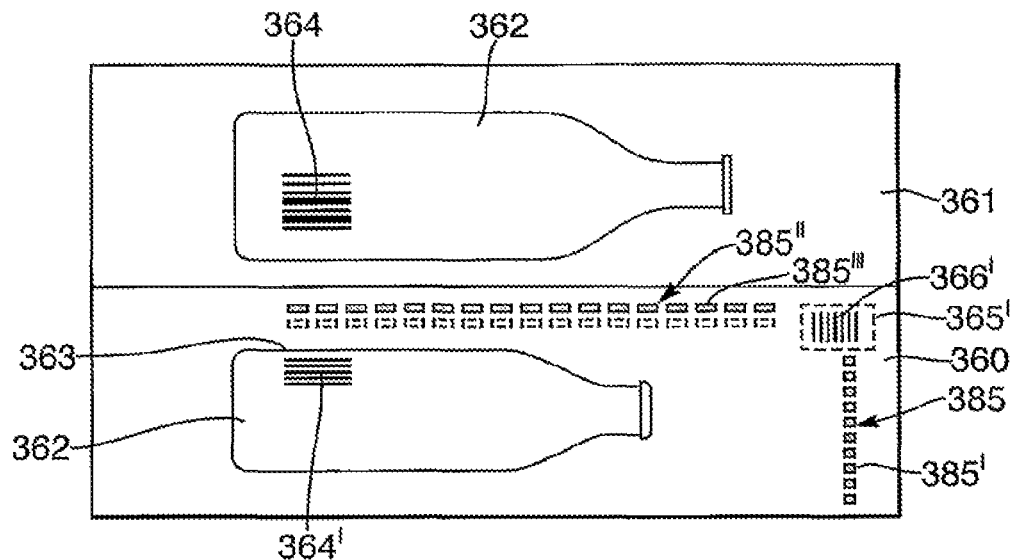
FIG. 37a shows a camera image with two image parts.
Figure 37B:
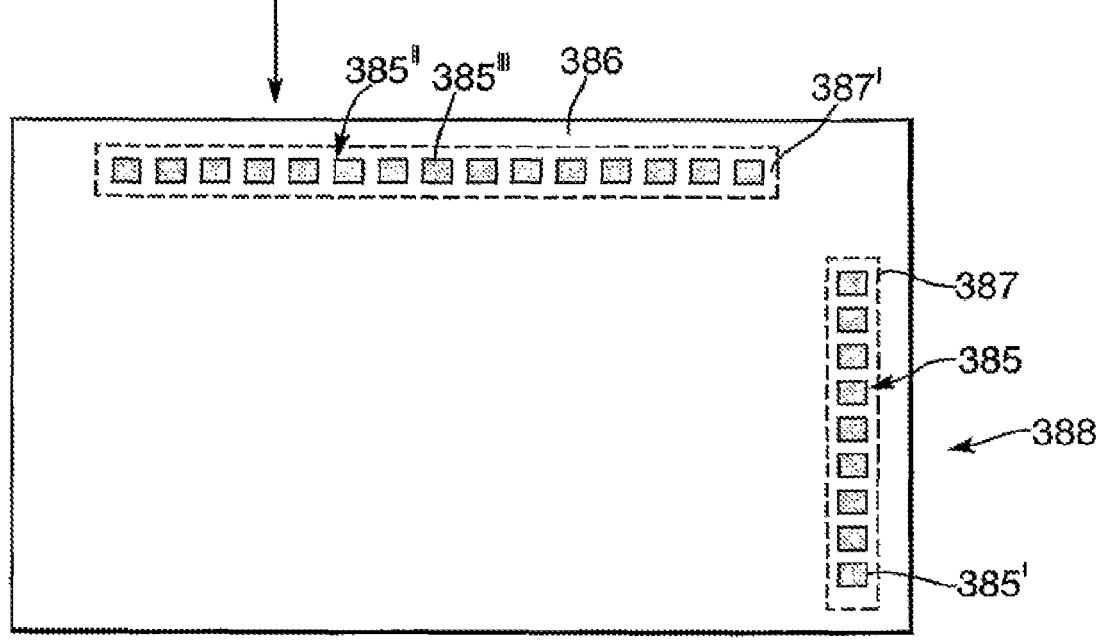
FIG. 37b shows a camera surveillance image with a set of dedicated camera image sensor matrix pixels indicated.

With reference to FIGS. 40a and 40b, as well as FIGS. 37a and 37b there is on the bright or light emitting background 313; 350 located at least one array or column 385 of repeatedly occurring dark markings 385', e.g. black squares at an in-feed region receiving objects in direction 388 at which objects are fed into the apparatus for viewing, detection, turning and sorting, as previously disclosed. Further, there may on the background 313; 350 be located at least one array or row 385" of repeatedly occurring dark markings 385'". At least one such row may be useful if the entry or in-feed region causes objects to be fed in a direction 388'. However, if the insertion opening 425 is so configured that it may be possible for a human hand to be inserted there-through and into the viewing chamber, so as to move into the viewing chamber essentially from above and thereby avoid obscuring viewing of the array 385, the array 385" is present to assist in providing additional light curtain functionality.

It has also been indicated by dotted lines on FIG. 40a that e.g. two columns of markings and two rows of markings could be possible, although the number of rows and/or columns could be more than two.

Alternative or supplementary to the interspaced markings 385', 385'" indicated on FIG. 40a, there could be located markings 395, 396 and 397 in the form of solid lines, as indicated on FIG. 40b.

It is possible to have a column or row configuration of markings or a joint column and row configuration.

Figure 37C:
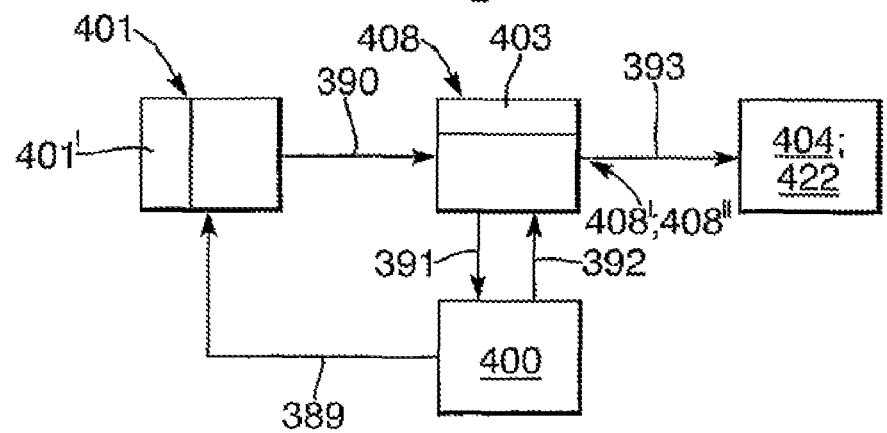
FIG. 37c shows a simplified circuit diagram forming part of the block schematic diagram in FIG. 46.
Figure 47:
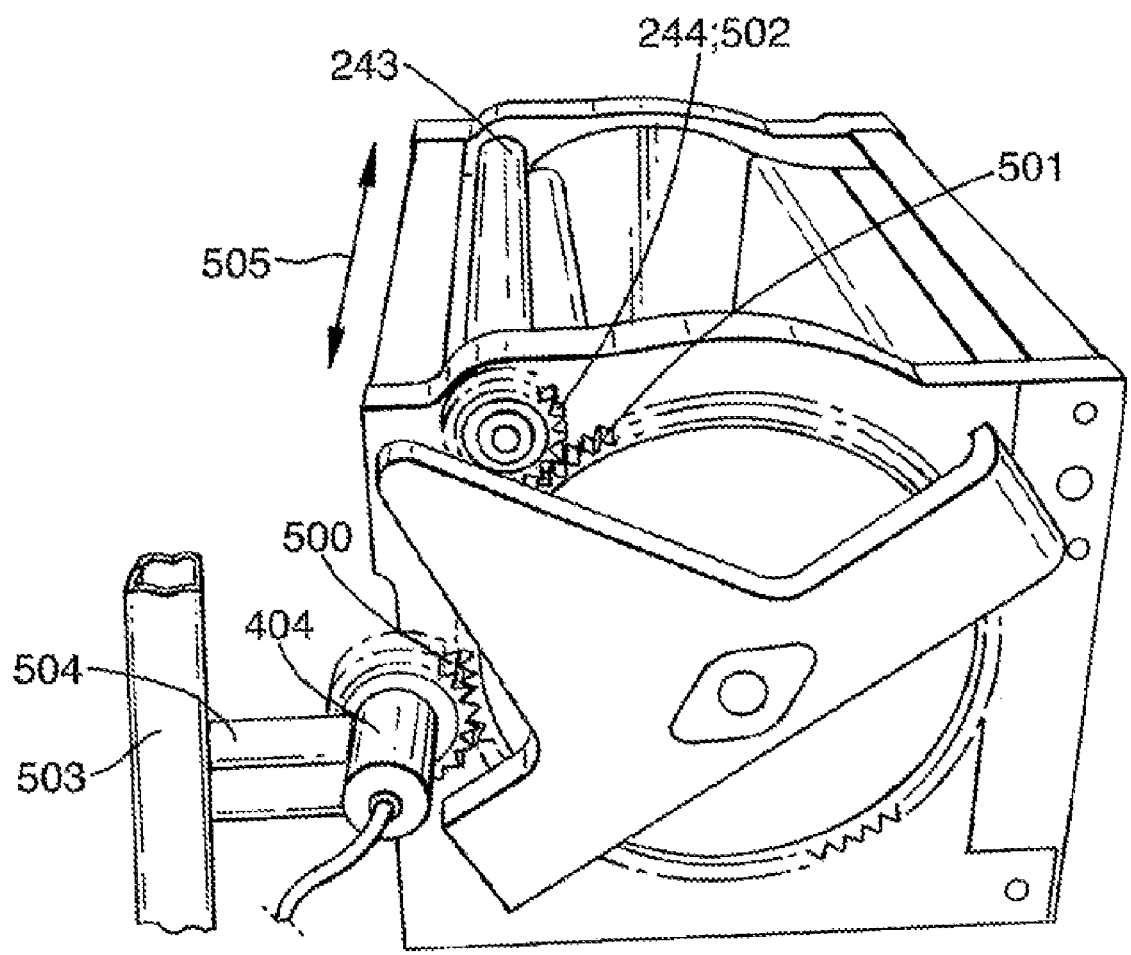
FIG. 47 is a principle sketch to illustrate drive means for rotatably driving a drum in said object supporting, rotating, sorting and conveyor means.

FIG. 37a exhibits two half-images 360 and 361, as previous discussed, whereas FIG. 37b exhibits a generalized full image 386 as provided by the available pixels on a camera image sensor matrix 401' (see FIG. 37c). The dotted line 387 and/or 387' on FIG. 37b (not shown on FIG. 37a for clarity reason) denotes, relative to the camera image, a fraction or fractions of matrix pixels being a selected part of the available sensor matrix pixels. Said fraction 387 of sensor matrix pixels is dedicated to detection of the array or column of markings, as well as any events observable by said fraction of pixels and which could trigger an action, such as stopping operation of a motor, e.g. motor 404 or 422 with reference to FIGS. 46, 47, 48, 49 and 51. Similarly, said fraction 387' of sensor matrix pixels is dedicated to detection of the array 385" or row of markings, as well as any events observable by said fraction of pixels and which could trigger an action, such as stopping operation of a motor, e.g. motor 404 or 422 with reference to FIGS. 46, 47, 48, 49 and 51. As indicated above, the arrays 385 and 385" of markings 385' and 385'" could both be present, yielding that both fractions 387 and 387' will be active for detection of markings and observable events.

A background area 313; 350 is located in the camera field of view, and as shown on e.g. FIG. 40a, said background area in a part thereof exhibits the array 385 of distinguished markings 385'.

As indicated on e.g. FIGS. 26 and 40a, and derivable from FIG. 46, the background area 313; 350 is located in a camera viewing chamber of a reverse vending machine. The chamber or input receiving area 210 (FIGS. 6-9) has entry opening (see 425 on FIG. 51) into which an object 10 in the form of an empty beverage container to be viewed by the camera, is insertable. From FIG. 40a is noted that the array 387 of markings is located at an entry opening or region 425 of said viewing chamber 210. The in-feed direction for objects is indicated by reference numeral 388 on FIG. 37b. As indicated on FIGS. 37a, 37b and 40a the array of markings is in a predefined pattern, suitably a column 385 of mutually spaced markings 385'. However, as disclosed above there could be as an alternative or in combination with the pattern 385 an additional predefined pattern 385" of mutually spaced markings 385'" extending as e.g. an upper row, to provide an addition light curtain and to safeguard against any safety hazards caused by someone trying to put e.g. a hand into the viewing chamber from above, as e.g. indicated by reference numeral 388'.

As indicated above, the fraction 387 and/or fraction 387' of sensor matrix pixels 401' in the camera 400 will be dedicated to providing an image of said markings 385' and/or 385'" against said background area. The fraction 387 and/or fraction 387' of pixels will be readable by an operating unit 408, the response of which is dictated by its hardware functions and inputs to the unit 408. The operating unit 408 is operatively linked with the camera 401 to read said fraction of sensor matrix pixels. Further, the operating unit 408 is linked to a digital processing and control unit 400, said unit 400 controlling operation of the camera, i.e. when a camera image is to be taken.

The operating unit has a set of stored reference pixel signal values which are respectively related to pixels in said fraction of sensor matrix pixels, and which are related to said background area 313; 350 and said array 387 of distinguished markings thereon.

The operating unit 408 is capable of comparing a read pixel signal value from a respective pixel in said fraction of pixels with corresponding reference signal value assigned to such respective pixel, and to output respective comparison signal, however said operating unit 408 having an output 408'; 408"

capable of changing signal state of delivered signal 393, suitably into a disabling or deactivating signal when said comparison signal or for that matter a set of such comparison signals departs from a predefined condition.

The signal 393, when in a disabling or deactivating state, is effective to cause disablement or halted operation of functional equipment 404; 422 having movable parts, e.g. a motor and its motor controlled parts. In a preferred mode of the invention, the operating unit 408 will, when the comparison satisfies the predefined condition, provide a signal 393 which enables the equipment to remain in operation. Such equipment could e.g. be found in a reverse vending machine as disclosed in the description and shown on the drawings.

As indicated above, the operating unit 408 is made to execute hardware functions, and the operating unit can be of a logic network of a type well known to any skilled person in the art and connected to execute the required functions. The operating unit can made from a plurality of discrete functional building blocks or a single integrated circuit (IC) as an application specified integrated circuit (ASIC), e.g. as a so-called Gate Array, or as an implementation in a programmable circuit, so-called Field Programmable Gate Array (FPGA).

The operating unit 408 may include a watchdog timer 403 which is designed to check that reading of pixel signals from said fraction of pixels and comparison with reference pixel signal values are made at a minimum rate of iteration. The reading of pixels is initiated from the processing and control unit 400. If said minimum rate of iteration is below a set value, the operating unit 408 may output said signal 393 in a state thereof causing disablement or shut-down of operation of equipment controlled by the unit 408.

The signal 393 in a deactivating state will normally be present until such a point of time when a new surveillance image taken meets all preset criteria for not issuing such deactivation type of signal.

In order to provide proper operation, it is considered that there should be a synchronization of the camera and a light source providing a bright or illuminated background area. Preferably there is used a light reflective material 313 at the camera field of view onto which said dark squares 385' have been applied. However, if the background 350 is a back-lit or illuminated panel, it could be visualized synchronized operation thereof with the operation of the camera.

In order to provide a proper safety function, it is appreciated that surveillance images of the chamber or area 210 will have to be generated frequently. Using the camera 401, it will by means of the operating unit 408 and with aid of the unit 400 be checked first if a complete bright line exists, i.e. all matrix pixel values above a predefined dark level threshold. If this is the case, there will be a search for alternating dark and bright areas along a predefined column, such as column 385. In a preferred embodiment, the detected image of dark areas 385' should be within minimum and maximum length requirements to pass acceptance. Further, the bright areas must be of a minimum length before accepted. Also, the image must end with an accepted bright area. Finally, an accumulated number of accepted dark areas must equal a predefined number.

FIG. 37c is a system block diagram specifically related to the light curtain functionality, and should be considered essentially as part of the block schematic shown on FIG. 46. The camera 401 is controlled by a digital processor 400 associated with the operating unit. This processor is in FIG. 46 denoted as a processing and control unit 400. Line 389 denotes camera control, and the camera delivers image data signals on line 390 to the operating device 408. The operating device 408 has a watchdog timer 403 connected thereto. The unit 400 suitably controls triggering of camera imaging, as well as synchronization of the camera and any background illumination. Image data are conveyed from the operating unit 408 to the processor 400 via line 392, and the processor 400 provides the operating unit 408 with certain control signals via line 392. The processor 400 is suitably the main processor of the overall system, although this is not necessarily so.

Most importantly, to avoid the drawbacks known from prior art and as mentioned in the introduction, the dedicated set of sensor matrix pixels forming a fractional part of the total number of sensor matrix pixels is not selected through use of software, but is instead related to a limited number of physical pixels or elements on the camera image sensor matrix. As the light curtain function is important from an operational safety point of view, it is therefore absolutely essential that the light curtain function is not at ah software based.

Figure 38:
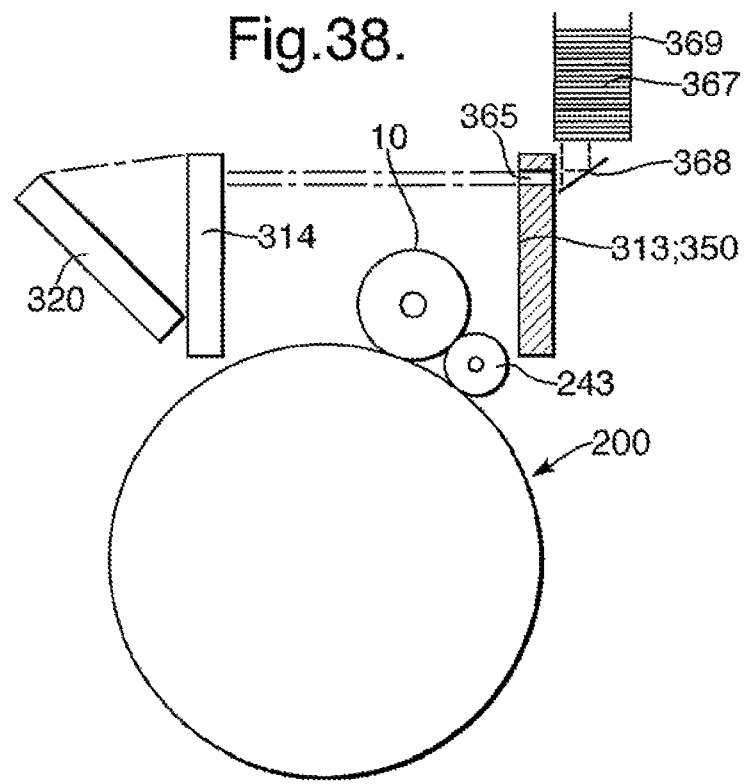
FIG. 38 is a principle sketch to illustrate camera reading of bar-code on a token in a token storage device.
Figure 39:
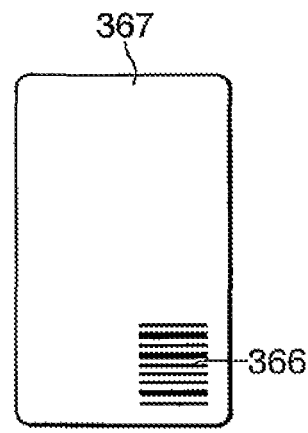
FIG. 39 is an exemplifying token.

From FIG. 38 it is noted that the bright background 313; 350 has an aperture 365 therein in order to let the camera read via said aperture illuminated marking 366 on a token 367 to be dispensed in a controlled manner. Such token 367 is configured to be related to observed objects, e.g. 10; 10'; 10''; 10''' which are supported and to be removed by an object supporting means, e.g. of a type shown on FIG. 26 or FIG. 32.

Suitably, said camera is configured to alternately, selectively or repeatedly a) cause detection of object contour, said light curtain related markings 385' and 385''' and events related thereto, and said token marking 366, and b) cause reading of identifying features, e.g. 10'''' or 364 located on the object 10; denoted on FIG. 37a by reference 362.

All embodiments of FIG. 25-36 can be used with the light curtain function, but the light curtain functionality according to the invention is not limited to the configuration shown on these drawing figures.

A Token System

As noted from FIGS. 26, 35, 38, 40a, 40b, 41 and 42 the background area, e.g. 313 or 350 may have an aperture 365 therein in order to allow the camera which views the first region 306 to detect illuminated, pre-printed or pre-provided marking 366 on a token 367 which is arranged to be dispensed in a controlled manner from stack of tokens. Such a token could be related to information such as both a token serial number and a return or redemption value of an object or objects which have been viewed and considered by an RVM. On image part 360 it is indicated how the camera may view such marking, denoted by 366' through the viewable aperture 365'.

In order to obtain an efficient reading of such marking 366 without using an additional light source, the markings on the tokens are suitably made from a retro-reflective material. Alternatively, the token itself could be made from a retro-reflective material and the markings in such a case from non-retro-reflective material.

As shown on FIGS. 38, 41a and 42 said markings are camera readable via a mirror 368 located adjacent the aperture 365 in background area 313; 350. This may be a practical solution if tokens, e.g. in the form of cards, are dispensable from a dispenser unit 369. If cards are merely to be inserted into a guide 370 in the front of a RVM (see FIGS. 26 and 41b) to be read by the camera and then withdrawn, the card guide may be located at the back of the light reflective area 313 or the panel 350, so as to place the card with its face having markings 366 parallel to the back of the area 313 or panel 350.

In case a light emitting background panel 350 is used, the panel 350 constitutes the first light source which is primarily dedicated to assist camera viewing of object contour. However, light from the second light source will not necessarily impinge upon the marking 366 of a token 367 viewable through the aperture 365, but if such light in fact impinges upon the marking, it may either be non-parallel light rays or insufficient light in order for the camera to clearly see and cause detection of the markings. In such a case, it is suitable to use an optical beam splitter 371, as depicted on FIG. 35 and a separate light source 372.

In the case of using an optical beam splitter covering part of the camera field of view, as shown in FIGS. 25, 26, 28 and 33, the camera 308 is suitably configured to take an image of both of said first and second regions simultaneously. However, image taking may just as well be based on taking an image of said first and second regions alternately, or selectively taking a partial image of said first region or said second region.

In the case where an optical beam splitter covers completely the camera field of view, as seen from FIGS. 27 and 34, the camera 308 is configured to take an image of both of said first and second regions simultaneously to form a two part image, as e.g. shown on FIG. 37a. However, it would also be feasible to consider taking a full image of said first and second regions alternately, or selectively taking a partial image of said first region or said second region.

In the embodiments of FIGS. 29-31, as well as FIGS. 35 and 36, the camera 340; 345; 351; 356; 358 could suitably take images alternately or selectively, although it could be visualized taking two partial images of the viewing region simultaneously, one dedicated to contour recognition and the other to identifying features on the object. The embodiments of FIGS. 30, 35 and 36 in addition provides for reading of marking on a token, as disclosed e.g. in relationship to FIG. 38-42.

It has been disclosed above that the second light source 301, or for that matter also the light sources 344, 349 and 359 can be constituted by a plurality of light sub-sources, and the light source 301 has been indicated to have e.g. four such sub-sources 302-305, although there could be fewer sub-sources or more. For the other sources 344, 349 and 359 three or four sub-sources have been indicated, without labeling each. The reason for more than one light sub-source is that light reflexes from the object or position of the light sub-source relative to the identifying feature on the object may cause the reading of the feature to be difficult or even impossible. In view thereof the light sub-sources are suitably selectively activated, although activation would be possible individually, in pairs or in groups, or in a cycle.

FIGS. 43-45 illustrate a preferred card dispenser 369 to be used for dispensing tokens, e.g. cards 367. The dispenser 369 has a dispensing outlet 373 for dispensing cards 367 one-by-one from a stack of cards contained in a storage compartment 374. The markings 366 on the cards 367 are viewable through an opening 375 in the bottom of the dispenser. A pusher member 376 is provided to push out cards one-by one by a reciprocal motion of the pusher member or slide 376, the reciprocal motion being provided by a controllable motor 377 having control wires 378 for controlling power to the motor. Suitably, the motor 377 has a pinion (not shown) in engagement with a rack 379 on the pusher or slide to enable the reciprocal movement thereof.

RVM Operational System Overview

FIG. 46 depicts an overall system in which the various aspects of the present invention are implemented.

The reverse vending machine (RVM) has said processing and control unit 400 which receives video data from the camera 401 via a video analyzer 402. The camera 401 is also linked to the operation unit 408, and the operation unit includes the watchdog timer 403 and a motor control. The motor #1 and its control, denoted 404, are related to the drive of the supporting means 325, 327, or the unit 333 as disclosed earlier. A motor overload sensor 405 is also provided to inhibit operation of motor #1 in case of jam not detected by the operational unit 408 or a jam detector 406. The sensor 405 could be in the form of a pressure sensitive bar, or the roller 243 could have its weight sensor 253 (in FIG. 46 denoted by 419) modified in order to also indicate pressure against the roller caused by a jam due to an object not fully located in the recess or space 222.

The operation unit 408 is, as disclosed earlier linked with the camera 401 and the processing and control unit (processor) 400, and in the present example the unit 408 controls the motor controls 404 and 422 directly, although such control could be via the processor 400.

As indicated earlier, optically readable cards will normally be read by e.g. camera 401. However, if a card is a magnetic readable/writable card or an r.f. readable/writable card, there will be the need of a card reader/card encoder unit 411. The card dispenser 361 as disclosed earlier is on FIG. 38 denoted by 412.

Suitably, the tokens are ready made, pre-coded cards, like the cards 367 which are dispensable one by one from the dispenser means 369; 412 (FIG. 46) and which upon the feed-out from the dispenser 412 via output 412' is code-read by a code reader/encoder 411, in particular if the card is a magnetic stripe or r.f. card. Alternatively, if the card is an optically readable card, the card is read by the camera 401 via aperture 424 and inclined mirror 424' as more closely disclosed in connection with FIGS. 38, 41a and 42 (see references 365 and 368).

If the card is a magnetic stripe card or an r.f. card and with no information on the card when it is located in the dispenser, the code reader/encoder 411 will be able to encode the card with a card code, such as e.g. a serial number or other identity, or the combination of a card code or serial number or other identity and a redemption value to be rewarded or paid, as the cards are fed out from the dispenser one-by-one.

If the cards to be used for reward of empty beverage containers deposited in the RVM are not to be delivered from a card dispenser, such token could be a personal token which the customer brings with him to the RVM and uses to transfer card identity data from the card to the RVM. If the card is an optically readable card, it can be read by the camera 401 and as indicated further by reference 411' when inserted into a slot (see reference 370; FIG. 26) and viewable through an aperture (see reference 370'; FIG. 26) in the light retro-reflective area (see reference 313; FIG. 26). If the card is an r.f. readable card, the card could be readable by an r.f. reader 411", and if the card is a magnetic stripe readable card, the card could be readable by a magnetic stripe reader 411'''.

The cards, irrespective of being optically readable, r.f. readable or encodable, or magnetic stripe readable or encodable, could be in the form of a reusable token, in particular because the cards are in any case validated and after reward has been paid, invalidated. The token could be retrieved from a stack or a band of cards. If a band of cards or a zig-zag arranged band of cards is used, the dispenser 369 (412 on FIG. 46) should suitably be replaced by a conventional type of dispenser for such card arrangement. Also, different type of encoder 411 may be required. In any case, the card should have at least an alphanumerical, machine readable code.

If the token is a card which is optically readable, the card should have a pre-made code thereon, suitably consisting of a bar code or other optically readable code readable by an optical reader such as the camera 401. As indicated earlier, the bar code or other optically readable code is preferably retro-reflective to light. Such configuration of the card makes an additional light source for viewing the code on the card superfluous. Conversely, the card could be made of a retro-reflective material and the bar code be made of a non-reflective material.

The processor 400 will either directly, or via a central computer installation 413 transfer to a rewarding or check-out and payment station 414 information related to a readable token code and information related to said return value. Transfer of information to and from the processor to the computer 413 and the station 414 is suitably via a local area network (LAN) 415. The station 414 has a card reader 416 to read the card before reward or redemption value is paid. The card is then invalidated through use of a token invalidation means 407 associated with the station 414 or through internal operation in the unit 400 and/or the computer 413. In an alternative embodiment the processor 400 communicates with a "tick-off" unit 417, which could be in the form of a mini-computer, such as so-called PDA. This could be a solution useful for a small store, through which there is conveyed to the unit 417 from the processor displayable information such as visible card identity and sum to be paid. Upon payment of the required money, the operator ticks off the particular item displayed, which is then made void or invalid, cancelled in the unit 400 and/or computer 413, and suitably removed from the display on the unit 417.

The RVM has suitably a display 418 to properly guide or inform an RVM user how to operate. If the display is a touch screen, the customer may communicate with the processor 400. The container weight sensor 419 indicated on FIG. 46, which has been described earlier in the context of FIG. 18 as sensor 253, is provided to engage an end 247 of an axle 243' (see FIG. 26) of the roller 243, so as to spot whenever a too heavy beverage container is fed into the RVM through an opening 425 on the RVM. The term "too heavy" in this context is meant to imply that the unit 400, upon receiving information related to shape and identity features, will compare these data with library data in the unit 400, and thereby determine whether the object in fact should weigh less or not. This has been disclosed in more detail earlier. Also as indicated, the weight sensor could suitably form or supplement the jam sensor 405.

An interlock-mechanism 420 is provided for safety reasons. The mechanism is suitably a set of sensors and switches to ensure that the RVM cannot be operated unless all units are in proper place and all cabinet panels are in proper mounted position and cabinet doors are locked.

A power supply 421 is provided, suitably linked to power consuming units via the unit 400.

A motor and control unit 422 is provided to cause the volume of a collection container 426 to be adjusted by winding or unwinding a flexible side and bottom 426', However, although FIG. 51 shows a collection container 426, it would be understood by the average expert in the art that other operational equipment could be installed and operated instead of the collection container. Such equipment could include one or more from the group of: conveyor; pusher unit; rotation means; compactor; disintegrator; sorter means. The positioning and evidently the configuration of such equipment in cooperation with the motor 422 could be substantially different from that of the collection container 426. The collection container is particularly suitable for heavier objects, e.g. bottles of glass.

Reference numeral 423 in FIG. 46 denotes a position sensor which is used to detect rotary positions of the drum 220, or the plunger 270, and will be described in slightly more detail in connection with FIGS. 50*a* and 50*b*.

The reference numeral 100 denotes generally a storage compartment for receiving objects delivered from the supporting, sorting, conveying and push-out unit 200. The storage chamber or compartment 100, as shown also in FIG. 51 has been extensively disclosed earlier in the present disclosure, see disclosure related to FIGS. 1-24, and FIGS. 2-8 in particular.

Electro-Mechanical Drive Device

FIGS. 47, 50*a*, 50*b* and 51 show that the unit 200 is powered by a motor 404 via a gear 500 which engages a gear 501 on the unit 200 to turn the drum 220 and in so doing also moving the element 223. The roller 243 is forcibly moveable through interaction between a small gear 502 and the substantially larger gear 501. Motor 404 is fixedly attached to the framework 503 of the RVM via brackets 504, whereas the unit can be pulled out entirely from the RVM cabinet 428 (see reference 250 on FIGS. 18 and 19) for cleaning, as indicated by arrow 505, and be pushed into the cabinet again after cleaning for gear engagement between gears 500 and 501. No electrical parts are present on the unit 200, just mechanical parts which stand wet cleaning, and even high pressure wet cleaning without any problem.

Thus, it is clearly seen that the advantages offered by the present invention reside in that the unit 200 is connected via a mechanically separable power transfer coupling formed by gears 500 and 501, the gear 500 being operated by the motor 404 which is stationary fixed in the cabinet 428. Thus the electrically powered drive 404, 500 is located separable from the unit 200 and its gears 501, 502.

Figure 48A:
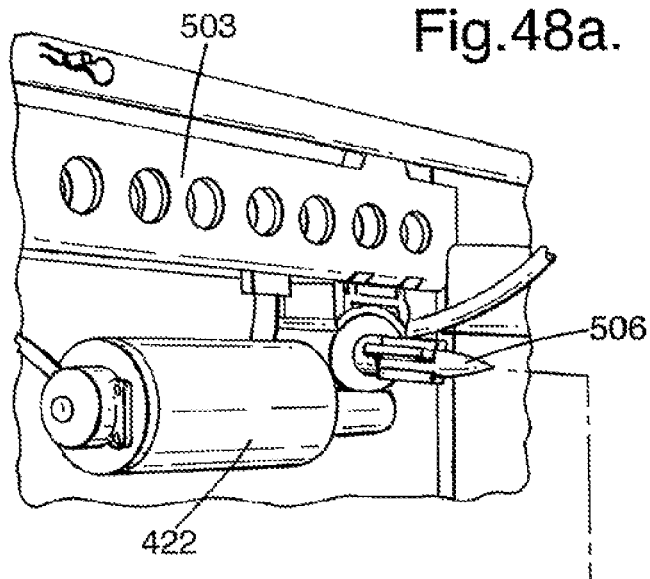
FIGS. 48a and 48b are principle sketches to illustrate a mechanical drive coupling between drive means (FIG. 48a) and a handling device, e.g. a "soft-drop" storage container (FIG. 48b)
Figure 48B:
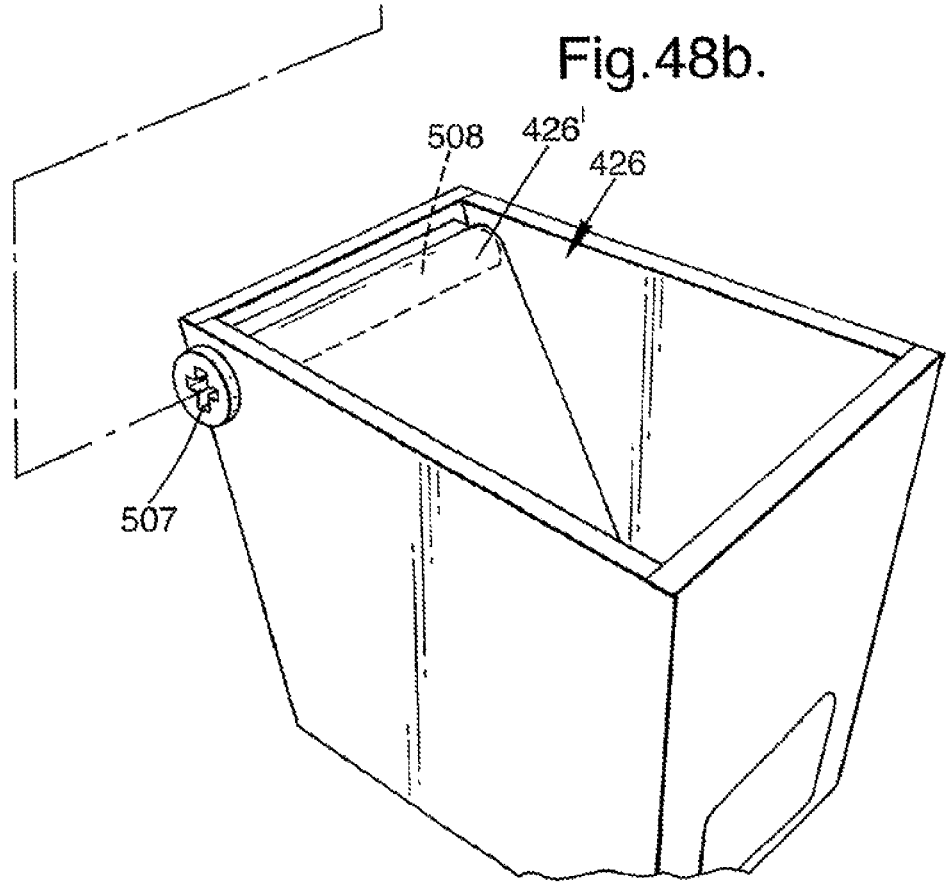

FIGS. 48*a* and 48*b* show a collection container 426 powered by a motor 422. The motor 422 has in a non-limiting example a winged male, spindle-like member 506 which is configured to fit in a releasable manner into a winged, female member 507 on a drive shaft 508, the drive shaft 508 in this non-limitative example to be use for winding or unwinding the flexible side and bottom 426'. The container 426 can be pulled out of the RVM cabinet 428 for emptying and cleaning, and pushed into the cabinet again for engagement between the members 506 and 507. The motor 422, like motor 404 is suitably fixedly attached to the framework 503 of the RVM cabinet or to the cabinet wall or any suitable stay in the cabinet. When the unit 200 or the container 426 are in position in the cabinet and with a cabinet front door closed, there will be full engagement between the power gear 500 and the gear 501 (see element 244 on FIG. 10), and similarly between members 506 and 507. The wing configuration on members 506 and 507 ensures that full rotational locking engagement is provided.

Figure 49A:
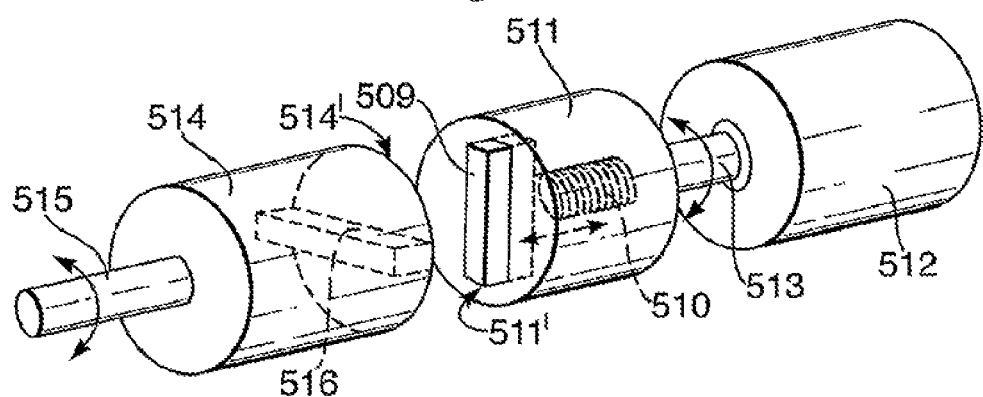
FIG. 49a shows in principle an alternative mechanical drive coupling.
Figure 49B:
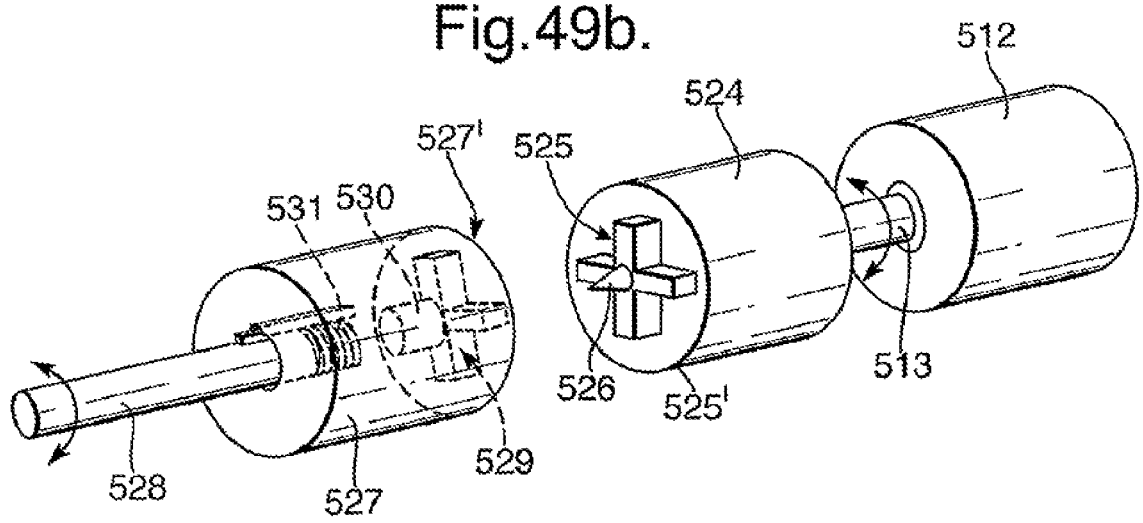
FIG. 49b is a modification thereof.

Instead of the male/female coupling 506/507 on FIGS. 48*a* and 48*b*, a male/female coupling as shown on FIG. 49*a* or 49*b* could be used. Suitably, the female part of the coupling would be on the handling unit side, and with the male part at the drive-motor side, although the arrangement could be vice versa.

In the example of FIG. 49*a*, the male part has a spring-loaded plug 509, loaded by a spring 510 in a housing 511 and powered by a motor 512 via a drive shaft 513. The female part has a housing 514 with a drive shaft 515 connecting to a drive mechanism (not shown) located on a handling unit, such as e.g. a handling unit like the unit 200 or 426. The housing has a recess or socket 516 configured to fit the plug 509. It is appreciated that when the handling unit is pushed into the cabinet, the end face 514' of the housing 514 will more than likely abut the end face 509' of the plug 509, as in most cases the plug 509 is not aligned with the socket 516. However, when the motor 512 (fixedly attached to the cabinet or the cabinet framework or stays) starts to operate, the housing 511 with the plug 509 pushed into the housing 511 starts to rotate until the plug is aligned with the socket 516, at which moment the plug 509 will pop out from the housing 511 and into the socket 516, whereby mechanical coupling is established between the motor 512 and the handling unit.

In the example of FIG. 49b, the male part 524 has a four-winged plug 525 with a spike 526, powered by a motor 512 via a drive shaft 513. The female part has a housing 527 with a drive shaft 528 connecting to a drive mechanism (not shown) located on a handling unit, such as e.g. a handling unit like the unit 200 or 426. The housing has a socket 529 configured to fit the plug 525. The spike 526, which is for aligning the male and female parts 524; 527 fits into a recess 530 in the female part 527. When the handling unit is pushed into the cabinet, the end face 527' of the female part 527 will more than likely abut the end face 525' of the plug 525, as in most cases the plug 525 is not aligned with the socket 529. The female part 527 will thus be pushed backwards about and along the shaft 528 against action from a spring 531. However, when the motor 512 (fixedly attached to the cabinet or the cabinet framework or stays) starts to operate, the part 524 with the plug 525 starts to rotate until the plug is aligned with the socket 529, at which moment the female part 527 will move by spring force towards the male part 524 and allow the socket 529 to be mechanically engaged with the plug 525, whereby mechanical coupling is established between the motor 512 and the handling unit.

If required, releasable locking means, suitably easily reachable by maintenance staff, could be provided to fully lock units like those labeled 200 and 426 in position relative to the RVM cabinet.

As indicated on FIG. 46, sorter or drum rotary position detectors 423 may be provided. FIG. 50a shows position detectors 517 and 518 interacting with markings 517', 518' on the drum cog-wheel 519. The detectors may be of a magnetic type detecting metal elements constituting said markings. The markings may be of an optical type if the detectors are of optical type. In FIG. 50b optical detectors 520, 521 interact with a code-disk attached to the rotation-shaft 523 of the drum.

Modification of the various elements, means and devices related to the numerous aspects of the present invention would be conceivable within the scope of the invention as defined in the attached claims.

The invention claimed is:

1. Upwardly oriented storage (100) having an interior space (110, 112) for storing height-wise returnable items (10), such as bottles, cans and the like of plastic, glass or metal, said storage comprising:
   a) a bottom (120, 121, 122) and at least one side wall (130, 131, 132), wherein the storage further comprises:
   b) a feed opening (140, 142) arranged
      i) in the bottom or
      ii) in the sidewall and at a relatively short distance height-wise from the bottom such that a substantial part of the storage space is located above the feed opening to accommodate randomly stacked returnable items laying one on top of another, and
   c) a conveyor means (200) adjacent to the feed opening and adapted to force a returnable item towards the feed opening, and
   wherein the storage space has a width dimension (111) that is a multiple of the width dimension or in excess of a length dimension of a returnable item for storage in said upwardly oriented storage, whereby a plurality of returnable items can be accommodated in said interior space as one of more of: substantially side by side, at least in part side by side, and in a random "criss-cross" manner.

2. Upwardly oriented storage according to claim 1, wherein the conveyor means is adapted to effect forced pushing or thrust-like forcing of a returnable item towards the feed opening.

3. Upwardly oriented storage according to claim 1, further comprising an upper part (150) having a substantially unitary and vertically movable top section (151) which by its upwards directed movement provides an increase of the interior space volume, or by its downwards directed movement provides a reduction of the interior space volume, accordingly.

4. Upwardly oriented storage according to claim 1, further comprising an upper part (150) having at least one foldable wall (152) which by its expansions provides an increase of the interior space volume, and by its collapsing provides a reduction of the interior space volume, respectively.

5. Upwardly oriented storage according to claim 1, comprising an overflow opening (160) arranged in an upper part of said storage for providing communication from the interior space to a supplementary storage volume (161).

6. Upwardly oriented storage according to claim 1, wherein at least a part of the bottom (120, 121, 122) is movable for providing a bottom opening for emptying of the storage.

7. Upwardly oriented storage according to claim 1, wherein at least one part of a side wall (130, 131, 132) of the storage is movable for providing an opening for emptying of the storage.

8. Upwardly oriented storage according to claim 1, wherein at least a part of a side wall (130, 131, 132) of the storage is movable for providing a modification of the shape of the interior space (110, 112), particularly for providing an increase of the cross section (11, 113) of the interior space in an area proximal to an opening provided for emptying the storage.

9. Upwardly oriented storage according to claim 1, wherein the conveyor means (200) includes:
   a drum (220) adapted for coupling to a drum drive, said drum being rotary about a central longitudinal axis (221) and having in an axial direction an elongate and radially extending recess (222) adapted to receive a returnable item,
   an elongate element (223) provided in said recess (222), which element (223) is adapted to be movable in a piston-like way in a radial direction relative to said drum between a retracted position and an advanced position,
   an element drive (230) adapted to provide a movement of said element between said retracted position in a secondary rotary position of said drum and in an advanced position in a first or third rotary position of said drum,
   an allocated input area (210) for receiving returnable items to be placed on an upper circumferential part of the drum when the drum is in said first rotary position, which input area is located above said drum, the element drive being adapted to position the element in the retracted position when the drum is positioned in the second rotary position with the recess in the drum facing upwards towards the input area, and
   a first output (224) provided in communication with the storage in-feed opening, proximal to an outer surface level (228) of said drum, and covering an angular interval for the drum rotation that includes the third rotary position, and
   wherein the conveyor means (200) is arranged such that a returnable item having been deposited in the input area and received in the recess when the drum is in the second rotary position with the recess facing upwards towards the input area and the element in the retracted position will be driven out of the recess and towards the first output and into the storage in-feed opening by the element when the drum by its rotation in a first direction of rotation is brought to the third rotary position as the element is moved to the advanced position.

10. Upwardly oriented storage according to claim 9, wherein a recess, limiting means (229) is situated adjacent the recess and adapted to prevent any axial movement beyond the length of the drum of the returnable object/item deposited in the recess.

11. Upwardly oriented storage according to claim 10, wherein the recess limiting means is provided by drum end walls (229).

12. Upwardly oriented storage according to claim 9, wherein the conveyor means further comprises a guide means (241) adapted to retain a returnable item deposited in the recess as the drum is positioned in a rotary position between the second rotary position and the first output or a second output.

13. Upwardly oriented storage according to claim 12, wherein the guide means is provided by a curved plate adapted to a curved outer contour (228) of the drum, and which plate substantially covers the recess opening as the drum is positioned between the second rotary position and said first output or said second output.

14. Upwardly oriented storage according to claim 12, wherein said second output is at a fourth rotary position or at the first rotary position.

15. Upwardly oriented storage according to claim 9, wherein the conveyor means includes a frame into which the drum is rotatably supported.

16. Upwardly oriented storage according to claim 9, wherein the frame includes a cabinet adaptor means (242) for providing movable positioning of the conveyor means in a corresponding receiving means (251) in a cabinet (250).

17. Upwardly oriented storage according to claim 9, wherein an outer surface of the element (223) in the advanced position, particularly when the drum is placed in a rotary position with the recess opening facing an exit, is substantially flush with or outside an outer contour (228) of the drum.

18. Upwardly oriented storage according to claim 9, further comprising a leading means (243), preferably provided by way of a rotatable leading roller, arranged above and proximal to said drum, such that the leading means, by rotation of the drum, contributes to a rotation of a returnable item when the returnable item has been positioned on the drum through the input area.

19. Upwardly oriented storage according to claim 18, further comprising a leading roller drive (224) for driving the rotatable leading roller.

20. Upwardly oriented storage according to claim 19, wherein the leading roller drive provides a drive of the leading roller (243) in a direction of rotation that corresponds to a direction of rotation for a drum and with a peripheral velocity that substantially corresponds to a peripheral velocity of the drum outer surface (228).

21. Upwardly oriented storage according to claim 18, wherein a first bearing support (245) for the leading roller is provided in connection with a weighing cell (246) for determining a mass of a returnable item.

22. Upwardly oriented storage according to claim 21, wherein the conveyor means comprises a frame providing a bearing point for the rotation of the drum, and wherein the weighing cell (246) is connected to the frame.

23. Upwardly oriented storage according to claim 18, wherein the conveyor means includes a frame (240) in which the drum is suspended for its rotation, said drum being adapted for mounting into a cabinet, and wherein the leading roller is adapted for a first bearing point (247) and a second bearing point (246), and wherein the second bearing point has been provided connected to the frame (240) and the first bearing point (247) is provided with a leading roller bearing means (252) connected to the cabinet (250).

24. Upwardly oriented storage according to claim 23, wherein the leading roller bearing arrangement (252) is connected to the cabinet by way of a weighing cell (253) for determining a mass of a returnable item.

25. Upwardly oriented storage according to claim 9, comprising a facility (20) for non-contacting identification of a returnable item positioned on an outer surface of the drum or on the element when the element is in the advanced position.

26. Upwardly oriented storage according to claim 25, wherein the facility (20) for non-contact identification is adapted to employ an energy wave transmitted from the facility and the drum is provided with a directional reflector for reflecting the transmitted energy wave substantially back towards the facility.

27. Upwardly oriented storage according to claim 9, wherein the interior space (110, 112) has a width dimension (111, 113) that is a multiple of a lateral dimension (235) of the recess (222) or a lateral dimension (266) of the input opening (262) of the elongated housing, whereby a plurality of returnable items can be accommodated substantially side by side in the interior space.

28. Upwardly oriented storage according to claim 1, wherein the conveyor means (200) comprises:
   an allocated input area (210),
   an elongate house (260) having a plunger (270) arranged movable in a piston like. way in an interior space (261) lengthwise in the housing between at least a first position and a second position, the house being positioned under the input area and being provided with an input opening (262) for providing communication between the input area and the interior space, which housing at least at one end has an exit (263; 264) positioned proximal to the storage feed opening (140 ;141; 142), and
   a plunger drive (280) for driving the plunger to and between the first and second positions,
   said conveyor means further adapted such that a returnable item which has been positioned in the input area will
   a) fall through the input opening and into the interior space when the plunger is positioned in the first position, and
   b) be forced out of the housing through said exit and towards the storage feed opening by the plunger when the plunger is driven from the first position to the second position.

29. Upwardly oriented storage according to claim 28, wherein the plunger drive is adapted to place the plunger in a third position in which it by its form and positioning substantially covers the input opening, and whereby a returnable item which has been received in the input area is blocked from falling through the input opening by remaining on the plunger when the plunger is placed in the third position.

30. Upwardly oriented storage according to claim 29, wherein the housing has two alternative exits, one at each end of the housing.

31. Upwardly oriented storage according to claim 30, further comprising a third exit opposite and below the input opening.

32. Upwardly oriented storage according to claim 29, wherein the housing (260) has a closable third exit (265)

arranged underneath the input opening (262) and in connection with a third feed opening (144) to a third interior space (114) whereby a free passage is provided in the conveyor means from the input area (210) towards the third interior space when the plunger is positioned in a position that is different from the third position and the closable third exit is in an open state.

33. Upwardly oriented storage according to claim 28, wherein the plunger is provided with an upper surface (271) arranged to face the input opening, and wherein the conveyor means comprises a rotator means (273; 273') adapted for assisting in providing a rotation of a returnable item positioned on the plunger, by a movement of the plunger about the third position.

34. Upwardly oriented storage according to claim 33, comprising a rotator means drive (274; 274') adapted to effect a movement of a surface of the rotator means to a surface velocity corresponding substantially to a surface velocity of the upper surface of the plunger when it is moved past the third position.

35. Upwardly oriented storage according to claim 34, wherein the rotator means is one of a rotary roller, a rotary cylinder, a band or a movable plate.

36. Upwardly oriented storage according to claim 35, wherein the rotator means is rotatably carried by a supporting mounting (275) provided with a weighing cell (276) for determining a mass of a returnable item.

37. Upwardly oriented storage according to claim 36, wherein the plunger on its upper surface (271) has a frictional structure.

38. Upwardly oriented storage according to claim 28, comprising an identification facility (20) for non-contact identification of a returnable item being placed in the input area.

39. Upwardly oriented storage according to claim 38, wherein the identification facility (20) is adapted to employ an energy wave transmitted from the facility (20), and wherein a directional reflector (21) is arranged on the conveyor means (200) for reflecting a transmitted energy wave back towards the identification facility, in particular when the plunger is in the third position.

40. Upwardly oriented storage according to claim 39, wherein the directional reflector is provided on the plunger.

41. Upwardly oriented storage according to claim 28, wherein the housing (260) on a second end has a second exit (264), adapted for being positioned in communication with a second feed opening (142) in a second interior space (112), and
wherein the conveyor means is adapted such that a returnable item which has been received in the input area will:
a) fall through the input opening (262) and into the interior space (261) when the plunger (270) is positioned in the second position, and
b) being forced out of the housing through the second exit (264), preferably also towards the second feed opening of the second interior space, by the plunger when the plunger is driven from the second position and to the first position.

42. Upwardly oriented storage according to claim 1, comprising a return stop means (170) provided with the storage in-feed opening (140, 142) or an exit (224, 263) of the conveyor means for preventing any substantial return movement of a returnable item that has been forced towards the storage feed opening.

43. Upwardly oriented storage according to claim 1, wherein the conveyor means comprises a second exit (226, 226') and the plunger drive is adapted to move the element to the advanced position by rotation of the drum in a second direction of rotation to a third rotational position with the recess opening facing the second exit, which third rotary position is different from the first and second rotary positions, and wherein a returnable item which has been received in the recess when the drum is in the second rotational position with the element in the retracted position will be forced out of the recess and towards the second output by placement of the drum in the first or a fourth rotary position.

44. Upwardly oriented storage according to claim 1, wherein the conveyor means comprises at least one of:
a) a drive element being adapted to in forced pushing or thrust forcing way driving a returnable item towards the storage in-feed opening, and
b) a compactor with a compactor exit positioned proximal to the storage in-feed opening for forcing a compacted returnable item towards the storage in-feed opening.

45. Upwardly oriented storage according to claim 1, wherein the in-feed opening (140, 141) is adapted in size to a maximum returnable item dimension for which the storage is intended, and wherein the interior space (110, 112) exhibits at least one width dimension (111,113) that exceeds substantially the largest dimension of returnable items, whereby a plurality of returned items each exhibiting said largest dimension can be accommodated side by side within the interior space.

46. Upwardly oriented storage according to claim 1, wherein the interior space (110, 112) is dimensioned such that it will effect an at least sideways or at least partly upwards movement of a returnable item being positioned in the interior space when the interior space has been filled up to the feed opening and a further returnable item is forced into the storage by the conveyor means.

47. Upwardly oriented storage according to claim 1, wherein a deflector (180) is provided in the interior space (110).

* * * * *

UNITED STATES PATENT AND TRADEMARK OFFICE
CERTIFICATE OF CORRECTION

PATENT NO. : 7,997,417 B2
APPLICATION NO. : 11/814183
DATED : August 16, 2011
INVENTOR(S) : Geir Sæther It is certified that error appears in the above-identified patent and that said Letters Patent is hereby corrected as shown below:

Column 1
Line 8, change "far" to --for--.

Column 8
Line 60, change "±0°C– 30°" to --±0°– 30°--.

Column 9
Line 35, change "if" to --it-- .

Column 11
Line 57, change "valiant" to --variant--.

Column 17
Line 6, change "273, 273''" to --273, 273'--.

Column 26
Line 16, change "ah" to --all--.

Signed and Sealed this
Twentieth Day of December, 2011

David J. Kappos
*Director of the United States Patent and Trademark Office*